US006912492B1

(12) United States Patent
Johnson et al.

(10) Patent No.: US 6,912,492 B1
(45) Date of Patent: Jun. 28, 2005

(54) METHODS FOR DIAGNOSING, PREVENTING, AND TREATING DEVELOPMENTAL DISORDERS DUE TO A COMBINATION OF GENETIC AND ENVIRONMENTAL FACTORS

(75) Inventors: William G. Johnson, Short Hills, NJ (US); Edward Scott Stenroos, Harrison, NJ (US)

(73) Assignee: University of Medicine & Dentistry of New Jersey, New Brunswick, NJ (US)

( * ) Notice: Subject to any disclaimer, the term of this patent is extended or adjusted under 35 U.S.C. 154(b) by 0 days.

(21) Appl. No.: 09/577,266

(22) Filed: May 23, 2000

Related U.S. Application Data
(60) Provisional application No. 60/136,198, filed on May 25, 1999.

(51) Int. Cl.[7] ................................................. G06N 3/00
(52) U.S. Cl. ............................................. 703/2; 702/20
(58) Field of Search ............................... 703/2; 702/20, 702/19; 435/6

(56) References Cited

U.S. PATENT DOCUMENTS

| | | | |
|---|---|---|---|
| 6,210,950 B1 | 4/2001 | Johnson et al. | 435/252.3 |
| 6,218,120 B1 | 4/2001 | Rozen et al. | 435/6 |
| 6,274,564 B1 * | 8/2001 | Sarill et al. | 514/52 |

FOREIGN PATENT DOCUMENTS

| | | |
|---|---|---|
| WO | WO 90/02203 | 3/1990 |
| WO | WO 99/01560 | 1/1999 |
| WO | WO 00/04194 | 1/2000 |

OTHER PUBLICATIONS

Christensen et al. Genetic polymorphisms in methyltetrahydrofolate reductase and methionine synthase, filate levels in red blood cells, and risk of neural tube defects. Am. J. Medical Genetics (May 21, 1999) vol. 84 (2), pp. 151–157.*
Wilson et al. A common variant in methionine synthase reductase combined with low cobalamin (vitamin B12) increases risk for spina bifida. Molecular Genetics and Metabolism (Aug. 1999) vol. 67 (4), pp. 317–323.*
Maggio et al. Effects of methylfolate in the treatemtn of heterozygous beta–thalassemia patients. Current Therapeutic Research. 1994. vol. 55, No. 12, pp. 1471–1476, abstract only.*
Steen et al. Neural–tube defects are associated with low concentrations of cobalamin (vitamin B12) in amniotic fluid. Prenatal Diagnosis. 1998. vol. 18, No. 6, pp. 545–555.*
Allen LH, Am J Clin Nutr (1995)Nov;62(5):1013–9.
Anderson JL, J Am Coll Cardiol(Nov. 1997);30(5):1206–11.
Andreasen NC, Science(Oct. 14, 1994),266(5183):294–8.
Baird DD, Hum Reprod(Dec. 1997)12(12):2607–13.
Baron M, Acta Psychiatr Scand (Aug. 1995);92(2):81–6.
Bassett AS, Br J Psychiatry(Sep. 1992)161:323–34.
Bates CJ, Eur J Clin Nutr (Sep. 1994)48(9):660–8.
Benjamin J, Gershon ES, Biol Psychiatry (Sep. 1, 1996)40(5):313–6.
Bogerts B, Arch Gen Psychiatry(Aug. 1985)42(8):784–91.
Boyd JH, Schizophr Bull(1986),12(2):173–86.
Carmel R, Arch Intern Med(Nov. 1987);147(11):1995–6.
Carpenter WT Jr, Buchanan RW, N Engl J Med(Mar. 10, 1994);330(10):681–90.
Chatkupt S, Am J Med Genet(Nov. 1, 1992)44(4):508–12.
Cooper BA, Rosenblatt DS, Annu Rev Nutr (1987); 7:291–320.
Detera–Wadleigh SD, Nucleic Acids Res (Aug. 11, 1989); 17(15):6432.
Dohrenwend BP, Science (Feb. 21, 1992);255(5047): 946–52.
Duff EM, Cooper ES, Am J Public Health (Mar. 1994)84(3):473–6.
Eaton WW, Schizophr Res(Mar. 1992);6(3):181–92.
Falk CT, Rubinstein P, Ann Hum Gene(Jul. 1987); 51 (Pt 3):227–33.
Feder JN, Nucleic Acids Res(Jul. 24, 1987); 15(14):5906.
Fermo I, Ann Intern Med(Nov. 15, 1995);123(10):747–53.
Freeman JM, N Engl J Med(Mar. 6, 1975);292(10):491–6.
Gadowsky SL, J Adolesc Health (Jun. 1995);16(6):465–74.
Gilliam TC, Genomics (Nov. 1989);5(4):940–4.
Godfrey PS, Lancet(Aug. 18, 1990);336(8712):392–5.
Gordon N, Brain Dev (Sep.–Oct., 1995);17(5):307–11.
Gottesman II, Clin Genet (Jul. 1994);46(1 Spec No):116–23.
Grant SF, Nat Genet (Oct. 1996);14(2):203–5.
Green MF, Psychiatry Res(Aug. 1994); 53(2):119–27.
Guaraldi GP, Ann Clin Psychiatry(Jun. 1993)5(2):101–5.
Heutink P, Am J Hum Genet(Aug. 1995);57(2):465–73.
Hitzig WH, Ciba Found Symp(1978)(68):77–91.
Horie N, Cell Struct Funct(Jun. 1995):20(3):191–7.
Hornsby PP, Epidemiology(Mar. 1998);9(2):193–8.
Jeste DV, Br J Psychiatry(Oct. 1988); 153:444–59.
Kendall RE, Kemp IW, Arch Gen Psychiatry(Oct. 1989)46(10):878–82.
Kendall RE, Adams W, Br J Psychiatry(Jun. 1991); 158:758–63.
Kirch DG, Schizophr Bull (1993);19(2):355–70.
Kirke PN, Q J Med (Nov. 1993)86(11):708–8.
Kovelman JA, Scheibel AB, Biol Psychiatry(Dec. 1984); 19(12):1601–21.
Lewis BA, Behav Genet (May 1993);23(3):291–7.
Li N, Biochim Biophys Acta(Oct. 18, 1994);1219(2): 515–20.

(Continued)

*Primary Examiner*—Marjorie Moran

(57) ABSTRACT

The present invention discloses a novel method for identifying an individual who may be susceptible to develop a developmental disorder. In one particular example, an individual is identified who is genetically susceptible to becoming schizophrenic. In addition, the present invention discloses a novel method for identifying individuals who are genetically susceptible to have offspring with a developmental disorder. Methods of diagnosing, preventing and treating developmental disorders such as schizophrenia are also provided.

8 Claims, 5 Drawing Sheets

OTHER PUBLICATIONS

Lombroso PJ, J Am Acad Child Adolesc Psychiatry (Sep. 1994);33(7):921–38.
Louis–Ferdinand RT, Adverse Drug React Toxicol Rev (1994 Winter);13(4):193–206.
McPartlin J. Lancet(Jan. 16, 1993); 341(8838):148–9.
Mednick SA, Arch Gen Psychiatry (Feb. 1988);45(2):189–92.
Metz J, Am J Hematol (Apr. 1995);48(4):251–5.
Molloy AM, Lancet (May 31, 1997);349(9065):1591–3.
Morita H, Circulation (Apr. 15, 1997)95(8):2032–6.
Naurath HJ, Lancet(Jul. 8, 1995);346(8967):85–9.
O'Callaghan E, Br J Psychiatry(Jun. 1991); 158:764–9.
Owen MJ, Psychol Med May 1992;22(2)289–93.
Pauls DL, Adv Neurol 1992;58:151–7.
Pyper CM∎ Eur J Contracept Reprod Health Care 1997 Jun;2(2):131–46.
Regland B, J Neural Transm Gen Sect 1994;98(2):143–52.
Reynolds EH, Lancet Jul. 28, 1984;2(8396):196–8.
Sanders TA, Reddy S, Am J Clin Nutr May 1994;59(5 Suppl):1176S–1181S.
Scholl TO, Am J Clin Nutr Apr. 1996;63(4):520–5.
Schorah CJ, Wild J, Lancet May 29, 1993;341 (8857):1417.
Shapiro RM, Schizophr Res Oct. 1993;10(3):187–239.
Shen F, Biochemistry Feb. 8, 1994;33(5):1209–15.
Sherrington R, Nature Nov. 10, 1988;336(6195):164–7.
Shevell MI, Rosenblatt DS, Can J Neurol Sci Nov. 1992;19(4):472–86.
Spielman RS, Am J Hum Genet Mar. 1993;52(3):506–16.
Susser E, Arch Gen Psychiatry Jan. 1996;53(1):25–31.
Susser ES, Lin SP, Arch Gen Psychiatry Dec. 1992;49(12):983–8.
Terwilliger JD, Ott J, Hum Hered 1992;42(6):337–46.
Torrey EF, Bowler A, Schizophr Bull 1990;16(4):591–604.
Torrey EF, Schizophr Bull 1993;19(3):557–62.
Trakatellis A, Postgrad Med J Oct 1997;73(864):617–22.
van der Put NM, Lancet Oct. 21, 1995;346(8982):1070–1.
Weiffenbach B, Genomics May 1991;10(1):173–85.
Weinberg CR, Wilcox AJ, Lie RT∎ Am J Hum Genet Apr. 1998;62(4):969–78.
Weinberger DR, Arch Gen Psychiatry Jul. 1987;44(7):660–9.
Whitehead AS, QJM Nov. 1995;88(11):763–6.
Wilcox AJ, Am J Epidemiol Nov. 1, 1998;148(9):893–901.
Wilcox AJ, Hum Reprod Feb. 1998;13(2):394–7.
Wouters MG, Fertil Steril Nov. 1993;60(5):820–5.
Yang JK, J Mol Biol Jun. 25, 1984;176(2):169–87.
Arinami et al., *American Journal of Medical Genetics*, 74:526–528 (1997).
Brown et al., *Journal of Nervous and Mental Disease*, 184:71–85 (1996).
Chen et al., *Journal of Biological Chemistry*, 259:3933–3943 (1984).
Lewis et al., *Annals of Pharmacotherapy*, 32:1087–1095 (1998).
Pauling, *Journal of Nutritional & Environmental Medicine*, 5:187–198 (1995).
Naurath et al., *Lancet (North American Edition)*, 346:85–89 (1995).
Regland et al., *J. Neural Transm*, 104:931–941 (1997).
Database EMBL 'Online? Acc. nb. AA744384, Jan. 19, 1998 abstract only.
Noe et al., *The Journal of Biological Chemistry*, 274:27807–27814 (1999).
Noe et al., Abstract for the Animal Meeting of the RNA Society, *2000, Dept. of Biochemistry, School of Pharmacy, University of Barcelona and Dept. of Biological Sciences, Columbia University* (2000).

* cited by examiner

FIG. 1

Primers for PCR Amplification the DHFR Deletion Polymorphism Region

Forward primer(SEQ ID NO:38):  5'-CTA AAC TGC ATC GTC GCT GTG-3'

Reverse primer(SEQ ID NO:39):  5'-AAA AGG GGA ATC CAG TCG G-3'

Genotypes of the DHFR 19 bp Deletion by Non-Polyacrylamide Gel Electrophoresis

FIG. 3

Sequences of PCR Amplification Products
in the Region of the DHFR Deletion Polymorphism Region

```
                                                       *
Allele 1  GCTGCCCACGGTCGGGGTACCTGGGCGGGACGCGCCAGGCCGACTCCCGGCGAGA
          | | | | | | | | | | | | | | | | |               | | | | | | | | | | | | | | | | |
Allele 2  GCTGCCCACGGTCGGGGT..................GGCCGACTCCCGGCGAGA
```

FIG. 4A

```
   1 CTGCAGCGCC AGGGTCCACC TGGTCGGCTG CACCTGTGGA GGAGGAGGTG
  51 GATTTCAGGC TTCCCGTAGA CTGGAAGAAT CGGCTCAAAA CCGCTTGCCT
 101 CGCAGGGGCT GAGCTGGAGG CAGCGAGGCC GCCCGACGCA GGCTTCCGGC
 151 GAGACATGGC AGGGCAAGGA TGGCAGCCCG GCGGCAGGGC CCGGCGAGGA
 201 GCGCGAACCC GCGGCCGCAG TTCCCAGGCG TCTGCGGGCG CGAGCACGCC
 251 GCGACCCTGC GTGCGCCGGG GCGGGGGGGC GGGGCCTCGC CTGCACAAAT
 301 AGGGACGAGG GGGCGGGGCG GCCACAATTT CGCGCCAAAC TTGACCGCGC
 351 GTTCTGCTGT AACGAGCGGG CTCGGAGGTC CTCCCGCTGC TGTCATGGTT
 401 GGTTCGCTAA ACTGCATCGT CGCTGTGTCC CAGAACATGG GCATCGGCAA
 451 GAACGGGGAC CTGCCCTGGC CACCGCTCAG GTATCTGCCG GGCCGGGGCG
 501 ATGGGACCCA AACGGGCGCA GGCTGCCCAC GGTCGGGTA CCTGGGCGGG
 551 ACGCGCCAGG CCGACTCCCG GCGAGAGGAT GGGGCCAGAC TTGCGGTCTG
 601 CGCTGGCAGG AAGGGTGGGC CCGACTGGAT TCCCCTTTTC TGCTGCGCGG
 651 GAGGCCCAGT TGCTGATTTC TGCCCGGATT CTGCTGCCCG GTGAGGTCTT
 701 TGCCCTGCGG CGCCCTCGCC CAGGGCAAAG TCCCAGCCCT GGAGAAAACA
 751 CCTCACCCCT ACCCACAGCG CTCCGTTTGT CAGGTGCCTT AGAGCTCGAG
 801 CCCAAGGGAT AATGTTTCGA GTAACGCTGT TTCTCTAACT TGTAGGAATG
 851 AATTCAGATA TTTCCAGAGA ATGACCACAA CCTCTTCAGT AGAAGGTAAT
 901 GTGGGATTAA GTAGGGTCTT GCTTGATGAA GTTACCAGT GCAAATGTTA
 951 GTTAAATGGA AAGTTTTCCG TGTTAATCTG GGACCTTTTC TCTTATTATG
1001 GATCTGTATG ATCTGTATGC AGTTCCCAAG GTTCATTTAC CATTATTAAA
1051 AAATTTTTGT CTTAGAAATT TTATGTATGT CAACGCACGA GCAAATTATC
1101 AGGCATGGGG CAGAATTGGC AACTGGGTGG AGGCTTCGGT GGAGGTTAGC
1151 ACTCCGAAAG GAAAACAGAG TAGGCCTTTG AACAGCTGC TGGAAGAGAT
1201 AAGGCCTGAA CAAGGGCAGT GGAGAAGAGA GGGTAAAAAT TTTTTAAGGT
1251 TACATGACCC TGGATTTTGG AGATC
```

FIG 4B

```
   1 CTGCAGCGCC AGGGTCCACC TGGTCGGCTG CACCTGTGGA GGAGGAGGTG
  51 GATTTCAGGC TTCCCGTAGA CTGGAAGAAT CGGCTCAAAA CCGCTTGCCT
 101 CGCAGGGGCT GAGCTGGAGG CAGCGAGGCC GCCCGACGCA GGCTTCCGGC
 151 GAGACATGGC AGGGCAAGGA TGGCAGCCCG GCGGCAGGGC CCGGCGAGGA
 201 GCGCGAACCC GCGGCCGCAG TTCCCAGGCG TCTGCGGGCG CGAGCACGCC
 251 GCGACCCTGC GTGCCGGG GCGGGGGGC GGGGCCTCGC CTGCACAAAT
 301 AGGGACGAGG GGGCGGGGCG GCCACAATTT CGCGCCAAAC TTGACCGCGC
 351 GTTCTGCTGT AACGAGCGGG CTCGGAGGTC CTCCCGCTGC TGTCATGGTT
 401 GGTTCGCTAA ACTGCATCGT CGCTGTGTCC CAGAACATGG GCATCGGCAA
 451 GAACGGGGAC CTGCCCTGGC CACCGCTCAG GTATCTGCCG GGCCGGGGCG
 501 ATGGGACCCA AACGGGCGCA GGCTGCCCAC GGTCGGGGT
 551          GG CCGACTCCCG GCGAGAGGAT GGGGCCAGAC TTGCGGTCTG
 601 CGCTGGCAGG AAGGGTGGGC CCGACTGGAT TCCCCTTTTC TGCTGCGCGG
 651 GAGGCCCAGT TGCTGATTTC TGCCCGGATT CTGCTGCCCG GTGAGGTCTT
 701 TGCCTGCGG CGCCCTCGCC CAGGGCAAAG TCCCAGCCCT GGAGAAAACA
 751 CCTCACCCCT ACCACAGCG CTCCGTTTGT CAGGTGCCTT AGAGCTCGAG
 801 CCCAAGGGAT AATGTTTCGA GTAACGCTGT TTCTCTAACT TGTAGGAATG
 851 AATTCAGATA TTTCCAGAGA ATGACCACAA CCTCTTCAGT AGAAGGTAAT
 901 GTGGGATTAA GTAGGGTCTT GCTTGATGAA GTTTACCAGT GCAAATGTTA
 951 GTTAAATGGA AAGTTTTCCG TGTTAATCTG GGACCTTTTC TCTTATTATG
1001 GATCTGTATG ATCTGTATGC AGTTCCCAAG GTTCATTTAC CATTATTAAA
1051 AAATTTTGT CTTAGAAATT TTATGTATGT CAACGCACGA GCAAATTATC
1101 AGGCATGGGG CAGAATTGGC AACTGGGTGG AGGCTTCGGT GGAGGTTAGC
1151 ACTCCGAAAG GAAAACAGAG TAGGCCTTTG AACAGCTGC TGGAAGAGAT
1201 AAGGCCTGAA CAAGGGCAGT GGAGAAGAGA GGGTAAAAAT TTTTTAAGGT
1251 TACATGACCC TGGATTTTGG AGATC
```

METHODS FOR DIAGNOSING, PREVENTING, AND TREATING DEVELOPMENTAL DISORDERS DUE TO A COMBINATION OF GENETIC AND ENVIRONMENTAL FACTORS

CROSS-REFERENCE TO RELATED APPLICATIONS

The present application is a non-provisional application claiming the benefit of copending provisional U.S. Ser. No. 60/136,198 filed May 25, 1999, the disclosure of which is hereby incorporated by reference in its entirety. Applicants claim the benefits of this application under 35 U.S.C. §119(e).

FIELD OF THE INVENTION

The invention relates generally to novel methods of diagnosing, preventing, and treating specific diseases which are caused by a combination of genetic and environmental factors. One such disease exemplified is schizophrenia.

BACKGROUND OF THE INVENTION

The term "schizophrenia" was introduced by Bleuler in the beginning of this century to encompass a dissociation or disruption of thought processes, along with a dichotomy among thought, emotion, and behavior [Bleuler, *Translation J. Zinkin*, New York: International University Press (1950)]. The current definition of schizophrenia includes a break with reality that is usually manifested as hallucinations, delusions, or disruption in thought processes [Carpenter et al., *Medical Progress*, 330:681–690(1994)]. At present the nationally accepted definition for the diagnosis of schizophrenia is contained in Diagnostic and Statistical Manual for Mental Disorders, Fourth Edition, Washington, D.C (1994): American Psychiatric Association, hereby incorporated by reference in its entirety.

Schizophrenia is a clinical syndrome that has a profound influence on public health. The symptoms for schizophrenia begin early in life, and continues for most patients throughout their lives. An estimate of the direct and indirect costs of schizophrenia was thirty-three billion dollars for 1990 in the United States alone [Carpenter et at, 1994, supra]. Indeed, one of every forty dollars spent for total heath care expenditures in the United States is spent on treating schizophrenia [Rupp et al., *Psychiatric Clin. North Am.*, 16:413–423 (1993)]. Furthermore, estimates have been made suggesting that up to 50% of the homeless American population is schizophrenic [Bachrach, In: *Treating the Homeless Mentally III*, Washington, D.C., American Psychiatric Press, 13–40, Lamb et at ed. (1992)].

The genetic factors in schizophrenia, though clearly documented to be present, are not simple [Carpenter and Buchanan, *N. Engl. J. Med.*, 330:681–689 (1994); Gottesman, *Clin. Genet.*, 46:116–123 (1994)]. Schizophrenia is, at least in part, a neurodevelopmental disorder, a birth defect in which the brain has been subtly damaged during development [Carpenter and Buchanan, *N. Engl. J. Med.*, 330:681–689 (1994); Weinberger, *Arch. Gen. Psychiatry*, 44:660–669 (1987); Brixey et al., *J. Clin. Psychol.*, 49:447–456 (1993)]. Evidence of this damage is seen both at autopsy [Kovelman and Scheibel, *Biol. Psychiatry*, 19:1601–1621 (1984); Bogerts et al., *Arch. Gen. Psychiatry*, 42:784–791 (1985); Jakob and Beckman, *J. Neural Transm.*, 65:303–326 (1986); Brown et al., *Arch. Gen. Psychiatry*, 43:36–42 (1986); Benes and Bird, *Arch Gen Psychiatry*, 44:608–616 (1987); Colter et al., *Arch Gen Psychiatry*, 44:1023 (1987); Altshuler et al., *Arch. Gen. Psychiatry*, 47:1029–1034 (1990); Pakkenberg, *Schizophr. Res.*, 7:95–100 (1992); Bogerts, *Schizophr. Bull.*, 19:431–445 (1993); Shapiro, *Schizophr. Res.*, 10:187–239 (1993)] and by neuroimaging [Jeste et al., *Br. J. Psychiatry*, 153:444–459 (1988); Suddath et al., *Am. J. Psychiatry*, 146:464–472 (1989); Suddath et al., *N. Engl. J. Med.*, 322:789–794 (1990); DeLisi et al., *Biol. Psychiatry*, 29:159–175 (1991); Breier et al., *Arch. Gen. Psychiatry*, 49:921–926 (1992); O'Callaghan et al., *J. R. Soc. Med.*, 85:227–231 (1992); Bogerts et al., *Biol. Psychiatry*, 33:236–246 (1993); Andreasen et al., *Science*, 266:294–298 (1994)]. The pattern of this brain damage and the presence of minor congenital abnormalities point to an insult occurring during the second trimester of fetal development [Bracha et al., *Biol. Psychiatry*, 30:719–725 (1991); Bracha et al., *Am. J. Psychiatry*, 149:1355–1361 (1992); Green et al., *Psychiatry Res.*, 53:119–127 (1994)]. Epidemiological studies have documented a season-of-birth effect by which schizophrenics are more frequently born during winter and early spring than during other seasons [Boyd et al., *Schizophr. Bull.*, 12:173–186 (1986); Kendell and Adams, *Br. J. Psychiatry*, 158:758–763 (1991); O'Callaghan et al., *Br. J. Psychiatry*, 158:764–769 (1991)]. Also, individuals exposed to an influenza epidemic [Mednick et al., *Arch. Gen. Psychiatry*, 45:189–192 (1988); Barr et al., *Arch. Gen. Psychiatry*, 47:869–874 (1990); O'Callaghan et al., *Lancet.*, 337:1248–1250 (1991); Murray et al., *J. Psychiatry. Res.*, 26:225–235 (1992); Adams et al., *Br. J. Psychiatry*, 163:522–534 (1993)] or famine [Susser and Lin, *Arch. Gen. Psychiatry*, 49:983–988 (1992)] during their second trimester of fetal development have increased risk of later developing schizophrenia, according to some studies but not others [Kendell, *Arch. Gen. Psychiatry*, 46:878–882 (1989); Crow and Done, *Br. J. Psychiatry*, 161:390–393 (1992)]. This has suggested that an environmental effect such as dietary deficiency, virus infection [Kirch, *Schizophr. Bull.*, 19:355–370 (1993)], vitamin deficiency, or effect of cold weather may be acting during fetal development.

Linkage mapping studies in schizophrenia have been difficult. Recently, some studies [Straub et al., *Nature Genet.*, 11:287–293 (1995); Schwab et al., *Nature Genet.*, 11:325–327 (1995); Moises et al., *Nature Genet.*, 11:321–324 (1995)] have supported a gene locus on chromosome 6 (6p24-22, near the HLA region) as having an effect in schizophrenia; other studies gave little or no support to a marker in this region [Wang et al., *Nature Genet.*, 10:41–46 (1995); Mowry et al., *Nature Genet.*, 11:233–234 (1995); Gurling et al., *Nature Genet.*, 11:234–235 (1995); Antonarakis et al., *Nature Genet.*, 11:235–236 (1995)]. At best this locus appeared to be involved in only about 15–30% of families [Straub et al., 1995, supra]. Also, some evidence for loci on chromosomes 3 [Pulver et al., *Am. J. Med. Genet.*, 60:252–260 (1995), 8 [Pulver et al., *Am. J. Med. Genet.*, 60:252–260 (1995); Kendler et al., *Am. J. Psych.* 153:1534–1540 (1996), 9 [Coon et al., *Biol. Psychiatry*, 34:277–289 (1993); Moises et al., *Nature Genet.*, 11:321–324 (1995)] and 22 [Coon et al., *Am. J. Med. Genet.*, 54:72–79 (1994); Pulver et al., *Am. J. Med. Genet.*, 54:3–43 (1994)] have been reported. In addition, two polymorphic markers very close to the gene encoding dihydrofolate reductase (DHFR) on chromosome 5q, D5S76 and D5S39, gave very high lod scores (as high as 6.49, i.e. odds of about 3 million to one in favor of genetic linkage versus chance occurrence) in 7 British and Icelandic schizophrenia families studied [Schwab et al., *Nat. Genet.* 11:325–327

(1997); Straub et al., Molec Psychiatr. 2:148–155 (1997)]. However, this result could not be confirmed in studies of numerous other families.

There could be several reasons for this difficulty. First, there may be more than one gene involved, (locus heterogeneity). Second, the genetic factor(s) may be common in the population (high disease allele frequency), thus diminishing the power of linkage studies [Terwilliger and Ott, *Handbook of Human Genetic Linkage*, Baltimore: Johns Hopkins Univ. Pr., 181 (1994)]. Third, the correct genetic model may be unknown [Owen, *Psychol. Med.*, 22:289–293 (1992)]. Any or all of these factors could diminish the power of a linkage study sufficiently to make success very difficult [Terwilliger and Ott, 1994, supra].

Thus the current (developmental) model for schizophrenia is that genetic and environmental factors cause brain damage in a fetus that later develops schizophrenia. However, the genetic and environmental factors have not been identified. Also, extensive linkage and association studies have failed to identify genes determining schizophrenia.

Indeed, schizophrenia appears to be just one of a family of developmental disorders whose cause has not been identified. Other such developmental disorders are defined by the Diagnostic and Statistical Manual for Mental Disorders, Fourth Edition, Washington, D.C (1994) and include: Tourette Syndrome which is identical to Tourette's Disorder and is a subcategory of Tic Disorders; Bipolar Disorder which is identical with Bipolar I Disorder or Bipolar II disorder, Autism which is identical with Autistic Disorder which is a subcategory of Pervasive Developmental Disorders; Conduct disorder which is a subcategory of Attention-Deficit and Disruptive Behavioral Disorders; Attention-Deficit Hyperactivity Disorder which is identical to Attention-Deficit/Hyperactivity Disorder and to Attention-Deficit/Hyperactivity Disorder NOS (not otherwise specified) which is also a subcategory of Attention-Deficit and Disruptive Behavioral Disorders; Obsessive-Compulsive Disorder which is a subtype of Anxiety Disorders; Chronic Multiple Tics Syndrome which is identical to Chronic Motor or Vocal Tic Disorder which is a subtype of Tic Disorders; and Learning Disorders.

In addition Spina bifida is a developmental disorder. Spina bifida is a form of neural tube defect in which neural elements (spinal nerves or spinal chord) or coverings of the brain and spinal chord (dura mater, arachnoid mater) herniate through a midline defect into a cystic cavity covered completely or partially by skin.

Therefore, there is a need for new methods of diagnosing individuals susceptible to developing a developmental disorder. In addition, there is a need for methods of identifying individuals susceptible to having offspring that develop a developmental disorder. Finally, there is a need for a method of treating such susceptible individuals in order to prevent and/or ameliorate the symptoms due to and/or associated with the developmental disorder.

The citations of any reference herein should not be construed as an admission that such reference is available as "Prior Art" to the instant application.

SUMMARY OF THE INVENTION

The present invention provides methods of diagnosing, preventing and/or treating specific developmental disorders. Towards this end the present invention provides methods of identifying an individual as being genetically or environmentally susceptible for developing or having a developmental disorder or for having offspring that develop the developmental disorder. Such a developmental disorder can be schizophrenia, spina bifida cystica, Tourette's syndrome, bipolar illness, autism, conduct disorders, attention deficit disorder, obsessive compulsive disorder, chronic multiple tic syndrome and learning disorders such as dyslexia. In addition, any of the methods provided herein for identifying an individual as being genetically and/or environmentally susceptible for having or developing a developmental disorder or for having offspring that develop the developmental disorder can also be used in diagnosing the individual, preferably in conjunction with a clinical diagnosis.

Therefore, the present invention provides methods of identifying an individual as being genetically susceptible for having or developing a developmental disorder.

The present invention further provides methods of identifying an individual as being genetically susceptible for having offspring that are susceptible for developing a developmental disorder. Methods of identifying an individual as being susceptible due to environmental factors for having or developing a developmental disorder are also provided. In addition, the present invention provides methods of identifying an individual as being susceptible of having offspring that are susceptible for developing a developmental disorder. The present invention also provides methods of identifying an individual as being susceptible for having or developing a developmental disorder due to both environmental and genetic factors. The present invention further provides methods of identifying an individual as being susceptible for having offspring that are susceptible for developing a developmental disorder.

The present invention therefore provides methods for compiling genetic reference datasets, environmental reference datasets and/or genetic and environmental reference datasets for use in determining a predicted probability for an individual of having a susceptibility for having or developing a developmental disorder, or for having offspring that develop a developmental disorder.

In one aspect of the invention, the present invention provides methods that comprise generating a genetic reference dataset for use in determining the predicted probability of an individual for having a susceptibility for having or developing a developmental disorder due to genetic factors, or for having offspring that develop a developmental disorder due to genetic factors.

One such embodiment comprises collecting a biological sample from a human subject. The human subject can be a diagnostic proband, a blood relative of the diagnostic proband, an affected proband, a blood relative of the affected proband, a control proband, and/or a blood relative of the control proband. The biological sample contains nucleic acids and/or proteins from the human subject. The nucleic acids and/or proteins from the biological sample are then analyzed resulting in a partial or full genotype for the alleles of the genes involved in folate, pyridoxine, and/or cobalamin metabolism. The partial or full genotype then forms a dataset of genetic explanatory variables for the human subject. The dataset of genetic explanatory variables is then compiled from multiple human subjects into a genetic reference dataset. Such compilations are exemplified in the Detailed Description and Examples below.

In another aspect, the present invention provides a method that comprises generating a genetic and environmental reference dataset for use in determining the predicted probability of an individual for having a susceptibility for having or developing a developmental disorder due to genetic factors and environmental factors, or for having offspring that develop a developmental disorder due to genetic factors and environmental factors. One such embodiment comprises obtaining dietary and epidemiological information for environmental explanatory variables for the human subjects and combining the environmental explanatory variables with a genetic reference dataset for the human subjects as described above.

In another aspect, the present invention provides an environmental reference dataset for use in the determination of the predicted probability for an individual for having a susceptibility for having or developing a developmental disorder due to environmental factors, or for having offspring that develop a developmental disorder due to environmental factors One such embodiment comprises obtaining dietary and epidemiological information for environmental explanatory variables for a human subject. The human subject can be a diagnostic proband, a blood relative of the diagnostic proband, an affected proband, a blood relative of the affected proband, a control proband, or a blood relative of the control proband. The dataset of environmental explanatory variables is then compiled from multiple human subjects into an environmental reference dataset for the human subjects.

The developmental disorder forming the basis of the reference datasets of the present invention can be schizophrenia, or spina bifida cystica, or Tourette's syndrome, or dyslexia, or conduct disorder, or attention-deficit hyperactivity disorder, or bipolar illness, or autism, or chronic multiple tic syndrome or obsessive-compulsive disorder, or like disorders. A blood relative is preferably the mother of the individual, a sibling, the father or a grandparent of the individual. When the reference dataset is for use in the determination of the predicted probability for an individual of having a susceptibility for having offspring that develop a developmental disorder, the individual is preferably a pregnant woman. The reference datasets of the present invention are themselves part of the present invention.

The present invention further provides methods of estimating the genetic susceptibility of an individual to have or to develop a developmental disorder, or to have offspring that develop a developmental disorder. In one such embodiment the method comprises collecting a biological sample from a participant (or participants) who is either the individual or a blood relative of the individual. The biological sample contains nucleic acids and/or proteins of the participant. The analysis of the nucleic acids and/or proteins from the biological sample yield a partial or full genotype for the alleles of the genes involved in folate, pyridoxine, and/or cobalamin metabolism. The partial or full genotype forms a dataset of genetic explanatory variables for the participants. The dataset of genetic explanatory variables obtained are added to a genetic reference dataset forming a combined genetic dataset. A model is then formulated comprising the genetic explanatory variables obtained from the participants and the combined genetic dataset is analyzed. A predicted probability for the individual for having and/or developing a developmental disorder and/or having offspring that develop a developmental disorder is then determined. The genetic susceptibility of an individual to have or to develop a developmental disorder and/or have offspring that develop a developmental disorder is estimated. In a preferred embodiment, analyzing the combined genetic dataset is performed by binary linear regression. In a more preferred embodiment, the binary linear regression is performed with the SAS system. In another preferred embodiment, the model is modified by adding or subtracting one or more genetic explanatory variables and the combined genetic dataset is re-analyzed, preferably by binary logistic regression. In this case a model is chosen that best fits the data. This can be accomplished by testing the model for goodness of fit.

The present invention also provides methods of estimating the genetic and environmental susceptibility of an individual to have or to develop a developmental disorder and/or for having offspring that develop a developmental disorder. One such embodiment comprises collecting a biological sample from one or more participants.

Again, the participant is either the individual or a blood relative of the individual. The biological sample contains nucleic acids and/or proteins of the participant. The nucleic acids and/or proteins from the biological sample are analyzed resulting in a partial or full genotype for the alleles of the genes involved in folate, pyridoxine, and/or cobalamin metabolism. The partial or full genotype forms a dataset of genetic explanatory variables for the participant. Dietary and epidemiological information for environmental explanatory variables for the participant(s) are also obtained which are used to form a dataset of environmental explanatory variables for the participant(s). The datasets of genetic explanatory variables and the dataset of environmental explanatory variables are added to a genetic and environmental reference dataset forming a combined genetic and environmental dataset. A model is formulated comprising the genetic and environmental explanatory variables obtained from the participant(s). The combined genetic and environmental dataset is then analyzed and a predicted probability for the individual for having and/or developing a developmental disorder and/or for having offspring that develop a developmental disorder is determined. The genetic and environmental susceptibility of an individual to have or to develop a developmental disorder and/or have offspring that develop a developmental disorder is estimated. In a preferred embodiment, analyzing the combined genetic and environmental dataset is performed by binary linear regression. In a more preferred embodiment the binary linear regression is performed with the SAS system. In another preferred embodiment the model is modified by adding or subtracting one or more genetic and/or environmental explanatory variables and the combined genetic and environmental dataset is re-analyzed preferably, by binary logistic regression. In this case a model is chosen that best fits the data. This can be accomplished by testing the model for goodness of fit.

For any of these methods, the developmental disorder can be schizophrenia, spina bifida cystica, Tourette's syndrome, bipolar illness, autism, conduct disorder, attention deficit hyperactivity disorder, obsessive compulsive disorder, chronic multiple tic syndrome and learning disorders such as dyslexia.

In a particular embodiment, the individual is suspected of being genetically susceptible of having or for developing the developmental disorder and/or of being genetically susceptible of having offspring that develop the developmental disorder. In a preferred embodiment of this type, the individual is suspected of being genetically susceptible for having or for developing the developmental disorder and/or of being genetically susceptible of having offspring that develop the developmental disorder because a blood relative has the developmental disorder. In one such embodiment the blood relative is a parent, a sibling, or a grandparent. In a preferred embodiment the blood relative is the mother of the individual. In a particular embodiment in which the individual is suspected of being genetically susceptible of having offspring that develop the developmental disorder, the individual is a pregnant woman. In another such embodiment the individual is the mate of the pregnant woman. In a particular embodiment exemplified below, the developmental disorder is schizophrenia.

Since the availability of the data regarding the genetic and environmental explanatory factors can vary in separate determinations, variations in the explanatory factors used is clearly envisioned by the present invention.

The present invention further provides methods of lowering the risk of a pregnant woman to have a child that will develop a developmental disorder. One such embodiment comprises administering methylfolate, cobalamin or pyridoxine to the pregnant woman and/or fetus, which lowers the risk of the pregnant woman to give birth to a child with a developmental disorder. In a particular embodiment of this type, the pregnant woman had been previously determined to be susceptible of having offspring that develop a developmental disorder by a method disclosed herein. The present invention further provides a method of determining if any treatment is advisable for a pregnant woman that is genetically susceptible to having offspring that develop a developmental disorder which comprises determining the concentration of a risk factor from a tissue sample or body fluid from the pregnant woman. When the concentration of the risk factor is statistically above or below an accepted normal range, treatment is advisable.

The present invention further provides methods of determining if any treatment is advisable for a pregnant woman who has been determined to be susceptible to having offspring that develop a developmental disorder. One such embodiment comprises determining the concentration of a risk factor from a tissue sample or body fluid from the pregnant woman. When the concentration of the risk factor is statistically above or below an accepted normal range, treatment is advisable. In a particular embodiment of this type, the pregnant woman had been previously determined to be susceptible of having offspring that develop a developmental disorder by a method disclosed herein.

Methods of monitoring the effect of the administration of methylfolate, cobalamin or pyridoxine to the pregnant woman who has been determined to be susceptible to having offspring that develop a developmental disorder are also included in the present invention. One such embodiment comprises determining the concentration of a risk factor from a tissue sample or body fluid from the pregnant woman. When the concentration of the risk factor is statistically within an accepted normal range, the treatment is deemed effective. In a particular embodiment of this type, the pregnant woman had been previously determined to be susceptible of having offspring that develop a developmental disorder by a method disclosed herein. The risk factor can be any substance and/or metabolite linked to folate and/or cobalamin and/or pyridoxine metabolism. In one embodiment, the risk factor is homocysteine. In yet another embodiment, the risk factor is folate. In still another embodiment, the risk factor is cobalamin.

The present invention also provides a method of treating an asymptomatic individual determined to be susceptible for developing a developmental disorder comprising administering methylfolate, cobalamin and/or pyridoxine. In a particular embodiment of this type, the asymptomatic individual had been previously determined to be susceptible of developing a developmental disorder by a method disclosed herein.

The DNA samples from the persons tested may be obtained from any source including blood, a tissue sample, amniotic fluid, a chorionic villus sampling, cerebrospinal fluid, and urine.

The present invention includes but is not limited to the examples of proteins encoded by genes involved in folate, cobalamin and pyridoxine metabolism compiled in Tables 2–7 in the Detailed Description of the Invention, below. For certain genes nucleic acid and/or amino acid sequence data is also provided. These genes and related sequence data are solely intended as examples of genes that are suitable to be used in the methods described herein. Such sequence data can be used for carrying out the genetic analysis of the present invention. However, the present invention is not intended to be limited in any way to such lists of proteins or the related sequence data.

It is further contemplated by the present invention to provide methods that include the testing for a genetic mutations in individual genes involved in folate and cobalamin metabolism and/or in individual combinations of such genes (e.g., methylenetetrahydrofolate reductase gene and methionine synthase). In addition, all possible combinatorials, and permutations of such genes including a constellation comprising all of the genes involved in folate, pyridoxine, and cobalamin metabolism is envisioned by the present invention. Alternatively, a constellation of genes in which any one or more genes can be excluded from those tested is also contemplated by the present invention (for example, a given constellation of genes can include genes encoding all of the proteins in Table 2 and 4 except the folate receptor 2-like protein). Thus all of such possible constellations are envisioned by, and are therefore part of the present invention.

The present invention also provides DNA polymorphisms that can be used as genetic explanatory factors in the present invention. One such embodiment is a nucleic acid encoding a genetic variant of human dihydrofolate reductase comprising a nucleotide sequence having a 19 base-pair deletion spanning nucleotides 540 to 558 of the nucleotide sequence of SEQ ID NO:41. In a preferred embodiment the nucleic acid has the nucleotide sequence of SEQ ID NO:42.

The present invention also includes primers. One such embodiment is a PCR primer that can be used to distinguish SEQ ID NO:42 from SEQ ID NO:41. Another embodiment is a PCR primer that can be used to distinguish SEQ ID NO:42 from SEQ ID NO:45. These primers are useful for identifying the 19 base-pair deletion spanning nucleotides 540 to 558 of the nucleotide sequence of SEQ ID NO:41 (see Example 2). In a particular embodiment, the PCR primer comprises 8 to 100 and preferably 10 to 50 consecutive nucleotides from the nucleotide sequence of SEQ ID NO:41. In another embodiment the PCR primer comprises 8 to 100 and preferably 10 to 50 consecutive nucleotides from the nucleotide sequence of the complementary strand of SEQ ID NO:41. In still another embodiment the PCR primer comprises 8 to 100 and preferably 10 to 50 consecutive nucleotides from the nucleotide sequence of SEQ ID NO:42. In yet another embodiment the PCR primer comprises 8 to 100 and preferably 10 to 50 consecutive nucleotides from the nucleotide sequence of the complementary strand of SEQ ID NO:42. In still another embodiment the PCR primer comprises 8 to 100 and preferably 10 to 50 consecutive nucleotides from the nucleotide sequence of SEQ ID NO:45. In yet another embodiment the PCR primer comprises 8 to 100 and preferably 10 to 50 consecutive nucleotides from the nucleotide sequence of the complementary strand of SEQ ID NO:45.

In a particular embodiment the PCR primer comprises 8 to 100 and preferably 10 to 50 consecutive nucleotides from nucleotides 350 to 530 of SEQ ID NO:41. In a preferred embodiment of this type, the PCR primer has the nucleotide sequence of CTAAACTGCATCGTCGCTGTG (SEQ ID NO:38). In another particular embodiment the PCR primer comprises 8 to 100 and preferably 10 to 50 consecutive nucleotides from the complementary strand of nucleotides 550 to 850 of SEQ ID NO:41. In preferred embodiment of this type, the PCR primer comprises 8 to 100 and preferably 10 to 50 consecutive nucleotides from the complementary strand of nucleotides 570 to 690 of SEQ ID NO:41. In a particular embodiment, the PCR primer has the nucleotide sequence of AAAAGGGGAATCCAGTCGG (SEQ ID NO:39).

The present invention also provides a nucleic acid that hybridizes under standard hybridization conditions to the nucleotide sequence ACCTGGGCGGGACGCGCCA (SEQ ID NO:40). In another embodiment the nucleic acid hybridizes under standard hybridization conditions to the nucleotide sequence complementary to SEQ ID NO:40. In yet another embodiment the nucleic acid hybridizes under standard hybridization conditions to the nucleotide sequence ACCTGGGCGGGACGCGCC (SEQ ID NO:46). In yet another embodiment the nucleic acid hybridizes under standard hybridization conditions to the nucleotide sequence complementary to SEQ ID NO:46. In a particular embodiment the nucleic acid consists of 9 to 96 nucleotides. In another embodiment the nucleic acid consists of 12 to 48 nucleotides. In still another embodiment the nucleic acid consists of 15 to 36 nucleotides. In a preferred embodiment the nucleic acid consists of 17 to 20 nucleotides.

The present invention also provides a nucleic acid that hybridizes to the nucleotide sequence of SEQ ID NO:41, but not to the nucleotide sequence of SEQ ID NO:42 when the hybridization is performed under identical conditions. In a particular embodiment the nucleic acid comprises the nucleotide sequence of CCCACGGTCGGGGTACCTGGGCGG-GACGCGCCAGGCCGACTCCCGGCGA (SEQ ID NO:29). The present invention further provides a nucleic acid that hybridizes to the nucleotide sequence of SEQ ID NO:42, but not to the nucleotide sequence of SEQ ID NO:41 when the hybridization is performed under identical conditions. In a particular embodiment the nucleic acid comprises the nucleotide sequence of CCCACGGTCGGGGTGGC-CGACTCCCGGCGA (SEQ ID NO:37).

In a related embodiment the present invention provides an isolated nucleic acid that hybridizes to the complementary strand of the nucleotide sequence of SEQ ID NO:42, but not to the complementary strand of the nucleotide sequence of SEQ ID NO:41 when the hybridization is performed under identical conditions. In still another embodiment the nucleic acid hybridizes to the nucleotide sequence of SEQ ID NO:41, but not to the nucleotide sequence of SEQ ID NO:42 when the hybridization is performed under identical conditions. In still another embodiment the nucleic acid hybridizes to the complementary strand of the nucleotide sequence of SEQ ID NO:41, but not to the complementary strand of the nucleotide sequence of SEQ ID NO:42 when the hybridization is performed under identical conditions.

The present invention also provides a nucleic acid that hybridizes to the nucleotide sequence of SEQ ID NO:42, but not to the nucleotide sequence of SEQ ID NO:45 when the hybridization is performed under identical conditions. In a related embodiment the present invention provides an isolated nucleic acid that hybridizes to the complementary strand of the nucleotide sequence of SEQ ID NO:42, but not to the complementary strand of the nucleotide sequence of SEQ ID NO:45, when the hybridization is performed under identical conditions. In still another embodiment the nucleic acid hybridizes to the nucleotide sequence of SEQ ID NO:45, but not to the nucleotide sequence of SEQ ID NO:42 when the hybridization is performed under identical conditions. In still another embodiment the nucleic acid hybridizes to the complementary strand of the nucleotide sequence of SEQ ID NO:45, but not to the complementary strand of the nucleotide sequence of SEQ ID NO:42 when the hybridization is performed under identical conditions.

The present invention also provides for the use of the nucleic acids of the present invention (as well as other nucleic acids which can be used to identify DNA polymorphisms in the alleles of the genes involved in folate, pyridoxine, and/or cobalamin metabolism) in the methods of the present invention for identifying, diagnosing, preventing and/or treating individuals.

In methods of estimating the susceptibility due to genetic or genetic and environmental factors for an individual to have or to develop a developmental disorder or to have offspring that develop a developmental disorder, and for the corresponding methods of generating genetic, or genetic and environmental reference datasets, the present invention provides a step of analyzing nucleic acids and/or proteins from biological samples. In one particular embodiment, the assaying for the presence of the genetic variant of human dihydrofolate reductase having a nucleotide sequence with a 19 base-pair deletion spanning nucleotides 540 to 558 of the nucleotide sequence of SEQ ID NO:41 is included as part of this analysis. This genetic variant of human dihydrofolate reductase becomes a genetic explanatory variable.

Determining if the biological sample contains the genetic variant of human dihydrofolate reductase having a nucleotide sequence with a 19 base-pair deletion spanning nucleotides 540 to 558 of the nucleotide sequence of SEQ ID NO:41 can be performed by any appropriate method including PCR, special PCR, RT PCR, RFLP analysis, SSCP, and FISH.

In addition, all of the nucleic acids of the present invention including cDNA or genomic DNA can be placed into expression vectors operably associated with an expression control sequence. Alternatively, when the nucleic acid is part of an expression control sequence, the nucleic acid and/or the expression control sequence can be placed into an expression vector to control the expression of a coding sequence, such as a reporter gene. Such expression vectors can then be placed into either eukaryotic or prokaryotic host cells and expressed. The host cells comprising the expression vectors are also part of the present invention. In addition, when the nucleic acid includes a coding sequence or a part of a coding sequence, the present invention includes methods of purifying the gene products from the coding sequence or part thereof, and the purified gene products themselves.

Accordingly, it is a principal object of the present invention to provide a method for identifying an individual that is genetically inclined to develop a developmental disorder or disease.

It is a further object of the present invention to provide a method for identifying an individual that is genetically inclined to develop schizophrenia.

It is a further object of the present invention to provide a method for identifying an individual that is genetically inclined to have offspring having a developmental disorder.

It is a further object of the present invention to provide a method of diagnosing schizophrenia.

It is a further object of the present invention to provide a method of treating developmental disorders such as schizophrenia.

It is a further object of the present invention to provide a method for monitoring the treatment of the developmental disorder.

It is a further object of the present invention to provide a method for ameliorating the effect of a defect in folate, pyridoxine or cobalamin metabolism on a fetus due to the genetic or environmental status of a pregnant woman.

It is a further object of the present invention to provide a method of treating a patient who is genetically inclined to develop a developmental disorder such as schizophrenia.

It is a further object of the present invention to provide a method of overcoming a nutritional lack of folate, cobalamin or pyridoxine of a pregnant woman to prevent the development of the corresponding fetus developing a developmental disorder.

Other objects and advantages will become apparent to those skilled in the art from a review of the ensuing description.

These and other aspects of the present invention will be better appreciated by reference to the following drawings and Detailed Description.

BRIEF DESCRIPTION OF THE DRAWINGS

FIG. 1 shows primers for PCR amplification of the dihydrofolate reductase (DHFR) deletion polymorphism region.

FIG. 3 shows the sequences of PCR amplification products in the Region of the DHFR polymorphism region. * is explained in Text, see Example 2.

FIG. 4A is a nucleotide sequence of the wild type human DHFR, (SEQ ID NO:41) from Yang et al., *J. Mol. Biol.* 176:169–187 (1984), GeneBank accession no: X00855. The start codon is in bold. FIG. 4B is the same nucleotide sequence as that of FIG. 4A except the deletion of the 19 nucleotides due to the DHFR deletion polymorphism, (SEQ ID NO:42).

DETAILED DESCRIPTION OF THE INVENTION

Figure 2:
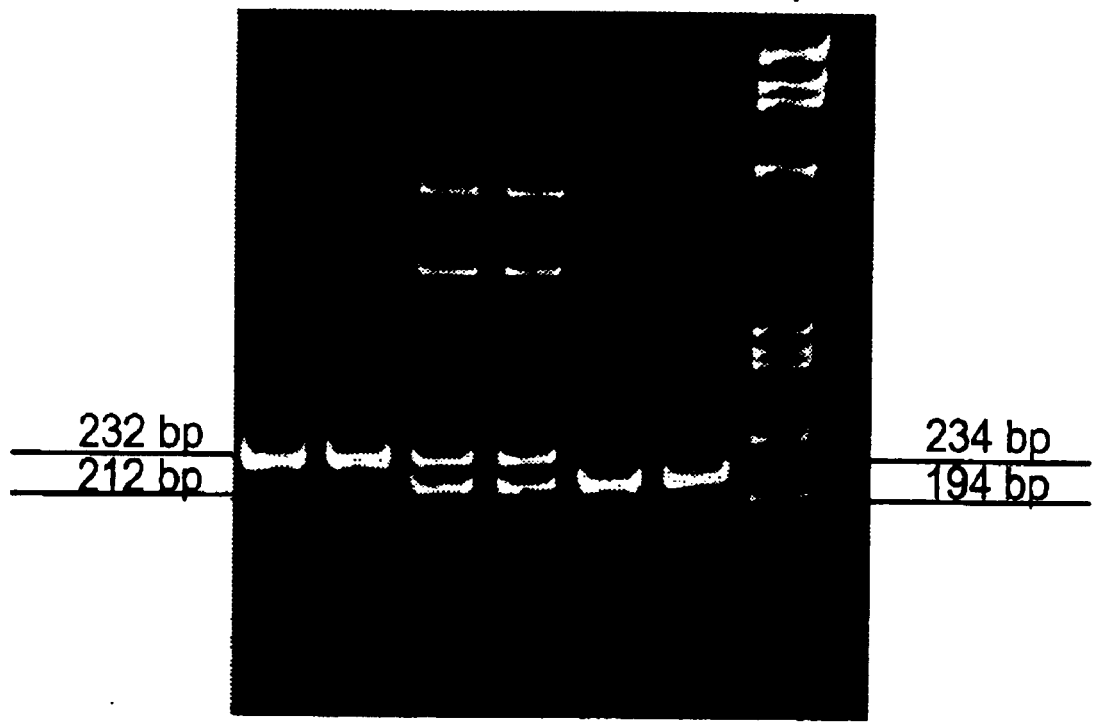
FIG. 2 shows the genotypes of the DHFR 19 basepair deletion by non-denaturing polyacrylamide gel electrophoresis. Lanes 1 and 2 show genotypes 1,1. Lanes 3 and 4 show genotypes 11,2. Lanes 5 and 6 show genotypes 2,2. Lane 7 shows phiX174 RF DNA/HaeIII size markers from BRL Life Technologies.

The present invention in its broadest embodiment provides a method of diagnosing, preventing and/or treating specific physiological/developmental disorders. Such physiological/developmental disorders include schizophrenia, spina bifida cystica, Tourette's syndrome, bipolar illness, autism, conduct disorders, attention deficit disorder, obsessive compulsive disorder, chronic multiple tic syndrome and learning disorders such as dyslexia.

A particular aspect of the present invention provides methodology for diagnosing, preventing and/or treating a developmental disorder such as schizophrenia. Such methodology is premised on the correlation between abnormalities in folate, cobalamin, and/or pyridoxine metabolism in an individual and/or the mother of an individual and the occurrence of the developmental disorder, e.g., schizophrenia in the individual. Further, the present invention provides a framework (i.e., the gene-teratogen model, and the DNA Polymorphism-Diet-Cofactor-Development both of which are described in detail below) which fully explain the rationale for the correlation, though the ultimate usefulness of the methods of the present invention are independent of any particular model.

Within this context, the DNA Polymorphism-Diet-Cofactor-Development model maintains that a developmental disorder such as schizophrenia results in part from developmental brain damage sustained in utero due to maternal dietary deficiency of folate, pyridoxine or cobalamin potentiated by the aggregate effect of minor defects of folate, pyridoxine or cobalamin genes. The maternal damage to the fetus can result in part from insufficiency of the folate, pyridoxine and cobalamin themselves and/or from resulting effects such as immune deficiency and maternal teratogens, e.g. hyperhomocysteinemia. Genes from either parent acting in the fetus may modify these damaging effects as exemplified in the gene-teratogen model, below.

As described herein the present invention can be practiced on a case by case basis, or alternatively, it can be used in the screening of the general population, or within any particular subgroup, such as newborns (as is presently performed in the diagnosis and treatment of hyperphenylalaninemia).

Therefore, if appearing herein, the following terms shall have the definitions set out below.

As used herein a "gene involved in folate, pyridoxine, or cobalamin metabolism" is a gene that encodes a peptide or protein that plays a role in a pathway involved in either folate, pyridoxine, or cobalamin metabolism. An incomplete listing of examples of such proteins is given in Tables 2–7.

As used herein the term "individual" includes a fetus, infant, child, adolescent, and adult. Therefore, as used herein, an individual originates at conception.

As used herein an individual with a susceptibility for "having offspring that develop a developmental disorder" is meant to be indicative of the susceptibility of the offspring of that individual to develop the developmental disorder and is not in any way meant to be indicative of the susceptibility of the individual to have offspring.

The term "proband" as used herein is operationally defined by Table 8 along with the accompanying explanatory information (see, Example 1). For most purposes, the proband can be considered the central figure in the familial analysis, the remaining individuals in the family being designated as "blood relatives". There are three types of probands: (1) an "affected proband" i.e., an individual that is believed to have a developmental disorder; (2) a "control proband" an individual that is believed not to have a developmental disorder; and (3) a "diagnostic proband" i.e., an individual being diagnosed.

As used herein a "blood relative" of an individual is a relative that is related to the individual in a genetic sense. Blood relatives can include mothers, fathers, children, uncles, aunts, brothers, sisters, and grandparents. Preferably a blood relative is a parent, a sibling, or a grandparent. Adopted relatives, step-parents, relatives through marriage and the like are not blood relatives. Therefore, as used herein, the terms "mother", "father", "sibling", "grandparent", "grandfather" and "grandmother" are indicative of blood relationships.

As used herein a "mate of an individual" is a person whose genetic material is combined with that of the individual for the conception of the offspring in question.

As used herein the term "schizophrenia" describes a disorder that is at least partially due to one or more genetic mutations or polymorphisms in one or more genes involved in folate, cobalamin or pyridoxine metabolism in an individual that is schizophrenic and/or to one or more genetic mutations or polymorphisms in one or more genes involved in folate, cobalamin or pyridoxine metabolism in the mother of that individual.

As used herein an individual is "schizophrenic" when the individual displays symptoms that would be accepted by an experienced psychiatrist to merit a diagnosis of schizophrenia. Such a diagnosis is based, at least in part, on the currently evolving guidelines for the diagnosis of schizophrenia which are listed in the successive editions of Diagnostic and Statistical Manual for Mental Disorders, put out by the American Psychiatric Association. The current edition is the DSM, Fourth Edition (1994).

As used herein the terms "spina bifida cystica", "Tourette's syndrome", "bipolar illness", "autism", "conduct disorder", "atention deficit disorder", "obsessive compulsive disorder", "chronic multiple tic syndrome" and "learning disorders" such as "dyslexia" describe disorders which display symptoms that would be accepted by an experienced psychiatrist to merit a diagnosis of that disorder. Such a diagnosis is based, at least in part, on the currently evolving guidelines which are listed in the successive editions of Diagnostic and Statistical Manual for Mental Disorders, put out by the American. Psychiatric Association. The current edition is the DSM, Fourth Edition (1994).

As used herein the term "teratogenic locus" indicates one or more alleles that act in a pregnant woman to cause an intrauterine teratogenic effect on the fetus.

As used herein the terms "specificity locus" or "modifying locus" are used interchangeably and are indicative of one or more alleles that can act during pregnancy and/or after birth to prevent, modify, and/or ameliorate the teratogenic effect of the teratogenic locus.

As used herein a "constellation of genetic mutations" is the set of genetic risk factor mutations that is present in a proband and relatives of the proband. One example of a constellation of genetic mutations is shown in a line of Table 8, below.

As used herein a "risk factor" is a teratogen or substance (including a defective gene) that can lead to a teratogenic effect that is present or suspected of being present in a tissue sample or body fluid of an individual's mother during the individual's gestation and/or present or suspected of being present in a tissue sample or body fluid of the individual.

As used herein a "genetic risk factor" is used interchangeably with the term "genetic explanatory variable" and is a genetic mutation and/or polymorphism that causes or potentially can cause the formation of and/or lead to the development of a risk factor in an individual or the individual's mother during gestation.

As used herein an "environmental risk factor" is used interchangeably with the term "environmental explanatory variable" and is an environmental factor that causes or potentially can cause the formation of and/or lead to the development of a risk factor in an individual or the individual's mother during gestation.

As used herein an "explanatory variable" is either an "environmental explanatory variable" or a "genetic explanatory variable" or the variable defined by their interaction or any combination of the above.

Enzymes whose deficiency may raise plasma homocysteine include methylenetetrahydrofolate reductase (MTHFR), methionine synthase, and folate receptors/transport proteins/binding proteins (as well as all of the proteins listed in Tables 2–7 below).

The current (developmental) model for schizophrenia is that genetic and environmental factors cause brain damage in a fetus that later develops schizophrenia. However, the genetic and environmental factors have not been identified. Also, extensive linkage and association studies have failed to identify genes determining schizophrenia. The reasons usually given for this difficulty include: (i) locus heterogeneity, i.e., more than one gene locus is involved, perhaps many gene loci each with a small effect; (ii) the mode of inheritance of schizophrenia is unknown; and (iii) an additional possible factor is that the frequency of the disease alleles may be high, thus greatly reducing the power of linkage studies.

The DNA Polymorphism-Diet-Cofactor-Development model explains all of these difficulties and at the same time proposes a unified metabolic abnormality. The unified metabolic abnormality is: (a) ENVIRONMENTAL, i.e., due to a folate/cobalamin/pyridoxine deficiency caused by either decreased ingestion or increased requirement during pregnancy; (b) GENETIC, i.e., due to a folate/cobalamin/pyridoxine genetic defect caused by the aggregate effect of multiple mutations of folate/cobalamin/pyridoxine genes each individually having a small effect; and (c) the interaction of the folate/cobalamin/pyridoxine environmental and genetic factors (indicated above) to cause other harmful effects such as maternal teratogens and immune deficiency during gestational development. Different gene loci and different combinations of gene loci will be involved in different patients and different families. The problem of locus heterogeneity is addressed by the hypothesis that the folate/cobalamin/pyridoxine genetic defect is the aggregate effect of multiple mutations of folate/cobalamin/pyridoxine genes each of which have a relatively small effect.

The problem of mode of inheritance is addressed by the gene-teratogen model. The gene-teratogen model describes the special features of genes acting in utero; both teratogenic and modifying of specificity loci may be involved. If these effects are not taken into account, the assignment of affection status in schizophrenia pedigrees is inaccurate. Assignment of affection status is a key element in defining the mode of inheritance for all kinds of linkage mapping. Failure to assign the correct mode of inheritance is another factor that has made the linkage studies very difficult.

Finally, the DNA Polymorphism-Diet-Cofactor-Development model proposes that some of the genetic factors for schizophrenia are common in the population. In fact, subclinical deficiency of folate, pyridoxine, and cobalamin is common in the population and common among pregnant women as well. Pregnancy further increases the requirement for folate, pyridoxine, and cobalamin. Common genetic polymorphisms of folate and cobalamin genes are also known, some of them functional. Common genetic risk factors tend to be functional polymorphisms and/or mutant alleles that individually have small effects. Otherwise, they would be largely eliminated from the population by natural selection and would not be common. High disease allele frequency is yet another factor that greatly diminishes the power of a linkage study.

Besides explaining the difficulties with current linkage studies, the DNA Polymorphism-Diet-Cofactor-Development model explains all of the unusual biological and epidemiological features of schizophrenia: e.g. the decreased amount of gray matter in brain areas, the unusual birth-month effect, the geographical differences in incidence, the socioeconomic predilection, the association with obstetrical abnormalities (low birth weight and prematurity), and the association with famine and viral epidemics. Consistently, genetic linkage and cytogenetic studies in schizophrenia have implicated various chromosome regions, some of them containing folate, pyridoxine, and cobalamin genes including dihydrofolate reductase, thymidylate synthase, and transcobalamin II. The DNA Polymorphism-Diet-Cofactor-Development model predicts that folate, pyridoxine, or cobalamin gene mutations have a high frequency in schizophrenia patients or family members. Furthermore, mothers of schizophrenics are predicted to be particularly susceptible to producing one or more teratogens during pregnancy.

The present invention therefore provides methods for: (a) Diagnostic testing of schizophrenia by identifying a folate, pyridoxine, or cobalamin gene mutation or constellation of mutations in the patient, mother, and father. (b) Prevention of schizophrenia by diagnostic testing in families already affected by schizophrenia or by diagnostic population screening for folate mutations and identifying couples at risk for producing schizophrenic offspring. These pregnancies can be further monitored for risk factors, e.g. dietary folate/pyridoxine/cobalamin, plasma folate/pyridoxine/cobalamin, or red blood cell folate; plasma homocysteine or other teratogens. (c) Therapy for schizophrenia, e.g., treating the pregnant mother with folate, pyridoxine, cobalamin or other agents. The treatment can be monitored at regular intervals to determine the effect of therapy. (d) Presymptomatic treatment of schizophrenia on young children found to be susceptible to schizophrenia by diagnostic testing for folate gene mutations and other risk factors can also be treated with methylfolate or related therapeutic modalities to forestall the appearance of schizophrenia symptoms in adolescence or adulthood.

Empirical studies with methylfolate treatment of schizophrenia have shown modest clinical improvement. The DNA Polymorphism-Diet-Cofactor-Development model gives a rationale for such therapy as well as for intensive testing of related therapeutic modalities. Genetic testing will need to be carried out in such patients to gauge their likelihood of responding to therapy. In addition, the DNA Polymorphism-Diet-Cofactor-Development model gives direction and impetus toward uncovering the mechanism of fetal brain damage leading to schizophrenia.

Diagnostic testing for schizophrenia can involve testing not just the patient, but mother and father as well, for not just one factor but multiple genetic factors. For example, data for two gene loci (both folate-related genes) were used in Example 2. In this case, there were only four explanatory variables for each comparison.

In addition, risk factors appearing only during pregnancy may play a role, e.g. dietary folate which can be further monitored during the pregnancy. In certain instances, genotype data can be used as the sole explanatory variables, particularly in the case when no environmental explanatory variables are known. In such a case, the predicted probabilities will be only for the genetic component of the proband's risk of schizophrenia. In addition, schizophrenia mothers, fathers, and sibs do not necessarily have to come from the same families as the schizophrenia probands, as described in Example 2.

Of course certain genetic factors will turn out to be more common than others. This may simplify testing somewhat. Also some genetic factors may operate chiefly in the mother, while others will operate chiefly in the schizophrenic patient. This may also simplify testing. There are some approaches to assessing risk factors during a past pregnancy, e.g. current dietary history as an indicator of past diet, methionine loading as in indicator of how susceptible a mother is to raising her plasma homocysteine, assessment of other risk factors besides folate metabolism that may affect pregnancy outcome. Procedures including all of these variables are both envisioned and included in the present invention.

Thus the present invention provides a method of diagnosis of schizophrenia. In one aspect of the invention, diagnostic testing for genetic susceptibility to schizophrenia determines the probability that the proband is affected with schizophrenia due to genetic factors. This is carried out by genetic testing of a patient suspected of having schizophrenia and/or whatever informative relatives are available, e.g. mother, father, sibs, or children. The genotypes of certain folate and/or cobalamin and/or pyridoxine gene mutations or constellation of mutations (folate and/or cobalamin and/or pyridoxine gene mutations) are determined for each individual.

Since the abnormal phenotype of schizophrenia can be determined by both genetic and environmental factors and since other genetic factors besides folate/cobalamin/pyridoxine gene mutations may be involved, the presence of folate/cobalamin/pyridoxine gene mutations may be neither necessary nor sufficient to cause schizophrenia. Thus, an unaffected individual may have the same genetic risk factors as an affected individual but may lack sufficient environmental factors to cause the abnormal clinical disease. Also, an affected individual may lack folate/cobalamin/pyridoxine gene mutations but may have other related or non-related genetic risk factors that caused the schizophrenia.

Therefore folate/cobalamin/pyridoxine gene mutations are used as explanatory variables (genetic risk factors) to calculate the predicted probability that an individual has genetic susceptibility to schizophrenia due to these mutations. Genetic variation can be expected to account for approximately about half of the risk of developing schizophrenia since the concordance rate in identical twins has been estimated to be about 50%. The other half of the risk results from environmental factors due to their different positions in the uterus and to differences in the blood supply. The use of environmental factors as additional explanatory variables enhances this probability calculation, although this environmental data is more difficult to gather. Together, using both genetic and environmental explanatory variables, the predicted probability that an individual is schizophrenic may approach 1.0.

One likely situation for the use of the present methodology is in the diagnosis of a patient that has developed a psychosis. In such a case, the clinician is likely to be interested in determining the probability that this individual has schizophrenia. The number of blood relatives (preferably first degree relatives) of the patient-to-be diagnosed, both unaffected and affected, could then be determined. The number of these who would contribute a blood sample for analysis, for example, could then be ascertained. It is preferable that the patient-to-be-diagnosed also contributes a blood sample, however in certain situations, this may not be an option. The availability of dietary and epidemiological information for environmental explanatory variables, especially from the patient and the mother, can also ascertained. Of course all relevant legal and ethical rules should be followed regarding informed consent for the genetic testing.

Biological samples such as tissue or fluid samples (e.g., 7 ml of blood in an EDTA-containing vacutainer, see Example 2, below), and obtainable environmental data from the patient and family members are then collected. DNA is extracted from the sample and genotypes for alleles of folate and/or cobalamin and/or pyridoxine genes are determined.

The methods for genotyping depend upon the specific genetic markers used as explanatory variables. The methods for allele determination for two genetic markers are discussed in the Examples below.

Data of the genetic and environmental explanatory variables for the patient-to-be-diagnosed (proband) and participating family members are added to a reference data set preferably consisting of well-defined schizophrenia probands and family members, and control probands, and family members for whom data is available for many explanatory variables. As an approximation the control probands themselves also can be used as the controls for each proband family member class as shown in Example 2, below. Thus, as an approximation the control probands can be used as controls for the affected probands; and/or separately for the mothers of affected probands; and/or separately for the fathers of affected probands, etc. Another example of a use of the control probands is in the evaluation and/or analysis of a particular diagnostic proband. In this case, the approximation is obtained by adding the diagnostic proband to the group of affected probands and control probands.

A model is then created consisting of the explanatory variables actually available from specific patient-to-be diagnosed and family members participating in the testing. This new combined data set (reference data set and data from patient-to-be-diagnosed with participating family members) is analyzed by binary logistic regression (e.g., using a statistical software package such as the SAS System embodied in Example 1 below, though other programs may be used) for the model chosen giving the predicted probability that a proband is affected with schizophrenia for all of the probands including the patient-to-be-diagnosed.

In a particular embodiment the model is modified and the goodness of fit for the patient-to-be-diagnosed is checked. The predicted probability that the patient-to-be-diagnosed has schizophrenia is compared with a classification table generated from the model used to determine the likelihood of false positives and false negatives.

The predicted probability that the patient-to-be-diagnosed is affected with schizophrenia, with the likelihood of false positive or false negative result, can then be forwarded to the clinician.

The methods for determining an individual's risk for developing schizophrenia taught by the present invention can be used in a variety of settings. For example, the present invention also provides a therapy for schizophrenia Empirical studies with methylfolate treatment of schizophrenia have shown modest clinical improvement. The DNA Polymorphism-Diet-Cofactor-Development model provides a rationale for such therapy as well as for intensive testing of related therapeutic modalities, e.g. other cofactors such as cobalamin or pyridoxine. In addition, the DNA Polymorphism-Diet-Cofactor-Development model gives direction and impetus toward uncovering the mechanism of fetal brain damage leading to schizophrenia. Of course such therapy also can be provided on a case by case basis in order to gauge the likelihood of the patient of responding to such therapy, with the methodology for diagnosis of the present invention enabling the skilled practitioner to assess that likelihood.

In addition, the present invention provides a method of identifying individuals that are likely to be aided by presymptomatic treatment for schizophrenia. For example, young children found to have a high risk for susceptibility to schizophrenia by diagnostic testing can be treated with methylfolate or related therapeutic modalities to forestall the appearance of schizophrenia symptoms in adolescence or adulthood. The present invention further provides methodology for diagnostic testing for specific families already affected by schizophrenia.

The present invention further provides methodology for population screening for folate/cobalamin/pyridoxine mutations to help identify couples at risk for producing schizophrenic offspring. Subsequent or concurrent pregnancies can then be monitored for environmental risk factors, and treated with folate, cobalamin, pyridoxine or other agents and monitored at intervals for the effect of therapy. Such monitoring can include measuring levels of folate, cobalamin, pyridoxine or homocysteine in a particular tissue and/or fluid sample, such as blood.

Since schizophrenia is a developmental disorder, it is likely that these same risk factors discussed here for schizophrenia could play a role in other developmental disorders including spina bifida cystica, Tourette's syndrome, learning disorders including dyslexia, conduct disorder, attention-deficit hyperactivity disorder, bipolar illness, autism, and obsessive-compulsive disorder. Interestingly, the mode of inheritance of these disorders, like that of schizophrenia, has been difficult to determine despite the fact that a genetic component to the etiology of each has been documented. Therefore, methodology analogous to that exemplified herein for schizophrenia can be readily adapted for diagnosing and/or treating other such developmental disorders.

Nucleic Acids

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994)].

A "nucleic acid molecule" refers to the phosphate ester polymeric form of ribonucleosides (adenosine, guano sine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA—DNA, DNA-RNA and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules including restriction fragments, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. High stringency hybridization conditions correspond to 50% formamide, 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids, the GC percentage, and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–10.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid (e.g., a nucleotide probe or primer such as a PCR or RT-PCR primer) is at least about 12 nucleotides; preferably at least about 18 nucleotides; and more preferably the length is at least about 27 nucleotides; and most preferably at least about 36 nucleotides. Specific probes and primers that can be used to distinguish specific variants of the nucleic acids encoding the proteins involved in folate, pyridoxine, and/or cobalamin metabolism are also part of the present invention.

Such nucleotide probes and primers can be labeled or used to label complementary DNA (where appropriate) by any number of ways well known in the art including using a radioactive label, such as $^3H$, $^{14}C$, $^{32}P$, or $^{35}S$, a fluorescent label, a boron label [U.S. Pat. No. 5,595,878, Issued Jan. 21, 1997 and U.S. Pat. No. 5,876,938, Issued Mar. 2, 1999 which are incorporated by reference in their entireties], and enzymatic tags such as urease, alkaline phosphatase or peroxidase. In the case of enzyme tags, colorimetric indicator substrates are known which can be employed to provide a means visible to the human eye or spectrophotometrically, to identify specific hybridization with complementary nucleic acid-containing samples.

In a specific embodiment, the term "standard hybridization conditions" refers to a $T_m$ of 55° C., and utilizes conditions as set forth above e.g., 5×SSC. In a preferred embodiment, the $T_m$ is 60° C.; in a more preferred embodiment, the $T_m$ is 65° C.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A "signal sequence" is included at the beginning of the coding sequence of a protein to direct the protein to a particular site/compartment in the cell such as the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

Identification of Genetic Mutations

A biological sample can be obtained from an individual and/or a blood relative of the individual, and from appropriate controls, using a sample from any body component including tissue punches, body fluids, and hair, as long as the biological sample contains nucleic acids and/or proteins/peptides. Thus the DNA, mRNA, proteins or peptides of the biological sample can be used to identify mutations and/or variants in genes involved in folate, pyridoxine, or cobalamine metabolism. The present invention therefore includes methods of detecting and quantifying these nucleic acids and/or proteins/peptides that can be used to identify genetic risk factors.

In a particular embodiment the DNA is extractable. A particularly useful source of DNA is blood. For example, 2.5–40 mls of blood can be collected in a vacutainer containing EDTA. The blood sample is placed on ice and then centrifuged to separate plasma, red cells, and buffy coat. The separated fractions are then frozen at −80° C.

The DNA can be isolated from the buffy coat by a number of procedures well known in the art including using a QIAmp column DNA extraction procedure or the QIAGEN Genomic-tip method. The isolated DNA can be digested with a series of restriction enzymes, for example, and then the digested products can be hybridized with one or more particular nucleic acid probes designed from a particular gene to identify the gene and preferably to test for particular genetic mutations.

Preferably the genomic DNA can be amplified by PCR using appropriate primer pairs such as the primer pairs for the MTHFR or DHFR genes which were used in the Example below. The PCR amplified product can be sequenced directly, or alternatively be digested with one or more appropriate restriction enzymes. The resulting digested products can be separated e.g., by column chromatography, or preferably by polyacrylamide or agarose gel electrophoresis. The isolated digestion products can be compared e.g., by previously determined restriction maps, and/or alternatively, the digestion products can be sequenced directly. Alternatively, as in the case of DHFR, genetic polymorphisms can be detected through the use of restriction enzymes.

Although a restriction map of a gene is sufficient for the employment of the methods disclosed herein, in preferred embodiments the nucleotide sequences of the genes used in the testing steps are known. To this end a large sampling of such sequences are provided in Tables 2–7. (These sequences may also be used in the design of restriction maps.) Thus, initially each gene whether used separately or used in a constellation of genes is characterized by the sequencing of the wild type gene, preferably including the coding regions, introns, control sequences, and other non-coding regions. In addition, mutations of such genes found in the general population can also be characterized. With the recent advances in the sequencing of the human genome the present invention contemplates that additional sequence information will become publicly available, particularly with regard to mutations in relevant introns, and control sequences etc. which are not available in cDNA libraries. Such sequence information is fully envisioned to be incorporated into the on-going compilations of relevant DNA sequence databases of the present invention, as well as for its parallel use in the general methodology described herein. Thus DNA or mRNA or cDNA made from the mRNA can be used to identify mutations and/or variants in genes involved in folate, pyridoxine, or cobalamine metabolism.

There are many methods currently known in the art to identify variant/mutant DNA, all of which may be used in the present invention. Such methods include but in no way are limited to direct sequencing, array sequencing, matrix-assisted laser desorption/ionization time-of-fight mass spectrometry (Malditof) [Fitzgerald et at., *Ann. Rev. Biophy. Biomol. Struct.* 24:117–140 (1995)]; Polymerase Chain Reaction "PCR", reverse-transcriptase Polymerase Chain Reaction "RT-PCR", RNAase protection assays. Array quantitation e.g., as commercially provided by Affymetrix, Ligase Chain Reaction or Ligase Amplification Reaction (LCR or LAR), Self-Sustained Synthetic Reaction (3SR/NASBA). Restriction Fragment Length Polymorphism (RFLP), Cycling Probe Reaction (CPR), Single-Strand Conformation Polymorphism (SSCP), heteroduplex analysis, hybridization mismatch using nucleases (e.g., cleavase), Southern, Northerns, Westerns, South Westerns, ASOs, Molecular beacons, footprinting, and Fluorescent In Situ Hybridization (FISH). Some of these methods are briefly described blow.

PCR is a method for increasing the concentration of a segment of target sequence in a mixture of genomic DNA without cloning or purification. PCR can be used to directly increase the concentration of the target to an easily detectable level. This process for amplifying the target sequence involves introducing a molar excess of two oligonucleotide primers which are complementary to their respective strands of the double-stranded target sequence to the DNA mixture containing the desired target sequence. The mixture is denatured and then allowed to hybridize. Following hybridization, the primers are extended with polymerase so as to form complementary strands. The steps of denaturation, hybridization, and polymerase extension can be repeated in order to obtain relatively high concentrations of a segment of the desired target sequence. The length of the segment of the desired target sequence is determined by the relative positions of the primers with respect to each other, and, therefore, this length is a controllable parameter. Because the desired segments of the target sequence become the dominant sequences (in terms of concentration) in the mixture, they are said to be "PCR-amplified." [Mullis (U.S. Pat. No. 4,683,195) and Mullis et al. (U.S. Pat. No. 4,683,202)].

In Ligase Chain Reaction or Ligase Amplification Reaction (LCR or LAR) four oligonucleotides, two adjacent oligonucleotides which uniquely hybridize to one strand of target DNA, and a complementary set of adjacent oligonucleotides, which hybridize to the opposite strand are mixed and DNA ligase is added to the mixture. Provided that there is complete complementarity at the junction, ligase will covalently link each set of hybridized molecules. Importantly, in LCR, two probes are ligated together only when they base-pair with sequences in the target sample, without gaps or mismatches. Repeated cycles of denaturation, hybridization and ligation amplify a short segment of DNA. [Barany, Proc. Natl. Acad. Sci., 88:189 (1991); Barany, PCR Methods and Applie., 1:5 (1991); and Wu and Wallace, Genomics 4:560 (1989)] LCR has also been used in combination with PCR to achieve enhanced detection of single-base changes. Segev, PCT Public. No. WO9001069 A1 (1990).

Self-Sustained Synthetic Reaction (3SR/NASBA) is a transcription-based in vitro amplification system [Guatelli et al., *Proc. Natl. Acad. Sci.,* 87:1874–1878, 7797 (1990); Kwok et al., *Proc. Natl. Acad. Sci.,* 86:1173–1177) that can exponentially amplify RNA sequences at a uniform temperature. The amplified RNA can then be utilized for mutation detection (Fahy et al., *PCR Meth. Appl.,* 1:25–33 (1991). In this method, an oligonucleotide primer is used to add a phage RNA polymerase promoter to the 5' end of the sequence of interest. In a cocktail of enzymes and substrates that includes a second primer, reverse transcriptase, RNase H, RNA polymerase and ribo- and deoxyribonucleoside triphosphates, the target sequence undergoes repeated rounds of transcription, cDNA synthesis and second-strand synthesis to amplify the area of interest.

RFLP can be used to detect DNA polymorphisms arising from DNA sequence variation. This method consists of digesting DNA with one or more restriction endonucleases (e.g., EcoRI) and analyzing the resulting fragments by means of Southern blots [Southern, E., *Methods in Enzymology,* 69:152 (1980)], as further described by Botstein, et al., *Am. J. Hum. Genet.,* 32:314–331 (1980) and White, et al., *Sci. Am.,* 258:40–48 (1988). Since a DNA polymorphism may create or delete a restriction site, the length of the corresponding restriction fragment with any given restriction enzyme could change. Once a difference in a restriction fragment length is identified it can be used to readily distinguish a particular polymorphism from the wild type DNA. Mutations that affect the recognition sequence of the endonuclease will preclude enzymatic cleavage at that site, thereby altering the cleavage pattern of that DNA. DNAs are compared by looking for differences in restriction fragment lengths. A technique for detecting specific mutations in any segment of DNA is described in Wallace, et al., [*Nucl. Acids Res.,* 9:879–894 (1981)]. It involves hybridizing the DNA to be analyzed (target DNA) with a complementary, labeled oligonucleotide probe. Due to the thermal instability of DNA duplexes containing even a single base pair mismatch, differential melting temperature can be used to distinguish target DNAs that are perfectly complementary to the probe from target DNAs that differ by as little as a single nucleotide. In a related technique, described in Landegren, et al., *Science,* 41:1077–1080 (1988), oligonucleotide probes are constructed in pairs such that their junction corresponds to the site on the DNA being analyzed for mutation. These oligonucleotides are then hybridized to the DNA being analyzed. Base pair mismatch between either oligonucleotide and the target DNA at the junction location prevents the efficient joining of the two oligonucleotide probes by DNA ligase.

When a sufficient amount of a nucleic acid to be detected is available, there are advantages to detecting that sequence directly, instead of making more copies of that target, (e.g., as in PCR and LCR). Most notably, a method that does not amplify the signal exponentially is more amenable to quantitative analysis. Even if the signal is enhanced by attaching multiple dyes to a single oligonucleotide, the correlation between the final signal intensity and amount of target is direct. Such a system has an additional advantage that the products of the reaction will not themselves promote further reaction, so contamination of lab surfaces by the products is not as much of a concern. Traditional methods of direct detection including Northern and Southern blotting and RNase protection assays usually require the use of radioactivity and are not amenable to automation. Recently devised techniques have sought to eliminate the use of radioactivity and/or improve the sensitivity in automatable formats.

One such example is the Cycling Probe Reaction (CPR) [Duck et al., BioTech., 9:142 (1990)]. CPR, uses a long chimeric oligonucleotide in which a central portion is made of RNA while the two termini are made of DNA. Hybridization of the probe to a target DNA and exposure to a thermostable RNase H causes the RNA portion to be digested. This destabilizes the remaining DNA portions of the duplex, releasing the remainder of the probe from the target DNA and allowing another probe molecule to repeat the process. The signal, in the form of cleaved probe molecules, accumulates at a linear rate. While the repeating process increases the signal, the RNA portion of the oligonucleotide is vulnerable to RNases that may carried through sample preparation.

Single-Strand Conformation Polymorphism (SSCP) is based on the observation that single strands of nucleic acid can take on characteristic conformations in non-denaturing conditions, and these conformations influence electrophoretic mobility. [Hayashi, *PCR Meth. Appl.,* 1:34–38, (1991). The complementary strands assume sufficiently different structures that one strand may be resolved from the other. Changes in sequences within the fragment will also change the conformation, consequently altering the mobility and allowing this to be used as an assay for sequence variations (Orita, et al., *Genomics* 5:874–879, (1989). The SSCP process involves denaturing a DNA segment (e.g., a PCR product) that is labeled on both strands, followed by slow electrophoretic separation on a non-denaturing polyacrylamide gel, so that intra-molecular interactions can form and not be disturbed during the run. This technique is extremely sensitive to variations in gel composition and temperature.

In Fluorescent In Situ Hybridization (FISH), specific probes are designed which can readily distinguish the wild-type gene from the variant/mutant gene. Such methodology allows the identification of a variant/mutant gene through in situ hybridization (U.S. Pat. No. 5,028,525, Issued Jul. 2, 1991; U.S. Pat. No. 5,225,326, Issued Jul. 6, 1993; and U.S. Pat. No. 5,501,952, Issued Mar. 26, 1996. FISH does not require the extraction of DNA. In addition, procedures for separating fetal blood cells from maternal blood cells are well known in the art allowing the fetus and the mother to be analyzed from the same body fluid sample (see U.S. Pat. No. 5,629,147, Issued May 13, 1997).

Similarly, antibodies raised against specific mutations and/or variants in the gene products of the genes involved in folate, pyridoxine, or cobalamine metabolism can be used to identify specific polymorphisms. Alternatively, antibodies raised against the wild type proteins can be used to detect and/or quantify the amount of wild type protein present in a given biological sample. In the case in which cross-reacting protein isn't synthesized by the cells of an individual, or is synthesized in significantly lower amounts than those of control subjects, such determinations can be used to identify a genetic risk factor. In addition, these antibodies can be used in methods well known in the art relating to the localization and activity of the gene products, e.g., for Western blotting, imaging the proteins in situ, measuring levels thereof in appropriate physiological samples, etc. using any of the detection techniques known in the art. Furthermore, such antibodies can be used in flow cytometry studies, in immunohistochemical staining, and in immunoprecipitation which serves to aid the determination of the level of expression of a protein in the cell or tissue.

In the particular instance when the gene product is an enzyme, e.g., dihydrofolate reductase, the enzymatic activity of a biological sample can be indicative of the presence of a genetic risk factor. In a particular embodiment, a decrease in an enzyme activity that is associated with folate, pyridoxine, or cobalamine metabolism can be indicative of the presence of the genetic risk factor. Such assays can be performed on multiple samples such as on a microplate reader [Widemann et al., Clin Chem. 45:223–228 (1999)].

Model 1
The Gene-Teratogen Model for the Inheritance Pattern of Certain Developmental Disorders Introduction It has long been known, e.g. from extensive studies of exogenous teratogens in inbred mice [Finnell and Chernoff, Gene-teratogen interactions: an approach to understanding the metabolic basis of birth defects, In Pharmacokinetics in Teratogenesis, Vol. II:97–109 *Experimental Aspects In Vivo and In Vitro,* CRC Press, Inc, Boca Ratan, Fl. (1987)], that teratogens may be influenced by genetic factors. It is less well known that the same gene defect may cause different clinical disorders depending upon whether the metabolic effect of the gene defect is exerted during gestation in utero or during postnatal life. However, the consequences of gene-teratogen interactions in human pedigrees have not been extensively explored, especially the consequences for the use of linkage mapping to identify an unknown gene acting in utero to cause a developmental disorder. A number of common human developmental disorders have been shown to have a genetic component to their etiology. However, for certain developmental disorders, the mode of inheritance has been difficult to determine and linkage studies have met with unexpected difficulties or have achieved limited success. These developmental disorders include spina bifida cystica [Chatkupt, *Am J Med Genet,* 44:508–512 (1992)], Tourette's syndrome & related disorders, e.g. obsessive-compulsive disorder and chronic multiple tics syndrome [Pauls, *Adv Neurol,* 58;151–157 (1992); McMahon et al., *Adv Neurol,* 58:159–165 (1992); Heutink et al., *Am J Hum Genet,* 57:465–473 (1995); Grice et al., *Am J Hum Genet,* 59:644–652 (1996)], learning disorders, including dyslexia [Lewis, et al., *Behav Genet,* 23:291–297 (1993); Pennington, *J Child Neurol* 10 *Suppl,* 1:S69–S77 (1995)], conduct disorder [Lombroso et al., *J Am Acad Child Adolesc Psychiatry,* 33:921–938 (1994)], attention-deficit hyperactivity disorder [Lombroso et al., *J Am Acad Child Adolesc Psychiatry,* 33:921–938 (1994)], bipolar illness [Baron, *Acta Psychiatr Scand,* 92:81–86 (1995); Benjamin and Gershon, *Biol Psychiatry,* 40:313–316 (1996); Risch and Botstein, *Nature Genet,* 12:351–353 (1996); Jamison and McInnis, *Nature Med,* 2:521–522 (1996); Morell, *Science,* 272:31–32 (1996)], schizophrenia [Owen, *Psychol Med,* 22:289–293 (1992); Cloninger, *Am J Med Genet,* 54:83–92 (1994); Lander and Kruglyak, *Nature Genet,* 11:241–247 (1995); Baron, *Acta Psychiatr Scand,* 92:81–86 (1995); Benjamin and Gershon, *Biol Psychiatry,* 40:313–316 (1996); Baron, *Am J Med Genet,* 67:121–123 (1996)], autism [Lombroso et al., *J Am Acad Child Adolesc Psychiatry,* 33:921–938 (1994)], and obsessive-compulsive disorder in adults [Lombroso et al., *J Am Acad Child Adolesc Psychiatry,* 33:921–938 (1994)]. A recent article [Moldin, *Nature Genet.* 17:127–129 (1997)] has reviewed "The maddening hunt for madness genes."

The present model addresses the question of the mode of inheritance of certain developmental disorders and proposes the "gene-teratogen model." The model suggests that the mode of inheritance of genes acting prenatally may in some cases be fundamentally different from that of genes acting postnatally. Even the same gene acting prenatally may produce a different disorder from that gene acting postnatally. The inheritance pattern in the gene-teratogen model is simple, but from the perspective of the patient with the developmental disorder is neither dominant nor recessive. Some disorders regarded as multifactorial, polygenic, or oligogenic may have this mode of inheritance. In the gene-teratogen model, genetically determined teratogen production by the mother during pregnancy damages the fetus producing the abnormal phenotype of a developmental disorder. The model is illustrated with two types of loci, 1. a teratogenic locus acting in the mother, and 2. a modifying or specificity locus acting in the fetus. Damage by the teratogen is influenced also by environmental factors. The model is interesting because it is simple and because teratogenic loci will be difficult to locate by parametric or non-parametric linkage mapping techniques due to misspecification of the affection status of both mother and affected children. A study design is suggested for identifying teratogenic loci. An example of the gene-teratogen model is the major intrauterine effect seen in offspring of phenylketonuric mothers. Certain developmental disorders whose mode of inheritance has been difficult to determine or whose genetic factors have been difficult to locate are candidates for the gene-teratogen model, including spina bifida cystica, Tourette's syndrome, learning disorders including dyslexia, conduct disorder, attention-deficit hyperactivity disorder, bipolar illness, schizophrenia, autism, and obsessive-compulsive disorder.

The Gene Teratogen Model

The model is described in Table 1 using two kinds of loci: a "teratogenic" locus and a "modifying" or "specificity" locus. The gene-teratogen model requires a teratogenic locus. One or more modifying or specificity loci may or may not be present. Also, two types of phenotypes are defined: 1. the teratogen-induced phenotype; and 2. the teratogenic phenotype, i.e., the phenotype of a mother that produces a teratogenic effect during pregnancy. The two phenotypes are different for the teratogenic locus but are identical for the modifying or specificity loci.

TABLE 1

DIAGRAM OF THE GENE-TERATOGEN MODEL

| Grandparents: | Maternal Grandmother AabbCCdd | Maternal Grandfather AaBbCcdd | Paternal Grandmother AAbbCcDd | Paternal Grandfather AAbbCCdd |
|---|---|---|---|---|
| Parents: | | Mother aaBbCcdd | | Father AAbbCcDd |
| Child: | | Child (fetus) with developmental disorder AabbccDd | | |
| locus A: | | teratogenic locus recessive, acting in the mother to cause intrauterine teratogenic damage to the fetus. | | |
| locus B: | | teratogenic locus, dominant, acting in the mother to cause intrauterine teratogenic damage to the fetus. | | |
| locus C: | | modifying or specificity locus, recessive, acting in the fetus. | | |
| locus D: | | modifying or specificity locus, dominant, acting in the fetus. | | |

The teratogenic locus may be dominant (locus A) or recessive (locus B). This locus acts in the mother during pregnancy to cause an intrauterine teratogenic effect in the fetus. The teratogenic effect may result from the production of an endogenous teratogen, from potentiation of an exogenous teratogen, from a metabolic deprivation or imbalance or from some other mechanism. Only one teratogenic locus is required; both locus A and locus B are shown on the same diagram for simplicity. A specificity or modifying locus may be dominant (locus C) or recessive (locus D). Such a locus acts during pregnancy or after to modify the extent of the developmental damage done by the teratogenic locus or even to prevent or repair the damage. For example, for a teratogen acting at a certain time in development, locus C or D may determine whether brain or kidney is damaged, which structures of the brain are damaged, or whether damage occurs at all.

1. Locus A, recessive teratogenic locus, acting in the mother: The child is the patient with the abnormal phenotype of a specific developmental disorder, while mother, father, and grandparents do not have the abnormal phenotype of that disorder (Table 1). Locus A acts in the mother during pregnancy causing her to produce the teratogenic effect that damages the developing fetus leading to the developmental disorder either in the fetus or postnatally in the child or adult. Since this locus is recessive in action, the mother, a homozygote (aa) for the disease allele, is the genetic "patient." Her abnormal phenotype, the "teratogenic phenotype", is the trait of producing the teratogenic effect during pregnancy. Her fetus, damaged by the teratogenic effect in utero, does develop the teratogen-induced phenotype. However, the fetus is only a heterozygote (Aa) at locus A and thus lacks both the abnormal homozygous genotype at locus A and the abnormal teratogenic phenotype; e.g., if the fetus is a daughter, she will not produce the teratogenic effect later during pregnancy. Thus, the fetus is affected with the developmental disorder but is not the genetic "patient." Locus A, acting through a teratogenic effect, cannot be the only etiological factor for the developmental disorder. If it were, then all pregnancies of an aa mother would have the teratogen-induced phenotype which is not the case. Environmental and/or other genetic factors, are required. An aa father will have the abnormal genotype, but not the abnormal teratogenic phenotype because he could never become pregnant.

2. Locus B, dominant teratogenic locus acting in the mother: The situation is the same as for locus A except that locus B is dominant in action (Table 1). The mother has the abnormal genotype, Bb, and the abnormal teratogenic phenotype. The fetus has the teratogen-induced phenotype but in the instance shown (Table 1) has neither the abnormal genotype, the teratogenic phenotype, nor even a copy of the disease allele. The maternal grandfather shown (Table 1) has the abnormal genotype, Bb, but does not have the teratogenic phenotype because he could never become pregnant.

3. Environmental effects: The teratogenic effect is modified by environmental factors, e.g. maternal dietary factors, infection, or ingestion of teratogen. These environmental factors may interact with locus A or B or may act independently. From the perspective of the fetus later to develop the developmental disorder (teratogen-induced phenotype), intrauterine teratogenic is an environmental not a genetic effect.

4. Modifying or Specificity Loci Acting in the Fetus, Loci C & D: These loci may interact with the teratogenic locus or the environmental factors to increase or decrease their effect, or alternatively could act independently. Such genetic factors may be recessive (locus C) or dominant (locus D). Genotypes and phenotypes of locus C and D behave conventionally with respect to the developmental disorder. For locus C and D, the fetus is with the developmental disorder is now the genetic "patient". Maternal teratogenic in utero is an environmental effect. It is thus possible that the same gene locus could act in part as a teratogenic locus and in part as a modifying or specificity locus.

Discussion

The Example of Phenylketonuria: An example of the gene-teratogen model is the major intrauterine effect in maternal phenylketonuria (PKU). Phenylketonuria itself is a recessive postnatal disorder. Untreated homozygous PKU mothers and fathers both have elevated blood phenylalanine (hyperphenylalaninemia). However, heterozygous offspring of untreated PKU mothers (but not fathers) have an abnormal phenotype. [Koch et al., *Acta Paediatr Suppl,* 407:111–119 (1994); Allen et al., *Acta Paediatr Suppl,* 407:83–85 (1994); Abadie et al., *Archives Pediatr,* 3:489–486 (1996)]. Thus the elevated blood phenylalanine or other metabolite(s) in the mother acts as a teratogen for the fetus. Note that the fetus of an untreated phenylketonuric mother does not have the phenotype of PKU (the "teratogenic phenotype"), but has a different phenotype (the "teratogen-induced phenotype").

Phenylketonurics [Menkes, *Textbook of Child Neurology,* Lea & Febiger, Philadelphia (1990)] are normal at birth and develop a progressive disorder postnatally characterized by vomiting, eczema, seizures (infantile spasms with hypsarrythmia on electroencephalography), and mental retardation. The fetus of an untreated phenylketonuric mother [Menkes, *Textbook of Child Neurology,* Lea & Febiger, Philadelphia (1990)] has a congenital non-progressive disorder of fetal origin characterized by microcephaly, abnormal facies, mental retardation, congenital heart disease, and prenatal and postnatal growth retardation. The PKU phenotype is a postnatal degenerative disorder; the phenotype of the PKU intrauterine effect is a developmental disorder. The teratogenic effect is not dependent upon the fetal genotype, although the fetus is an obligate heterozygote since the mother is a homozygote for phenylketonuria and the father (usually) has the normal genotype. Thus, in phenylketonuria, a mutation at the same gene locus causes two distinct disorders depending upon whether the period of abnormal gene action is prenatal or postnatal. A fetus with the abnormal homozygous genotype who is carried by a heterozygous mother is protected in utero, but develops PKU postnatally. A heterozygous fetus carried by a mother with the abnormal homozygous genotype is damaged in utero when the mother's genotype predominates, but is protected from PKU postnatally by its own genotype.

An Example from Studies in Inbred Mice: Finnell and Chernoff [Gene-teratagen interactions: an approach to understanding the metabolic basis of birth defects, In Pharmacokinetics in Teratogenesis, Vol. II:97–109 *Experimental Aspects In Vivo and In Vitro,* CRC Press, Inc, Boca Ratan, Fl. (1987)] have reviewed a group of elegant experiments in inbred mice documenting that differences in susceptibility to exogenous teratogens can be regarded as a genetic trait that is determined by susceptibility or liability genes of either the maternal or fetal genotype [Finnell and Chernoff, Gene-teratagen interactions: an approach to understanding the metabolic basis of birth defects, In Pharmacokinetics in Teratogenesis, Vol. II:97–109 *Experimental Aspects In Vivo and In Vitro,* CRC Press, Inc, Boca Ratan, Fl. (1987)]; Finnell et al., *Am J. Med. Genet.* 70:303–311 (1997); Bennett et al., *Epilepsia* 38:415–423 (1997)]. For example, sensitivity to acetazolamine-induced ectrodactyly is determined by the presence of three genes, and the fetus must be homozygous for the recessive allele at all three loci in order to express the malformation. However, the inbred mouse models used do not mirror the human situation in at least three respects. First, the human population is an outbred population compared to these inbred mouse models. Consequently, the relevant genotypes may be highly variable among members of different families. Second, the inbred mouse experiments address the question of exogenous rather than endogenous teratogens. Third, the inbred mouse studies rely upon known or candidate susceptibility loci, whereas in humans, the problem has been to locate and identify disease unknown loci largely by using linkage mapping techniques.

Implications for Linkage Mapping:

Teratogenic Locus (LocusA or B): The gene-teratogen model has major implications for linkage mapping done with either parametric or non-parametric methods. The problem for both methods is incorrect assignment of affection status. In the lod score method, a genetic model of the disease is constructed and an affection status is assigned to each member of the pedigree. If the genetic model specified is wrong, the linkage results may be falsely positive or falsely negative [Terwilliger and Ott, *Handbook of Human Genetic Linkage,* Johns Hopkins Univ. Pr., Baltimore (1994)].

In developmental disorders resulting from the gene-teratogen model, the phenotype assignment for lod score analysis will be incorrect. The patient with the developmental disorder will be assigned the affected phenotype, whereas the patient is actually affected only for the teratogen-induced phenotype, but is unaffected for the teratogenic phenotype. Likewise, the mother will be assigned the unaffected phenotype for linkage analysis. Actually, she is unaffected only for the teratogen-induced phenotype, but is affected for the teratogenic phenotype. Lod scores should increase when phenotype assignments have been corrected. However, apparently dominant inheritance may in fact turn out to be pseudodominant if the mutant allele is common in the population. For non-parametric analysis, a similar misassignment occurs. In the case of affected sib-pairs, the affected sibs will be assigned the affected phenotype. Actually, the sibs are affected only for the teratogen-induced phenotype, but are unaffected for the teratogenic phenotype. The mother will be assigned the unaffected or unknown phenotype. Actually, she is unaffected only for the teratogen-induced phenotype but is affected for the teratogenic phenotype. Thus, the "affected sib-pair" families are likely to turn out to contain only a single sporadic case, since the only individual in the kindred affected with the teratogenic phenotype will be the mother.

For the transmission/disequilibrium test (TDT) [Spielman et al., Am J Hum Genet, 52:506–516 (1993); Ewens- and Spielman, Am J Hum Genet, 57:455–464 (1995)] the patient with the developmental disorder will be assigned the affected phenotype. Actually, the patient will be affected only for the teratogen-induced phenotype but will be unaffected for the teratogenic phenotype. The mother will be assigned the unaffected or unknown phenotype. Actually, she is unaffected only for the teratogen-induced phenotype but is affected for the teratogenic phenotype. The expectation of TDT is that alleles of a linked locus will show distortion from random transmission from mother (or father) to the patient. Since the patient is unaffected for the teratogenic phenotype, no transmission distortion from mother (or father) to child will be observed. Transmission distortion for alleles of a teratogenic locus will in fact occur from the mother's parents to the mother, the actual patient for the teratogenic phenotype. But this will not be looked for because the phenotypes have been wrongly assigned. In addition, grandparents of the patients with the developmental disorder have probably not had DNA collected. Therefore, for the TDT, negative results may occur for disease alleles of a teratogenic locus because incorrect phenotype assignments will have been made. When correct phenotype assignments have been made, transmission distortion to the mother from her parents should be expected for disease alleles of a teratogenic locus. Analogous misassignments are made in allelic association and haplotype relative-risk analyses [Falk and Rubinstein, Ann Hu, Genet, 51:227–233 (1987); Terwilliger and Ott, Hum Hered, 42:337–346 (1992); Thomson, Am J Hum Genet, 57:487–498 (1995)].

Modifying or Specificity Loci (Locus C and/or D): Since these loci behave in a conventional fashion, the phenotype assignments will be correct. Consequently, genes identified by conventional parametric or non-parametric linkage studies are likely to be modifying or specificity loci. An important question for linkage mapping is the relative contribution to the abnormal phenotype of the developmental disorder made by the teratogenic locus versus that of a modifying or specificity locus. If the effect of a teratogenic locus is small, then loci identified by conventional linkage studies will be specificity or modifying loci and the mode of inheritance will be Mendelian or multifactorial. If a teratogenic locus makes a major contribution to phenotype, then linkage mapping studies will not give a consistent answer and the mode of inheritance will be difficult to determine.

The presence of a teratogenic locus may be suspected if the maternal contribution to phenotype is different from or greater than the paternal contribution. For example, the mother's relatives of spina bifida infants more frequently have affected children than the father's relatives. Suggested explanations for this observation have been mitochondrial inheritance, maternal effect, or genomic imprinting [Chatkupt, Am J Med Genet, 44:508–512 (1992)]. The operation of a teratogenic locus is another explanation and is itself a form of maternal effect. For a recessive teratogenic locus, the mother's sisters would be at greatest risk of having offspring with the teratogen-induced phenotype.

Implications for Definition of Phenotype: All the pregnancies of a mother with the teratogenic phenotype are at risk for the developmental disorder, the teratogen-induced phenotype. Yet only a few of the fetuses will be affected by the developmental disorder because of the action of environmental factors and/or the modifying or specificity loci. The action of the environmental factors is fully quantitative: depending upon the amplitude of the environmental effect, a mild, moderate, or severe teratogen-induced phenotype may result. In addition, the environmental factor may act at different times in fetal development producing qualitatively different phenotypes. Thus, quantitatively or qualitatively different teratogen-induced phenotypes may result from pregnancies of the same mother with the teratogenic phenotype. In addition, the action of the modifying or specificity loci may produce quantitatively or qualitatively different phenotypes in offspring of the same couple. Such different phenotypes may be diagnostically classified as different disorders. This may complicate attempts at associating specific loci with a specific teratogen-induced phenotype. All of the teratogen-induced phenotypes resulting from pregnancies of a mother with the teratogenic phenotype modified only by environmental factors are genetically indistinguishable. However, such teratogen-induced phenotypes affected also by the various modifying or specificity loci segregating among the offspring of a single couple are only partially genetically related.

Methods to Identify Teratogenic Loci: One effective approach to finding a putative teratogenic locus is to carry out non-parametric linkage studies of families consisting of a patient affected with the developmental disorder, the patient's two (unaffected) parents, and the patient's four (unaffected) grandparents (Table 1). In such a family, the mother is the genetic patient but the other family members are not. Now, the mother's nuclear family (the mother and her parents) is compared with the father's nuclear family (the father and his parents). In a haplotype relative risk study, the disease allele(s) of the teratogenic locus will occur more frequently in the mother compared with other alleles of her parents; the disease allele(s) of the teratogenic locus will not occur more frequently in the father compared with other alleles of his parents. In a transmission/disequilibrium test, transmission distortion will be seen for the disease allele(s) of a teratogenic locus in the mothers nuclear family but not in the father's nuclear family. In an allelic association study, the disease allele will occur more frequently in mothers, patients (with the developmental disorder), and patient's sibs (both affected and unaffected) than in unrelated control individuals. Disease allele frequency in fathers will not be distinguishable from that in control individuals.

Certain developmental disorders with a genetic component to etiology, whose mode of inheritance has been difficult to determine or whose genetic factors have been difficult to locate, including those mentioned earlier, are candidates for the gene-teratogen model.

MODEL 2

The DNA Polymorphism-Diet-Cofactor-Development Hypothesis for Schizophrenia and other Developmental Disorders Folate metabolism is complex. At least 30 gene loci are involved in absorption, transport, and metabolism of folate, and these are regulated by additional gene loci. Any of these is potentially a genetic risk factor for schizophrenia, although MTHFR and DHFR are particularly good candidates. Likewise, genes encoding proteins involved in the pathways of other vitamin-cofactors may be genetic risk factors.

Two cofactors that may be of particular potential importance are cobalamin and pyridoxine. Cobalamin is relevant because its metabolism is closely intertwined with that of folate. For example, cobalamin is required for the activity of methionine synthase (MTR), a folate-related enzyme. Decreased cobalamin can affect folate metabolism through the folate trap. Pyridoxine is relevant because the pyridoxine-dependent enzyme cystathionine beta-synthase (CBS), along with the cobalamin-dependent enzyme MTR and folate pathways including MTHFR and DHFR all participate in catabolism of homocysteine, an amino acid that is suspected of being a teratogen during pregnancy. Also, kynureninase, an important enzyme affecting niacin metabolism and serotonin synthesis is pyridoxine-dependent. Therefore, mutations of the genes encoding such proteins, especially common polymorphisms, could play a role in the cause of schizophrenia.

Since folate, cobalamin, and pyridoxine are all dietary constituents, the dietary content of these cofactors could be lead to an "environmental" generation of a risk factor for schizophrenia. In addition genes encoding proteins involved in folate, cobalamin, and pyridoxine metabolism and catabolism could be genetic risk factors for schizophrenia. Thus, the cofactors and the proteins involved in pathways relevant to these cofactors can potentially have either or both environmental and genetic effects on the susceptibility of an individual on schizophrenia.

Since the genetic aspect of schizophrenia differs so profoundly from other disorders which have been identified by linkage mapping techniques, it is clear that a new model for the genetic connection to schizophrenia is required. Therefore, the DNA Polymorphism-Diet-Cofactor-Development (DDCD) hypothesis, is disclosed herein.

The DDCD hypothesis is that interacting genetic and environmental factors affecting the metabolism of folate, cobalamin, or pyridoxine or all of these, play a role in the etiology of schizophrenia. The genetic effect results from the aggregate effect of multiple mutations that individually, for the most part, have small effects on folate-, cobalamin- or pyridoxine-related genes, some of which will be common in the population, and can act in utero. Environmental factors include dietary folate and cobalamin and pyridoxine. If schizophrenia results from mild deficiency during fetal development of dietary folate, cobalamin, or pyridoxine potentiated by mild genetic susceptibility mutations of genes related to these cofactors and by pregnancy, then this would be difficult to document by linkage mapping techniques. An example of interaction of genetic and environmental factors is that genetic factors are important for incorporating dietary folate; the enzyme dihydrofolate reductase is required for conversion of dietary folate to folinic acid thus allowing dietary folate to enter the body's metabolic pathways. Another example is that folate and cobalamin requirements increase during pregnancy; thus pregnancy could potentiate the effects of mild genetic defects of mother, fetus, or both. Deficiencies of a vitamin are often part of a broader dietary deficiency affecting multiple nutrients in addition to the vitamin being measured.

Locus Heterogeneity: The metabolic pathways of folate, cobalamin, and pyridoxine are complex and related to each other. Multiple gene loci code for the enzymes and transport proteins are required (Tables 2–7). Thus, a defect of folate, cobalamin, or pyridoxine metabolism could result from the aggregate effect of multiple mutations each of relatively small effect interacting with environmental factors. Different individuals might have different combinations of mutations. Such a metabolic defect would be difficult to detect by linkage mapping techniques because of locus heterogeneity.

Alternatively, even if one genetic defect were sufficient to make an individual more susceptible to having schizophrenic offspring, for example, because of the large number of potential genetic factors, and the corresponding importance of environmental factors, elucidation of such an individual genetic defect would still be difficult unless, of course, the genetic defect caused a major effect. The difficulty in elucidating an individual genetic defect is magnified when the genetic factor acts in the mother, and not in the schizophrenic patient.

High Disease Allele Frequency: Numerous mutational variants of folate and cobalamin genes are known. Some of these have functional significance and in addition are sufficiently common in a given population to be regarded as genetic polymorphisms. However, these common alleles are unlikely to have a major harmful effect by themselves, for if they did they would become uncommon in the population in the absence of selection effects, and would likely appear as Mendelian disorders. Thus, the folate, cobalamin, or pyridoxine disease alleles related to schizophrenia would appear to be more likely those of minor deleterious effect or those with harmful effect only in the presence of environmental deficiencies or pregnancy. Such disease genes of high population frequency will be difficult to detect by linkage mapping methods because high disease allele frequency decreases the power of linkage studies [Terwilliger and Ott, Handbook of Human Genetic Linkage, John Hopkins Univ. Press, Baltimore, (1994)].

Developmental Genes: Folate, cobalamin, and pyridoxine defects act prenatally as well as postnatally. Folate, cobalamin, and pyridoxine metabolism are crucial for DNA synthesis and cell division, which are of disproportionate importance during brain development. Some defects of folate, cobalamin, or pyridoxine metabolism elevate blood homocysteine, a toxic and potentially teratogenic substance. Genes acting in the mother to damage the developing fetus, e.g. via the gene-teratogen model (Model 1, above), have a mode of inheritance that is neither dominant nor recessive with respect to the fetus. Attempts to assign a mode of inheritance in this situation will be unsatisfactory because affection status would be incorrectly assigned. The mode of inheritance of a developmental disorder resulting from a teratogenic locus would be regarded as either multifactorial or unknown. This is the situation with schizophrenia whose mode of inheritance is unknown. Use of an incorrect genetic model decreases the power of a linkage studies [Terwilliger and Ott, Handbook of Human Genetic Linkage, John Hopkins Univ. Press, Baltimore, (1994)].

Genes of Folate Metabolism: Folate metabolism is extremely complex [Rosenblatt, In: The Metabolic and Molecular Bases of Inherited Disease, Scriver et al. (eds), New York: McGraw-Hill, pp. 3111–3128 (1995); Mudd et al., In: The Metabolic and Molecular Bases of Inherited Disease, Scriver et al. (eds), New York: McGraw-Hill pp. 1279–1327 (1995)]. At least 30 gene loci (Table 2) have been identified as folate-related. These contribute to folate mediated 1-carbon transfer reactions, binding, transport and metabolism of folate, and other functions. A number of these have been cloned and localized to a chromosomal region (Table 3).

TABLE 2

FOLATE-RELATED GENES/ENZYMES/TRANSPORTERS[a]

| Folate-Related Genes/Enzymes/Tranporters[a] | SEQ ID NO: |
|---|---|
| methylenetetrahydrofolate reductase, MTHFR, MIM 236250 | 1 |
| methionine synthase (methyltetrahydrofolate:L-homocysteine S-methyltransferase), MTR, MIM 156570 | 2 |
| dihydrofolate reductase, DHFR, MIM 126060 | 3 |
| folylpolyglutamate synthase, FPGS, MIM 136510 | 4 |
| folate receptor 1, folate receptor alpha (FOLR1, adult; FR-alpha), MIM 136430 | 5 |
| folate receptor 2, folate receptor beta (FOLR2, fetal; FR-beta), MIM 136425 (a.a.) | 6 |
| folate receptor 2-like (FOLR2L, fetal-like), MIM-none | |
| folate receptor gamma (FR-gamma), MIM 602469 | 7 |
| serine hydroxymethyltrasferase 1, SHMT1, MIM 182144 | 8 |
| methylenetetrahydrofolate dehydrogenase, methenyltetrahydrofolate cyclohydrolase, 10-formyltetrahydrofolate synthetase (trifunctional enzyme, MTHFD), MIM 172460 | 9 |
| serine hydroxymethyltransferase 2, SHMT2, MIM 138450 | 10 |
| thymidylate synthase, TYMS, MIM 188350 | 11 |

TABLE 2-continued

FOLATE-RELATED GENES/ENZYMES/TRANSPORTERS[a]

| Folate-Related Genes/Enzymes/Tranporters[a] | SEQ ID NO: |
|---|---|
| GAR (5-phoshoribosylglycineamide) transformylase, GART, MIM 138440 | 12 |
| reduced folate carrier-1, RFC1. Probably identical to micromolar membrane transport protein, intestinal folate carrier-1 (IFC1), and neutral folate transport protein. MIM 600424 | 13 |
| cystathionie beta-synthase, CBS, MIM 236200 | 14 |
| AICAR (5-phoshoribosyl-5-aminoimidazole-4-carboxamide) transformylase glutamate formiminotransferase, MIM 229100 forminotetrahydrofolate cyclodeaminase 5, 10-methenyltetrahydrofolate synthetase 10-formyltetrahydrofolate dehydrogenase, Mim 600249 glycine cleavage pathway (SHMT plus three enzymes): MIM 238331 | 15 |
| 5, 10-methenyltetrahydrofolate synthetase | 16 |
|     Gly-decarboxylase MIM 238300 | 17 |
|     H-Protein MIM238330 | 18 |
|     T-Protein MIM238310 | 19 |
| cblG (affects function of MTR), MIM 250940 methionine adenosyltransferase 1, MATlA, (ATP:L-methionine S-adenosyltransferase), MIM 250850 pteroyl polyglutamate hydrolase ("conjugase"), form 1 pteroyl polyglutamate hydrolase ("conjugase"), form 2 | 20 |
| NAD-dependent enzyme methylene tetrahydrofolate dehydrogenase cyclohydrolase (a.a.) | 21 |
| methionine adenosyltransferase 2, MAT2A, MIM 601468 | 22 |
| 5-methyltetrahydrofolate-homocysteine methyltransferase reductase (MTRR) MIM 602568; #Variant in MTRR linked to cblE MIM 236270 methyltranferases | 23 |
| S-adenosylmethionine decarboxylase, MIM 180980 | 24 |
| decarboxylated S-adenosylmethionine:putrescine propylaminotransferase or spermidine synthetase (a.a.) | 25 |
| S-adenosylhomocysteine hydrolase,, MIM 180960 betaine-homocysteine methyltransferase dimethylthetin-homocysteine methyltransferase | 26 |
| gamma-cystathionase (L-cystationine cysteine-lyase (deaminating)), MIM 602888 folic acid transport protein, MIM 229050 | 27 |
| | 28 |
| DHFR (exon 6 and 3 'flanking region) | 30 |
| kynureninase | 35 |
| human DHFR, exons 1 and 2 [Chen et al., J. Biol. Chem. 259:3933–3943 (1984)] | 36 |

[a]listed with alternate names, abbreviations, and MIM numbers;
cblE is a phenotype for a particular group of disorders of folate/cobalamin metabolism.
(a.a.) indicates the amino acid sequence

TABLE 3

LOCALIZED GENE LOCI RELATED TO FOLATE METABOLISM

| Gene/enzyme/ transport protein | Location | References |
|---|---|---|
| MTHFR | 1p36.3 | Goyette et al.,(1994); *,** |
| MTR | 1q43 | Cook and Hamerton, (1979); Mellman et al., (1979) ** |
| DHFR | 5q11.2-13.2 | Weiffenbach et al., (1991) Gilliam et al. (1989b) *,** |
| FPGS | 9cen-q34 | Jones and Kao (1984). Walter et al. (1992) *,** |
| MAT | 10q22 | ** |
| FR | 11q13.3-q14.1 | Lacey et al. (1989), Ragoussis et al, (1992); Ratnum et al. (1989); Walter et al. (1992); * |
| | 11q13.3-113.5 | Ragoussis et al, (1992), ** |

TABLE 3-continued

LOCALIZED GENE LOCI RELATED TO FOLATE METABOLISM

| Gene/enzyme/ transport protein | Location | References |
|---|---|---|
| SHMT2 | 12q12-q14 | Garrow et al., (1993); Law and Kao, (1979) * |
| | 12q13 | ** |
| MTHFD | 14q24 | Rozen et al., (1989), Jones et al. (1981), *,** |
| LCCL | 16pter-qter | *,** |
| SHMT1 | 17p11.2 | Garrow et al., (1993) *,** |
| TYMS | 18p11.31.-p11.22 | * |
| | 18p11.32 | Hori et al., (1990); Silverman et al., (1993) |
| SAHH | 20cen-q13.1 | * |
| GART | 21q22.1 | McInnis et al. (1993) Schild et al. (1990) Avrarmopoulos et al. (1993) Go to et al. (1993) *,** |
| RFC1 | 21q22.2-22.3 | Moscow et al., (1995) |
| CBS | 21q22.3 | Munke et al., (1988) | notes: MTHFR = methylenetetrahydrofolate reductase.
MTS = methionine synthase.
DHFR = dihydrofolate reductase.
FPGS = folylpolyglutamate synthase.
MAT = methionine adenosyltransferase, (ATP:L-methionine S-adenosyltransferase).
FR = folate receptor complex: FR-alpha = FOLR1 = folate receptor 1, adult; FR-beta = FOLR2 = folate receptor 2, fetal; FR-gamma; FOLR2L = folate receptor 2-like.
SHMT2 = serine hydroxymethyltransferase 2, mitochondrial.
MTHFD = 5, 10-methylenetetrahydrofolate dehydrogenase, 5, 10-methylenetetrahydrofolate cyclohydrolase, 10-formytetrahydrofolate synthase (trifunctional enzyme).
LCCL = gamma-cystathionase (L-cystathionine cysteine-lyase (deaminating).
SHMT1 = serine hydroxymethyltransferase 1, soluble.
TYMS = thymidyiate synthetase.
SAHH, S-adenosylhomocysteine hydrolase.
GART = phosphoribosylglycineamide formyltransferase.
RFC1 = reduced folate carrier-1 (possibly identical to IFC1, intestinal folate carrier-1).
CBS = cystathionine beta-synthase. Location information from GOD (*), from MIM (**).
Goyette et al., Nat. Gen. 7:195–200 (1994)
Cook and Hamerton, Cytogenet Cell Genet. 25:9–20 (1979)
Mellman et al., Proc. Natl. Acad. Sci. 76:405–409 (1979)
Weiffenbach et al., Genomics 10:173–185 (1991)
Gilliam et al. Genomics 5:940–944 (1989b)
Jones and Kao Cytogenet Cell Genet. 37:499 (1984)
Walter et al. Ann. Hum. Genet. 56:212 (1992)
Lacey et al. Am.J Med. Genet. 60:172–173 (1989)
Ragoussis et al, Genomics 14:423–430 (1992)
Ratnum et al. Biochem. 28:8249–8254 (1989)
Garrow et al. J. Biol. Chem. 268:11910–11916 (1993).
Law and Kao, Cytogenet Cell Genet, 24:102–114 (1979)
Rozen et al., Ann. Hum. Genet, 44:781–786 (1989)
Jones et al. Somat. Cell Genet. 7:399–409 (1981)
Hori et al., Hum. Genet 85:576–580 (1990)
Silverman et al., Genomics 15:442–445 (1993)
McInnis et al. Genomics 16:562–571 (1993)
Schild et al. Proc. Natl. Acad. Sci 87:2916–2920 (1990)
Avrarmopoulos et al. Genomics 15:98–102 (1993)
Goto et al. Neuromusc Disord. 3:157–160 (1993)
Moscow et al., Cancer Res. 55:3790–3794 (1995)
Munke et al. Am J. Hum. Gen. 42:550–559 (1988)

Genes of Cobalamin Metabolism: Cobalamin metabolism is also complex [Benton and Rosenberg, In: *The Metabolic and Molecular Bases of Inherited Disease*, Disease, Scriver et a. (eds), New York: McGraw-Hill, 3129–3149 (1995)]. At least 15 gene loci (Table 4) have been identified as cobalamin-related. These contribute to the binding, transport, and metabolism of cobalamin, and its functions. A number of these have been cloned and localized to a chromosomal region (5). Cobalamin metabolism is closely intertwined with that of folate. For example, cobalamin is required for the activity of MTR, a folate-related enzyme. Decreased cobalamin can affect folate metabolism through the folate trap [Rosenblatt, In: *The Metabolic and Molecular Bases of Inherited Disease*, Scriver et al. (eds), New York: McGraw-Hill, pp. 3111–3128 (1995); Quadros et al., *Biochem. Biophys. Res. Commun.*, 222:149–154 (1996)].

TABLE 4

COBALAMIN-RELATED GENES/ENZYMES/TRANSPORTERS[a]

| Cobalamin-Related Gene/Enzymes/Tranporter[a] | SEQ ID NO: |
|---|---|
| (gastric) intrinsic factor, GIF, MIM-261000 (combined deficiency of GIF & R-binder, MIM 243320 | 31 |
| intrinsic factor receptor, IFCR, MIM-261100 | |
| transcobalamin I, TCI (an R-protein, plasma), MIM 189905 | 32 |
| transcobalamin III, TCIII (an R-protein, plasma), MIM-none | |
| other R-proteins (R-binders, cobalophylins, haptocorrins), MIM 193090 | |
| transcobalamin II, TCII MIM 275350 | 33 |
| transcobalamin II receptor, TCII receptor, MIM-none | |
| methylmalonyl Co-A mutase, MCM (MUT locus), MIM 251000 | 34 |
| cblF, lysosomal cbl efflux, MIM 277380 | |
| cblC, cytosolic cbl metabolism, MIM 277400 | |
| cblD, cytosolic cbl metabolism, MIM 277410 | |
| cblA, mitochondrial cbl reduction, (AdoCbl synthesis only), MIM 251100 | |
| cblB, cob(I)alamin adenosyltransferase, (AdoCbl synthesis only), MIM 251110 | |
| cblE, methyltransferase-associated cbl utilization, MIM 236270 | |
| cblG, methyltransferase-associated cbl utilization, MIM 250940 | |

[a]listed with alternate names, abbreviations, and MIM numbers

TABLE 5

LOCALIZED GENE LOCI RELATED TO COBALAMIN METABOLISM

| Gene/enzyme/ transport protein | Location | References |
|---|---|---|
| MCM (MUT locus) | 6p21.2-p21.1 | Qureshi et al. (1994) * |
| IF/GIF | 11q12-q13 | Hewit et al. (1991) * |
| TCI (an R-protein, plasma) | 11q11-12.3 | Johnston et al., (1992) Sigal el al., (1987), * |
| TCII | 22q11.2-q13 22q12/13 border | Li et al., (1995) | notes: MCM = methymalonyl Co-A mutase;
IF/GIF = (gastric) intrinsic factor;
TCI = transcobalmin I;
TCII = transcobalamin II.
Location information from GDB (*), from MIM (**).
Qureshi et al., Crit. Rev. Oncol. Hemaiol. 17:133–151 (1994)
Hewit et al., Genomics 10:432–440 (1991)
Johnston et al., Genomics 12:459–464 (1992)
Sigal et al.,N. Engl. J. Med. 317:1330–1332 (1987)
Li et al., Biochem. Biophys. Res. Comm. 208:756–764 (1995)

Genes of Pyridoxine Metabolism: Pyridoxine metabolism is also complex with three dietary forms convertible to pyridoxal phosphate [Whyte et al., *Hypophosphatasia*, In: The Metabolic and Molecular Bases of Inherited Disease, Scriver et al. (eds), New York: McGraw-Hill pp. 4095–4111 (1995)] and many pyridoxine-related and pyridoxine-dependent enzymes including decarboxylases and all aminotranferases (Table 6). A number of pyridoxine-related enzymes have been cloned and localized to a chromosomal region (Table 7). Pyridoxine metabolism is related to folate metabolism, especially 1-carbon transfer reactions: both serine hydroxymethyltransferases and the P-protein (glycine decarboxylase) of the glycine breakdown system are pyridoxine-dependent.

TABLE 6

SOME PYRIDOXINE-RELATED GENES/ENZYMES/[a]

| | |
|---|---|
| 1. cystathionine beta-synthase, CBS, | MIM 236200 |
| 2. gamma-cystathionase, (L-cystathionine cysteine-lyase, deaminating), LCCL | MIM 219500 |
| 3. glycine cleavage system (GCS): glycine decarboxylase (P-protein) | |
| 4. serine hydroxymethyltransferase 1, SHMT1, | MIM 182144 |
| 5. serine hydroxymethyltransferase 2, SHMT2, | MIM 138450 |
| 6. kynureninase | MIM 278600 |
| 7. all aminotransferases, (e.g. ornithine-gamma-aminotranferases, OAT,) | MIM 258870 |
| 8. decarboxylases, e.g. glutamic acid decarboxylases, GAD1, GAD2, | MIM 266100 |
| 9. pyridoxamine(pyridoxine)-5'-phosphate oxidase | MIM 603287 |

[a]listed with alternate names, abbreviations, and MIM numbers.

TABLE 7

SOME LOCALIZED GENE LOCI RELATED TO PYRDOXINE METABOLISM

| Gene/enzyme | Location | References |
|---|---|---|
| 1. GAD2 | 2q31, | Bu et al., 1992) |
| 2. GCS P-protein | 9p13 | Hamosh et al. 1995) |
| 3. GAD1 | 10p11.23 | Bu et al. 1992) |
| 4. OAT | 10q26 | ** |
| 5. SHMT2 | 12q12-14 | Garrow et al., 1993; Law and Kao, 1979 |
| 6. LCCL | 16pter-qter | *, ** |
| 7. SHMT1 | 17p11.2 | Garrow et al. 1993 * ** |
| 8. CBS | 21q22.3 | Munke et al. 1988 |
| 9. PNPO (PPO) | | Ngo et al. 1998 |

[a]listed with alternate names, abbreviations, and MIM numbers.
Location information from GDB (*), from MIM (**).
notes:
GAD2 = glutamic acid decarboxylase 2, 67 kDa.
GCS = glycine cleaving system.
P-protein = glycine decarboxylase subunit.
GAD1 = glutamic acid decarboxylase 1, 65 kDa.
OAT = omithine-gamma-aminotranferases.
SHMT2 = serine hydroxymethyltransferase 2, mitochondrial.
LCCL = gamma-cystathionase (L-cystathionine cysteine-lyase (deaminating).
SHMT1 = serine hydroxymethyltransferase 1, soluble.
CBS = cystathionine beta-synthase.
PNPO = pyridoxamine(pyridoxine)-5'-phosphate oxidase

REFERENCES

Bu et al., *Proc. Nat. Acad. Sci.,* 89:2115 (1992).
Hamosh et al., In: "The Metabolic and Molecular Bases of Inherited Disease", Scriver et al. (eds), New York: McGraw-Hill pp. 1337–1348 (1995).
Garrow et al. *J. Biol. Chem.* 268:11910–11916 (1993).
Law and Kao, *Cytogenet Cell Genet,* 24: 102–114 (1979).
Munke et al. *Am J. Hum. Gen.* 42:550–559 (1988).
Ngo et al. *Biochemistry* 37:7741–7748 (1998).

Relevance of Folate, Cobalamine, And Pyridoxine to Schizophrenia: There is considerable evidence that schizophrenia results, at least in part, from damage to brain development in utero that becomes symptomatic in late adolescence or early adulthood. The etiology of schizophrenia has both genetic and environmental components. Because folate, cobalamin, and pyridoxine are all ingested and metabolized, they could potentially be both environmental and genetic factors for schizophrenia. Folate, cobalamin, and pyridoxine are relevant to schizophrenia in important ways. First, all of them are required for cell division because of their role in nucleic acid synthesis [Rosenblatt, In: *The Metabolic and Molecular Bases of*

*Inherited Disease*, Scriver et al. (eds) New York: McGraw-Hill, pp. 3111–3128 (1995); Benton and Rosenberg, In: *The Metabolic and Molecular Bases of Inherited Disease*, Scriver et al. (eds)., New York: McGraw-Hill, 3129–3149 (1995)]. The developmental brain insult implicated in schizophrenia [Akbarian et al., *Arch. Gen. Psychiatry*, 50:169–177 (1993); Akbarian et al., *Arch. Gen. Psychiatry*, 50:178–187 (1993)] is an abnormality of neurogenesis and neuronal migration, which are midtrimester events requiring cell division. Thus folate, cobalamin, and pyridoxine deficiencies could result in the widespread decreased grey matter volume observed in schizophrenia.

Individuals that become schizophrenic later in life are more likely to be born during the winter and early spring [Boyd et al., *Schizophr. Bull.*, 12:173–186 (1986); Kendell and Adams, *Br. J. Psychiatry*, 158:758–763 (1991); O'Callaghan et al., *Br. J. Psychiatry*, 158:764–769 (1991)]; this corresponds to midtrimester in late fall & winter. Many folate- and pyridoxine-containing foods, e.g. dark green leafy vegetables, are less readily available in late fall & winter in northern climates. Seasonality was found to be a major determinant of micronutrient status including folate status in a population of pregnant and lactating women in The Gambia where folate deficiency was widespread [Bates et al. Eur. J. Clin. Nutr. 48:660–668 (1994)]. Dietary cobalamin comes from animal foods, e.g. meat, dairy products, and fish, and prolonged dietary insufficiency is required to produce cobalamin deficiency unless a person is a strict vegetarian or already has subclinical deficiency [Sanders and Reddy, *Am. J. Clin. Nutr.*, 59:1176S–1181S (1994)]. In fact, a significant fraction of the population already has subclinical deficiency for folate (Lewis et al., *Ann. NY Acad. Sci.*, 678:360–362 (1993)] and for [Carmel et al., *Arch. Intern. Med.*, 147:1995–1996 (1987); Pennypacker et al., *J. Am. Geriatr. Soc.*, 40:1197–1204 (1992); Naurath et al., *Lancet.*, 346:85–89 (1995); Allen et al., *Am. J. Clin. Nutr.*, 62:1013–1019 (1995); Black et al., *J. Nutr.*, 124:1179–1188 (1994)]. Also, the dietary folate requirement increases during pregnancy [Scholl et al., *Am. J. clin. Nutr.*, 63:520–525 (1996); McPartlin et al., *Lancet.*, 341:148–149 (1993)] and most women become folate deficient during late pregnancy [Giles, *J. Clin. Pathol.*, 19:1–11 (1966)]. Cobalamin deficiency is also common during pregnancy [Gadowsky et al., *J. Adolesc. Health*, 16:465–474 (1995)] although subnormal levels of vitamin B12 during pregnancy must be interpreted with caution [Metz et al., *Am. J. Hemetol.*, 48:251–255 (1995)]. An increase in schizophrenia births has also been noticed after winter famine [Susser and Lin, *Arch. Gen. Psychiatry*, 49:983–988 (1992)]; Susser et al., *Arch. Gen. Psychiatry*, 53:25–31 (1996)], a time when severe dietary deficiency of both folate and cobalamin is more likely. A temporary increase in the incidence of neural tube defects was reported in Jamaica 11–18 months following Hurricane Gilbert and was found to be associated with decreased dietary folate [Duff and Cooper, *Am J. Pub. Health* 84:473–476 (1994)].

Schizophrenia is also associated with obstetrical complications, e.g. low birth weight and prematurity [Lewis and Murray, *J. Psychiatr. Res.*, 21:413–421 (1987)]. Low birthweight and prematurity have also been associated with dietary folate deficiency during pregnancy Scholl et al., *Am. J. clin. Nutr.*, 63:520–525 (1996). Hyperhomocysteinemia is a risk factor for unexplained recurrent early pregnancy loss [Wouters et al., *Fertil. Steril.*, 60:820–825 (1993)] and for abruptio placentae [Goddijn-Wesel et al., *Eur. J. Obstet. Gynecol. Reprod. Biol.*, 66:23–29 (1996)]. Hyperhomocysteinemia may be related to defects in folate-, cobalamin-, or pyridoxine-dependent reactions [Naurath et al., *Lancet.*, 346:85–89 (1995)].

Interestingly, stillbirths and schizophrenia share a similar seasonality of birth excess [Torrey et al., *Schizophr. Bull.*, 19:557–562 (1993)]. Also $N_2O$, an anaesthetic gas that inhibits MTR, a cobalamin-requiring enzyme of folate metabolism, is a reproductive toxin for both men and women [Louis-Ferdinand, *Adverse Drug React. Toxicol Rev.*, 13:193–206 (1994)]. Methotrexate, an inhibitor of dihydrofolate reductase (DHFR), induces abortion.

Dietary folate deficiency and low plasma folate are common in inner city urban populations [Scholl et al., *Am. J. clin. Nutr.*, 63:520–525 (1996)]. Likewise, schizophrenia has been reported to be more common in inner city urban populations [Fuller and Bowler, *Schizophr. Bull.*, 16:591–604 (1990)]. Also, both low folate intake [Schorah and Wild, *Lancet.*, 341:1417 (1993)] and schizophrenia [Dohrenwned et al., *Science*, 255:946–952 (1992)] are correlated with lower socioeconomic status.

Immune function is impaired in folate deficiency [LeLeiko and Chao, In: *Rudolph's Pediatrics*, 20th ed., Stamford, Conn.: Appleton & Lange, pp. 1001–1010 (1996)], in cobalamin deficiency [Hitzig et al., *Ciba. Found. Symp.*, 68:77–91 (1978)] and in pyridoxine deficiency [Trakatellis et al. *Postgrad Med. J.* 73:617–622 (1997)] and deficient individuals are more susceptible to infection. Methotrexate, an inhibitor of dihydrofolate reductase, inhibits immune function [Hughes, In: *Rudolph's Pediatrics*, 20th ed., Stamford, Conn.: Appletone and Lange, pp. 517–519 (1997)]. And, as mentioned, dietary folate and cobalamin requirements increase during pregnancy [Scholl et al., *Am. J. clin. Nutr.*, 63:520–525 (1996); McPartlin et al., *Lancet.*, 341:148–149 (1993)]. This is relevant because the season-of-birth effect just mentioned in connection with dietary folate, or cobalamin deficiency has also been explained by in utero infectious illness, the "viral theory" of schizophrenia. Individuals born following winters with severe influenza epidemics are more likely to develop schizophrenia [Adams et al., *Br. J. Psychiatry*, 163:522–534 (1993)] though not all studies find this effect. Although it has not been demonstrated that either the schizophrenia fetus or the pregnant mother actually developed influenza, the histologic pattern in schizophrenia of a neuronal migration abnormality during brain development has been seen as compatible with a fetal viral infection [Kovelman and Scheibel, *Biol. Psychiatry*, 19:1601–1621 (1984); Bogerts et al., *Arch. Gen. Psychiatry*, 42:784–791 (1985); Akbarian et al., *Arch. Gen. Psychiatry*, 50:169–177 (1993); Akbarian et al., *Arch. Gen. Psychiatry*, 50:178–187 (1993)]. Thus folate or cobalamin, deficiency during pregnancy could result in greater susceptibility to viral infection affecting mother, fetus, or both. The infectious agent could be influenza itself. Alternatively, a severe influenza epidemic could be a "marker" of a severe winter, and infection by another agent could cause the brain damage. In this way, folate or cobalamin deficiency could cause the season-of-birth effect either through the mechanism of dietary deficiency alone, through maternal immune deficiency and infection, or both.

Methotrexate, a DHFR inhibitor, is also an important therapeutic agent for rheumatoid arthritis. Rheumatoid arthritis has repeatedly been found to have a decreased frequency in schizophrenics, a puzzling finding that remains unexplained [Eaton et al., *Schizophr. Res.*, 6:181–192 (1992)].

The developmental model of schizophrenia postulates that brain damage sustained in the second trimester of fetal life results in schizophrenia later in development [Brixey et al., *J. Clin. Psychol.,* 49:447–456 (1993)]. Both folate and cobalamin are already known to contribute to a first trimester fetal nervous system malformation, spina bifida cystica [Kirke et al., *Q. J. Med.,* 86:703–708 (1993); Gordon, *Brain Dev.,* 17:307–311 (1995)], and possibly other birth defects [Shaw et al., *Lancet,* 346:393–396 (1995); Czeizel, *Lancet.,* 345:932 (1995)]. Some studies [Whitehead et al., *Q. J. Med.,* 88:763–766 (1995); van der Put et al., *Lancet.,* 346:1070–1071 (1995); Ou et al., *Am. J. Med. Genet.,* 63:610–614 (1996); Chatkupt et al., *Am. Acad. Neurol. Works in Progres,* WIP4: (1996)] suggest that a genetic susceptibility factor for spina bifida is a common allele of the folate gene, MTHFR, the nucleotide 677C->T transition converting an alanine residue to valine resulting in a heat-labile enzyme protein.

Homozygotes for this allele, about 10% of the normal population, have lower erythrocyte folate and plasma folate during pregnancy [Molloy et al., *Lancet.,* 349:1591–1593 (1997)]. Homozygotes for this allele also develop moderately elevated blood homocysteine [van der Put et al., *Lancet.,* 346:1070–1071 (1995); Frosst et al., *Nature Genet.,* 10:111–113 (1995)] in the presence of dietary folate deficiency. Moderate hyperhomocysteinemia is toxic to adults [Fermo et al., *Ann. Intern. Med.,* 123:747–753 (1995)], and toxic to the fetus in early gestation [Wouters et al., *Fertil. Steril.,* 60:820–825 (1993)], and possibly teratogenic in the first trimester causing neural tube defects [Whitehead et al., *Q. J. Med.,* 88:763–766 (1995); van der Put et al., *Lancet.,* 346:1070–1071 (1995); Ou et al., *Am. J. Med. Genet.,* 63:610–614 (1996). Thus, the MTHFR heat-labile mutation, in the presence of decreased dietary folate in midtrimester, could be teratogenic both through hyperhomocysteinemia and also through folate deficiency causing the developmental brain damage hypothesized in the developmental model of schizophrenia [Brixey et al., *J. Clin. Psychol.,* 49:447–456 (1993)]. A second common polymorphism of MTHFR, the nt1298 A->C mutation could also be a genetic risk factor for spina bifida [van der Put et al., *Lancet.,* 346:1070–1071 (1995).

Schizophrenia is a common disorder, affecting 1% or more of the population [Karno et al., In: *Comprehensive Textbook of Psychiatry/VI,* 6th ed., Baltimore: Williams & Wilkins, pp. 902–910 (1995)]. Thus, if a significant proportion of schizophrenia shares a common etiology, both the genetic susceptibility factors and the environmental factors must be common in the population. As mentioned earlier, a significant fraction of the population is already subclinically deficient for folate and for cobalamin; also, pregnancy may increase this fraction since dietary folate and cobalamin requirements increase during that time. Several functional polymorphic alleles of folate and cobalamin genes are also common in the population including the MTHFR mutations just mentioned and polymorphisms of thymidylate synthase [Horie et al., *Cell Struct. Funct.,* 20:191–197 (1995)], transcobalamin II [Li et al., *Biochim. Biophys. Acta.,* 1219:515–520 (1994)], and folate-binding proteins [Li et al., 1994, supra; Shen et al., *Biochem.,* 33:1209–1215 (1994)]. Metabolic indicators of folate or cobalamin deficiency, e.g. hyperhomocysteinemia and hypermethylmalonicacidemia, are also common in the population [Naurath et al., *Lancet.,* 346:85–89 (1995)]. Thus there exists a statistical basis for the hypothesis that schizophrenia is a birth defect resulting from the action during gestation of genetic risk factors and environmental factors related to folate and/or cobalamin that lead to the generation of risk factors. Such factors are sufficiently common that at least in principle all cases of schizophrenia could result from this mechanism.

Finally, folate, cobalamin, and pyridoxine are relevant for schizophrenia because of findings in patients. Severe genetic deficiency of MTHFR may cause a "schizophrenia" phenotype [Freeman et al., *N. Engl. J. Med.,* 292:491–496 (1975); Regland et al., *J. Neural Transm. Gen. Sect.,* 98:143–152 (1994)]. Genetic deficiency of other folate and cobalamin enzymes has been reported to cause nervous system disease, psychiatric disease, or schizophrenia-like illness [Mudd et al., In: *The Metabolic and Molecular Bases of Inherited Disease,* Scriver et al. (eds), New York: McGraw-Hill pp. 1279–1327 (1995); Hitzig et al., *Ciba. Found. Symp.,* 68:77–91 (1978); Cooper and Rosenblatt, *Annu. Rev. Nutr.,* 7:291–320 (1987); Shevall and Rosenblatt, *Can. J. Neurol. Sci.,* 19:472–486 (1992); Hall, *Br. J. Haematol.,* 80:117–120 (1992)]. Likewise, dietary deficiencies of folate or cobalamin may have similar effects [Cooper and Rosenblatt, *Annu. Rev. Nutr.,* 7:291–320 (1987); Shevall and Rosenblatt, *Can. J. Neurol. Sci.,* 19:472–486 (1992)]. Methylfolate therapy reportedly improved the clinical status of schizophrenics with borderline or definite folate deficiency [Godfrey et al., *Lancet.,* 2:392–395 (1990); Procter, *Br. J. Psychiatry,* 159:271–272 (1991)] although the improvement claimed was small and the finding controversial. Folate deficiency has been associated with disturbances in mood [Shulman, In: *Folic Acid in Neurology, Psychiatry, and Internal Medicine,* New York: Raven Pr., 463–474 (1979)], and it has been suggested that the most common neuropsychiatric system abnormality in severe folate deficiency is depression [Reynolds et al., *Lancet.,* ii:196–198 (1984)]. Methyltetrahydrofolate reportedly improved symptoms of depression in an open trial in elderly depressed patients [Guaraldi et al. *Ann. Clin. Psychiatry* 5:101–105 (1993)]. Schizophrenics are reported to have an 80% excess mortality from cardiovascular disease [Gottesman, *Schizophrenia Genesis,* Schizophrenia Genesis—The Origins of Madness, W. H. Freeman & Co. N.Y. (1991)]; hyperhomocysteinemia, dietary folate deficiency and the MTHFR 677C->T mutation have been implicated in cardiovascular disease in some studies [Morita et al., *Circulation,* 95:2032–2036 (1997)] but not others (Anderson et al., *J. Am. Coll. Cardiol.* 30:1206–1121 (1997)]. Also, kynureninase, an important enzyme of tryptophan metabolism, affecting niacin metabolism and serotonin synthesis, is pyridoxine-dependent. Niacin deficiency (pellagra) can cause mental changes including psychosis and hallucinations [Wilson, *Vitamin deficiency and excess,* pp. 472–480. In: *Harrison's Principles of Internal Medicine,* (Scriber et al. e's.) McGraw-Hill, Inc., N.Y. (1994)]. Also, clozapine, resperidone, and olanzapine are thought to exert their antipsychotic effect in schizophrenia in part through serotonin receptor antagonism.

Gene Localization Studies in Schizophrenia and Folate/Cobalamine/Pyridoxine Genes: If folate, cobalamin, or pyridoxine genes are susceptibility factors for schizophrenia, it is possible that gene localization studies have already identified candidate chromosome regions that contain such a gene (Tables 3, 5, and 7). For three folate or cobalamin genes, DHFR, TCNII and TYMS, there is excellent concordance with schizophrenia gene localization studies.

On chromosome 5, DHFR has been located at 5q11.2–13.2. A schizophrenia translocation [t(1;5) (1q32.3;5q11.2–13.3)] was reported [McGillivray et al., *Am. J. Med. Genet.,* 35:10–13 (1990); Bassett, *Br. J. Psychiatry,* 161:323–334 (1992)] affecting 5q11.2–5q13.3. A proband and uncle, both with schizophrenia and eye-tracking abnormalities, had partial trisomy for 5q11.2–5q13.3; the third copy was inserted at 1q32.3 giving a derivative chromosome, der(1inv ins(1;5)(q32.2;q13.3q11.2). The proband's mother had a balanced translocation but was phenotypically normal without schizophrenia or eye-tracking abnormalities. She had the derivative chromosome 1 with extra material from chromosome 5 inserted but a corresponding deletion in one of her chromosomes 5. She thus had only two copies of 5q11.2–5q13.3. Further studies [Gilliam et al., Genomics, 5:940–944 (1989)] showed that the DHFR gene is located within this deleted region, 5q11.2–13.3. Another schizophrenia chromosome abnormality, inv5(p13;q13), has been reported [Bassett, Br. J. Psychiatry, 161:323–334 (1992)] affecting 5q13.

On chromosome 5, two-point lod scores of 4.64 and 2.29 were found [Sherrington et al., Nature, 336:164–167 (1988)] for the polymorphic markers D5S76 and D5S39 respectively in the region of the chromosome abnormality just discussed [McGillivray et al., i Am. J. Med. Genet., 35:10–13 (1990); Bassett, Br. J. Psychiatry, 161:323–334 (1992)] affecting 5q11.2–13.3. Two other linkage studies found small positive lod scores in this region [Coon et al., Biol. Psychiatry, 34:277–289 (1993); Kendler and Diehl, Schizophr. Bull., 19:261–285 (1993)], but numerous other studies excluded this region under the assumptions and models used [Kendler and Diehl, Schizophr. Bull., 19:261–285 (1993)].

On chromosome 18, TYMS has been located at 18p11.32–p11.22. A ring chromosome with deletion of 18pter-p11,18q23-qter [Bassett, Br. J. Psychiatry, 161:323–334 (1992)] was reported in a kindred with schizophrenia and bipolar illness [Bassett, Br. J. Psychiatry, 161:323–334 (1992)]. Deletion of a segment of 18p was reported in a schizophrenia chromosome [Bassett, Br. J. Psychiatry, 161:323–334 (1992)].

On chromosome 22, TCNII has been located at 22q11.2–q13, possibly at the 22q12/13 border. High lod scores have consistently been obtained in the region of TCNII: IL2RB, in 22q12–q13.1 gave a lod score [Pulver et al., Am. J. Med. Genet., 54:3–43 (1994)] of 2.82. Other markers over a broad region of 22q have given suggestive lod scores. D22S278, in 22q12, gave a lod score [Vallada et al., Am. J. Med. Genet., 60:139–146(1995)] of 1.51. CRYB2, in 22q11.2–q12.1, gave a lod score [Lasseter et al., Am. J. Med. Genet., 60:172–173 (1995)] of 1.71. D22S10, in 22q11.1–q11.2, gave a lod score [Coon et al., Biol. Psychiatry, 34:277–289 (1993)] of 0.79. Highly significant p-values for non-parametric analyses have also been obtained: D22S278, in 22q12, for example gave p=0.001 [Gill et al., Am. J. Med. Genet., 67:40–45 (1996)].

The deletions of velocardiofacial (VCF) syndrome and related disorders (DiGeorge syndrome (DGS) and CATCH22) are located [Lindsay et al., Genomics, 32:104–112 (1996)] at 22q11.2. A psychotic disorder develops in about 10% of patients with VCF syndrome [Chow et al., Am. J. Med. Genet., 54:107–112 (1994)]. TCNII is not known to be located at or within these deletions. VCF and related disorders are relatively uncommon compared to schizophrenia; only 2 of 100 randomly selected patients (92 schizophrenics, 5 with schizoaffective disorder, and 3 with schizophreniform disorder) in the Maryland Epidemiological Sample were found [Lindsay et al., Am. J. Hum. Genet., 56:1502–1503 (1995)] to have VCF-related deletions (and later VCF syndrome) on 22q11.2. Consequently, it is not clear whether schizophrenia linkage studies are detecting a haplotype related to a VCS locus or some other locus in this region, such as TCNII.

For some other folate, cobalamin, or pyridoxine relevant genes, physical or genetic studies of schizophrenia have identified chromosomal regions near the gene.

Discussion

The folate-cobalamin hypothesis for schizophrenia is attractive because it suggests that a single mechanism of genetic and environmental factors may play a major role in the etiology and pathogenesis of schizophrenia. The combined result of this mechanism is to damage fetal development, especially brain development by inhibiting nucleic acid synthesis, by affecting gene methylations, by increasing susceptibility to infection, and/or by producing teratogens.

This mechanism addresses several puzzling features of schizophrenia such as the season of birth effect, the association with famine and influenza epidemics, the negative association with rheumatoid arthritis, the associations with obstetrical abnormalities, social class, and urban environment. The mechanism also suggests approaches to diagnostic testing, to prevention, and to improved therapy.

It is not excluded that such a mechanism could also apply to a number of common human developmental disorders that have been shown to have a genetic component to their etiology but whose mode of inheritance has been difficult to determine and for which linkage studies have met with unexpected difficulties or have achieved limited success. These developmental disorders include Tourette's syndrome & related disorders (e.g. obsessive-compulsive disorder and chronic multiple tics syndrome) [Pauls, Adv Neurol, 58:151–157 (1992); McMahon et al., Adv Neurol, 58:159–165 (1992); Heutink et al., Am J Hum Genet, 57:465–473 (1995); Grice et al., Am J Hum Genet, 59:644–652 (1996)], leaning disorders, including dyslexia [Lewis, et al., Behav Genet, 23:291–297 (1993); Pennington, J Child Neurol 10 Suppl, 1:S69–S77 (1995)], conduct disorder [Lombroso et al., J. Am. Acad. Child Adolesc. Psychiatry, 33:921–938 (1994)], attention-deficit hyperactivity disorder [Lombroso et al., 1994, J. Am. Acad. Child Adolesc. Psychiatry, 33:921–938 (1994)], bipolar illness [Baron, Acta. Psychiatr. Scand., 92:81–86 (1995); Benjamin and Gershon, Biol. Psychiatry, 40:313–316 (1996); Risch and Botstein, Nature Genet., 12:351–353 (1996); Jamison and McInnis, Nature Med., 2:521–522 (1996); Morell, Science, 272:31–32 (1996)], autism [Lombroso et al., 1994, J. Am. Acad. Child Adolesc. Psychiatry, 33:921–938 (1994)], and obsessive-compulsive disorder in adults [Lombroso et al., 1994, J. Am. Acad. Child Adolesc. Psychiatry, 33:921–938 (1994)]. Some of these disorders have been shown to be associated with schizophrenia.

The present invention may be better understood by reference to the following non-limiting Examples, which are provided as exemplary of the invention. The following Examples are presented in order to more fully illustrate one embodiment of the invention. They should in no way be construed, however, as limiting the broad scope of the invention.

EXAMPLE 1

Diagnosing Schizophrenia

Structure of Datafiles

Data are arranged in a file suitable for input into a binary logistic regression program (Table 8). A model is created consisting of those explanatory variables actually available from the specific patient-to-be-diagnosed and family members participating in the testing. This new combined data set (reference data set+data from patient-to-be-diagnosed with participating family members) is analyzed by binary logistic regression for the model chosen giving the predicted probability that a proband is affected with schizophrenia for all of the probands including the patient-to-be-diagnosed.

The model can be modified if required. The goodness of fit for the patient-to-be-diagnosed is checked. The predicted probability that the patient-to-be-diagnosed has schizophrenia is compared with a classification table generated from the model used to determine likelihood of false positives and false negatives. The predicted probability that the patient-to-be-diagnosed is affected with schizophrenia, with likelihood of false positive or false negative result, is returned to the clinician.

(iv) by whether the individual has a single or double dose of the mutation. Thus an explanatory variable P321 records whether the proband has a single dose of the second-designated mutation of the third-designated locus, i.e. TCN2. A variable M312 records whether the proband's mother has a double dose of the first-designated TCN2 mutation studied.

In the present hypothetical reference dataset illustrated of genetic explanatory variables (Table 8), partial genotype

TABLE 8

A HYPOTHETICAL PARTIAL REFERENCE DATA SET OF GENETIC EXPLANATORY VARIABLES TO ILLUSTRATE DATA STRUCTURE

| ID | resp | P111 | P112 | P211 | P212 | M111 | M112 | M311 | F511 | S2-411 | CA1-111 |
|---|---|---|---|---|---|---|---|---|---|---|---|
| 1 | 1 | 1 | 0 | 1 | 1 | 1 | 1 | 0 | 0 | 1 | 1 |
| 2 | 1 | 1 | 0 | 0 | 0 | 0 | 0 | 0 | 1 | 0 | 0 |
| 3 | 1 | 1 | 1 | 1 | 0 | 1 | 0 | 0 | 1 | 1 | 1 |
| 4 | 1 | 0 | 0 | 0 | 0 | 0 | 0 | 1 | 0 | 0 | 0 |
| 5 | 1 | 0 | 0 | 1 | 1 | 1 | 1 | 0 | 0 | 0 | 1 |
| 6 | 0 | 1 | 0 | 0 | 0 | 0 | 0 | 0 | 0 | 0 | 0 |
| 7 | 0 | 0 | 0 | 0 | 0 | 0 | 0 | 1 | 0 | 0 | 0 |
| 8 | 0 | 0 | 0 | 1 | 0 | 0 | 0 | 0 | 1 | 1 | 0 |
| 9 | 0 | 1 | 0 | 0 | 0 | 1 | 0 | 0 | 0 | 1 | 1 |
| 10 | 0 | 0 | 0 | 0 | 0 | 1 | 0 | 0 | 0 | 1 | 0 |
| 11 | ... | | | | | | | | | | |
| n | | | | | | | | | | | |

For each proband (Table 8), the record contains several variables:

identification number (ID) of the proband.

a binary response variable (resp) for affection status of the proband: response=1, if the proband is affected with schizophrenia; response=0 if proband is unaffected (i.e. a control individual). The proband is not necessarily one of the individuals for whom genotype data (explanatory variables) are available. The patient-to-be-diagnosed is assigned response=0 when added to the reference data set.

a set of explanatory variables: i.e. sets of genotypes of mutations found in the schizophrenia patients and family members and controls and family members. The schizophrenia patients and the control individuals are probands (P) as is the patient-to-be-diagnosed. Unaffected family members are the proband's mother (M), father (F), sib(s) (S1, S2, etc.), child(ren) (C1, C2, etc.) or other relatives. Data for affected family members, e.g. the proband's mother (MA), father (FA), sibs (SA1, SA2, etc.), children (CA1, CA2, etc.), or other relatives, are entered as separate explanatory variables.

Genetic explanatory variables: Each individual has 0, 1, or 2 copies of any given mutation allele at a given locus. Thus a genotype at each locus contributes two independent explanatory variables. Most of the affected family members will be relatives of schizophrenia probands, but occasionally a relative of an unaffected proband will turn out to be affected with schizophrenia.

Mutations are tabulated as explanatory variables: (see Table 8):
(i) by the proband or relative in whom they occur, (e.g. P, M, F, S2, C1, MA, FA, SA1, CA1, other);
(ii) by the specific folate, cobalamin, or pyridoxine gene locus in which they occur (e.g. 1=DHFR locus, 2=MTHFR locus, 3=TCN2 locus, 4=MTR locus, 5=CBS locus, etc.);
(iii) by the specific mutation within a locus (e.g., 1=the first-designated mutation within a locus, 2=the second-designated mutation within a locus, etc.); and data for probands, mothers, fathers, sibs and children are given for five gene loci. Not all of the possible explanatory variables are shown. Probands 1–5 are unrelated individuals with the definite clinical diagnosis of schizophrenia; probands 6–10 are unrelated unaffected (control) individuals. Probands 1, 2, 3, 6 and 9 all have a single copy of the first-designated DHFR mutation; proband 3 also has a second copy of that mutation. Probands 1, 3, 5 and 8 all have a single copy of the first-designated mutation at the MTHFR locus; probands 1 and 5 also have a second copy of that mutation. Mothers of probands 1, 3, 5, 9 and 10 all have a single copy of the first-designated DHFR mutation; mothers of probands 1 and 5 also have a second copy of this mutation. Mothers of probands 4 and 7 each have a single copy of the first-designated mutation of TCN2; data for a double dose are not shown. The fathers of probands 2, 3, and 8 each have a single copy of the first designated mutation of CBS; data for a double dose are not shown. The second (unaffected) sibs of probands 1, 3, 8, 9, and 10 each have a single copy of the first-designated mutation of MTR; data for a double dose are not shown. The first affected children of probands 1, 3, 5, and 9 each have a single copy of the first-designated mutation of DHFR. Other susceptibility loci and mutations can be incorporated in Table 8 in the same fashion e.g., cytokine gene mutations or polymorphisms, or major histocompatibility complex (MHC) mutations or polymorphisms.

Environmental explanatory variables: If only genetic explanatory variables (genotype data) are used, the maximum predicted probability that the proband is affected with schizophrenia is expected to be approximately about 0.5 in most populations. When environmental risk factors are included as explanatory variables, the maximum predicted probability that the proband is affected with schizophrenia may approach 1.0. Examples of environmental risk factors for a schizophrenia patient include:
(1) the proband's dietary folate/cobalamin/pyridoxine intake.
(2) the proband's circulating levels of folate/cobalamin/pyridoxine.

(3) the proband's circulating levels of homocysteine, methylmalonic acid, or cystathionine. Elevated levels are indicators of subtle folate/cobalamin deficiency.

(4) the proband's mother's dietary folate/cobalamin/pyridoxine intake at the time of patient diagnosis, during a pregnancy, or during the pregnancy that produced the proband.

(5) the proband's mother's circulating levels of homocysteine, methylmalonic acid, or cystathionine at the time of patient diagnosis, during a pregnancy, or during the pregnancy that produced the proband.

(6) dietary or circulating folate/cobalamin/pyridoxine or circulating levels of homocysteine, methylmalonic acid, or cystathionine for other family members.

(7) epidemiological factors related to the proband's gestation and birth, e.g. low birth weight or preterm birth, maternal infection, maternal smoking (associated with low plasma folate), season of birth (late winter or spring births are more common in schizophrenia), etc.

Method of Data Analysis

The method exemplified herein is based upon the published guide for the SAS system, but other software can be used. The dataset is analyzed using binary logistic regression to model the response probability, $p_i$, that the ith proband's affection status is 1, i.e. the probability that the ith proband has schizophrenia, given the vector of explanatory variables, $x_i$. That is:

$$p_i = \text{Prob}(y_i=1|x_i).$$

To do this the logit transformation of $p^i$ is modeled as a linear function of the explanatory variables in the vector, $x_i$:

$$\text{logit}(p_i) = \log(p_i/[1-p_i]) = \text{alpha} + \text{beta}'x_i$$

where: alpha is the intercept parameter and beta is the vector of slope parameters.

In SAS, the "descending" option is used to model the probability that the response=1, as in the present analysis, rather than response=0.

Outputs of Binary Logistic Regression Analysis

After analysis of a dataset, the outputs obtained from SAS include:

(a) Estimates and standard errors of the parameters (alpha and beta). Using estimates of the intercept parameter (alpha) and the slope parameter (beta) for each environmental or genetic risk factor, the logistic regression equation for the dataset can be written.

(b) Significance tests of the parameters (e.g. Wald chi-square). From the corresponding p-values, the level of significance of each of the environmental or genetic risk factors is determined. A global significance test of the data with corresponding p-value is also determined.

(c) Odds ratios are given for the slope parameters of each environmental or genetic risk factor. Thus the amount contributed by each environmental or genetic risk factor to the risk of schizophrenia is determined.

(d) The confidence limits for regression parameters and odds ratios are determined.

(e) The predicted probabilities of the observations can be computed, i.e. the probability that each individual in the dataset has schizophrenia:

alpha~=estimate of the intercept parameter;

beta~=vector of the estimates of the slope parameters;

x=vector of the explanatory variables;

p~=predicted probabilities $$p \sim = \frac{1}{1 + \exp(\text{alpha} \sim -\text{beta} \sim' x)}$$

(f) The model is modified by adding or removing variables until a model is found that best fits the data.

(g) The model is tested for goodness-of-fit. Also, the degree of influence of each specific observation is tested to detect extreme or ill-fitting observations. These may be examples of data entry errors or alternatively, observations that do not fit the present model for schizophrenia.

(h) The probability that a new individual (the patient-to-be-diagnosed) is schizophrenic is then calculated from the final, modified, best fitting regression equation based upon parameters derived from a corrected/modified data set. A simple method of doing this is to add the data for the patient-to-be-diagnosed to the reference data set, a large group of well-studied schizophrenia probands, schizophrenia family members, control probands and control family members for whom data are available for many explanatory variables. A model is created consisting of those informative explanatory variables actually available from the specific patient-to-be-diagnosed and family members participating in the testing. This new combined data set (reference data set+data from patient-to-be-diagnosed with participating family members) is analyzed by binary logistic regression for the model chosen giving the predicted probability that a proband is affected with schizophrenia for all of the probands including the patient-to-be-diagnosed.

(i) A classification table is produced from the data set by the "jack knifing" procedure or an approximation to it. This procedure classifies each observation as an event or non-event based on the model that omits the observation being classified. A classification table sorts observations into percent correct, percent false positives, and percent false negatives at various probability levels and computes sensitivity and specificity.

(j) The data set used for diagnostic testing is constantly being updated and the regression equation corrected. For example, stratification by geographic residence or geographic origin of ancestors must be considered for some environmental or genetic risk factor.

For example, in Table 9, entries 34–43 are shown for the data file containing genotypes of 38 schizophrenic probands plus 211 control probands; the first 38 are the affected probands. For individual 302088, the proband is affected ("1"); there is a single dose ("1") of the DHFR mutation but not a double dose ("0") and a single dose ("1") of the MTHFR mutation but not a double dose ("0"). The number 302088 identifies the individual whose genotypes are listed; the proband, in this case, is the same individual.

TABLE 9

SAS DATAFILE FOR SCHIZOPHRENIA PATIENTS AND CONTROLS

| | | | | | | |
|---|---|---|---|---|---|---|
| 34 | 302086 | 1 | 1 | 0 | 1 | 1 |
| 35 | 302088 | 1 | 1 | 0 | 1 | 0 |
| 36 | 302110 | 1 | 1 | 0 | 1 | 0 |
| 37 | 302111 | 1 | 1 | 0 | 0 | 0 |
| 38 | 302136 | 1 | 1 | 1 | 1 | 0 |
| 39 | 100001 | 0 | 1 | 0 | 0 | 0 |
| 40 | 100061 | 0 | 0 | 0 | 0 | 0 |

TABLE 9-continued

SAS DATAFILE FOR SCHIZOPHRENIA PATIENTS AND CONTROLS

| 41 | 100064 | 0 | 1 | 0 | 1 | 0 |
| 42 | 100067 | 0 | 0 | 0 | 1 | 0 |
| 43 | 100073 | 0 | 1 | 0 | 0 | 0 |
| ... | | | | | | |

In Table 10, entries 31–40 are shown for the data file containing genotypes of 35 mothers of schizophrenic probands plus (the same) 211 control probands. For individual 302083, the proband is affected ("1"); there is a single dose of the DHFR mutation ("1) but not a double dose ("0"); there is neither a single ("0") nor a double ("0") dose of the MTHFR mutation. The number 302083 identifies the individual whose genotypes are listed, a mother; the proband, in this case, is a different individual, her affected child.

TABLE 10

SAS DATAFILE FOR SCHIZOPHRENIA MOTHERS AND CONTROLS

| ... | | | | | | |
| 31 | 302083 | 1 | 1 | 0 | 0 | 0 |
| 32 | 302103 | 1 | 0 | 0 | 1 | 0 |
| 33 | 302104 | 1 | 0 | 0 | 1 | 0 |
| 34 | 302105 | 1 | 1 | 0 | 1 | 0 |
| 35 | 302120 | 1 | 0 | 0 | 0 | 0 |
| 36 | 100001 | 0 | 1 | 0 | 0 | 0 |
| 37 | 100061 | 0 | 0 | 0 | 0 | 0 |
| 38 | 100064 | 0 | 1 | 0 | 1 | 0 |
| 39 | 100067 | 0 | 0 | 0 | 1 | 0 |
| 40 | 100073 | 0 | 1 | 0 | 0 | 0 |
| ... | | | | | | |

In Table 11, entries 11–20 are shown for the data file containing genotypes of 15 fathers of schizophrenic probands plus (the same) 211 control probands. For individual 302084, the proband is affected ("1"); there is a single dose ("1") but not a double dose ("0") of the DHFR mutation; there is both a single ("1") and a double ("1") of the MTHFR mutation. The number 302084 identifies the individual whose genotypes are listed, a father; the proband, in this case, is a different individual, his affected child.

TABLE 11

SAS DATAFILE FOR SCHIZOPHRENIA FATHERS AND CONTROLS

| ... | | | | | | |
| 11 | 302102 | 1 | 0 | 0 | 0 | 0 |
| 12 | 302106 | 1 | 1 | 0 | 0 | 0 |
| 13 | 302115 | 1 | 1 | 0 | 0 | 0 |
| 14 | 302117 | 1 | 1 | 0 | 0 | 0 |
| 15 | 302084 | 1 | 1 | 0 | 1 | 1 |
| 16 | 100001 | 0 | 1 | 0 | 0 | 0 |
| 17 | 100061 | 0 | 0 | 0 | 0 | 0 |
| 18 | 100064 | 0 | 1 | 0 | 1 | 0 |
| 19 | 100067 | 0 | 0 | 0 | 1 | 0 |
| 20 | 100073 | 0 | 1 | 0 | 0 | 0 |
| ... | | | | | | |

In Table 12, entries 9–18 are shown for the data file containing genotypes of 13 unaffected sibs of schizophrenic probands plus (the same) 211 control probands. For individual 302089, the proband is affected ("1"); there is a single dose ("1") but not a double dose ("0") of the DHFR mutation; there is both a single ("1") and a double ("1") of the MTHFR mutation. The number 302089 identifies the individual whose genotypes are listed, an unaffected sib; the proband, in this case, is a different individual, the affected sib of individual 302089.

TABLE 12

SAS DATAFILE FOR SCHIZOPHRENIA SIBS AND CONTROLS

| ... | | | | | | |
| 09 | 302071 | 1 | 1 | 0 | 0 | 0 |
| 10 | 302073 | 1 | 0 | 0 | 1 | 0 |
| 11 | 302089 | 1 | 1 | 0 | 1 | 1 |
| 12 | 302118 | 1 | 1 | 0 | 0 | 0 |
| 13 | 302126 | 1 | 1 | 0 | 0 | 0 |
| 14 | 100001 | 0 | 1 | 0 | 0 | 0 |
| 15 | 100061 | 0 | 0 | 0 | 0 | 0 |
| 16 | 100064 | 0 | 1 | 0 | 1 | 0 |
| 17 | 100067 | 0 | 0 | 0 | 1 | 0 |
| 18 | 100073 | 0 | 1 | 0 | 0 | 0 |
| ... | | | | | | |

In Tables 9–12 for individual 100061, the proband is unaffected ("0"); there is neither a single dose ("0") nor a double dose ("0") of the DHFR mutation; there is neither a single dose ("0") nor a double dose ("0") of the MTHFR mutation. Since the proband is unaffected, this is a control individual. The number 100061 identifies the individual whose genotypes are listed, as a control individual; the proband, in this case, is the same individual. The identical group of control individuals is used for all four comparisons.

EXAMPLE 2

Distribution of Folate Gene Polymorphism Genotypes Among Schizophrenics, Schizophrenia Parents, Schizophrenia Sibs, and Controls

SUMMARY

The DNA polymorphism-Diet-Cofactor-Development hypothesis (DDCD hypothesis, described above) postulates that schizophrenia results in part from developmental brain damage sustained in utero from the aggregate effect of maternal defects of genes related to important cofactors, e.g. folate, cobalamin, pyridoxine, potentiated by a maternal dietary deficiency of these cofactors. The maternal damage to the fetus results in part from insufficiency of these cofactors themselves and in part from resulting effects such as immune deficiency and maternal teratogens, e.g. hyperhomocysteinemia. Genes from either parent acting in the fetus may modify these damaging effects as outlined in the gene-teratogen model (described above).

The hypothesis addresses all of the unusual biological and epidemiological features of schizophrenia: e.g. the decreased amount of grey matter in brain areas, the unusual birth-month effect, the geographical differences in incidence, the socioeconomic predilection, the association with obstetrical abnormalities (low birth weight and prematurity), the decreased incidence of rheumatoid arthritis, and the association with viral epidemics (described above).

The hypothesis can be supported by finding significant association of sequence variants of folate, cobalamin, or pyridoxine genes with schizophrenia. Folate, cobalamin, and pyridoxine absorption, transport, and metabolism are complex [Rosenblatt, In: *The Metabolic and Molecular Bases of Inherited Disease*, Scriver et al. (eds), New York: McGraw-Hill, pp. 3111–3128 (1995); Benton and Rosenberg, In: *The Metabolic and Molecular Bases of Inherited Disease*, Scriver et al (eds), New York: McGraw-Hill, pp. 3129–3149

(1995); Whyte et al., *Hypophosphatasia*, In: The Metabolic and Molecular Bases of Inherited Disease, Scriver et al. (eds), New York: McGraw-Hill pp. 4095–4111] with multiple transport proteins, enzymes, and regulatory components. A strong candidate for harboring a mutation predisposing to schizophrenia is the DHFR gene coding for the folate enzyme dihydrofolate reductase. DHFR chemically reduces dietary folate converting it into a form that can enter cellular metabolism. DHFR is also important for DNA synthesis and is known to play a major role in development in utero. A novel polymorphic 19 basepair deletion of the DHFR gene has been isolated which could be of functional significance because it affects potential transcription factor binding sites.

A second candidate is the MTHFR gene, coding for methylenetetrahydrofolate reductase, MTHFR, an important enzyme of folate metabolism. MTHFR was of particular interest because severe deficiency of enzyme activity has been associated with the "schizophrenia" phenotype [Freeman et al., *N. Engl. J. Med.*, 292:491–496 (1975); Regland et al., *J. Neural Transm. Gen. Sect.*, 98:143–152 (1994)] and because a common mutation, the nt677 C->T transition results in a mutated gene that encodes a heat-labile MTHFR, having decreased enzymatic activity, which in the presence of dietary folate deficiency, causes the plasma homocysteine of homozygotes to become elevated [van der Put et al., *Lancet.*, 346:1070–1071 (1995); Frosst et al., *Nature Genet.*, 10:111–113 (1995)]. In adults, hyperhomocysteinemia is known to cause vascular disease and to be toxic [Frosst et al., *Nature Genet.*, 10:111–113 (1995)]. Therefore, homocysteine that crosses the placenta could act as a fetal teratogen during pregnancy. Maternal folate deficiency could also have a more direct teratogenic effect through fetal folate deprivation. These effects could be potentiated by abnormalities of other folate, cobalamin, or pyridoxine genes, even if these abnormalities were only minor.

Materials & Methods

1. Subjects and Sample Collection: Patients with schizophrenia and unaffected family members of schizophrenics, were ascertained from patient facilities, patient support groups, and family support group organizations. Nearly all schizophrenia families had only a single case of schizophrenia. The patients came from different schizophrenia families than the parents and sibs. The controls were unaffected and unrelated individuals not known to be schizophrenic or related to patients with schizophrenia or spina bifida. All subjects were of Caucasian background except two of the schizophrenia patients who were of African American background.

After informed consent was obtained, 20–40 ml of blood was collected into EDTA (purple-top) vacutainers, placed on ice immediately, and transported to the laboratory where plasma, packed red cells, and buffy coat were separated by centrifugation and frozen at $-80°$ C.

2. Detection of Alleles: DNA was isolated using the QIAmp column DNA extraction procedure or the QIAGEN Genomic-tip method (QIAGEN, Chatsworth, Calif.). Alleles for a newly detected polymorphic 19 bp deletion in the dihydrofolate reductase (DHFR) gene were determined by polymerase chain reaction (PCR) amplification of the region surrounding the deletion using specific primers (FIG. 1) and direct detection of the PCR products after separation of products on a non-denaturing polyacrylamide gel. A Cetus-Perkin-Elmer 9600 thermocycler was used. Briefly, the PCR reaction contained 200 uM dNTPs, 1.5 mM $MgCl_2$, 10 pmols of each primer, in 10 ul reaction volume. The PCR conditions used were denaturation at 94° C. for 6 min. initially, followed by 35 cycles of 94° C. for 55 sec., 60° C. for 55 sec., and 72° C. for 55 sec. and a final extension at 72° C. for 12 min.

Alleles for the 677C->T transition of the methylenetetrahydrofolate reductase (MTHFR) gene were determined by cleavage with the restriction endonuclease, Hinfl, of PCR-amplified genomic DNA from blood and separation of the products by non-denaturing polyacrylamide gel electrophoresis [Frosst et al., *Nature Genet.*, 10:111–113 (1995)].

3. Sequencing the Region Around the DHFR Deletion: Using the same primers (FIG. 1), genomic DNA from individuals with 1,1 and 2,2 genotypes was amplified by PCR and the products sequenced using an ABI PRISM 377 automated sequencer. Restriction sites were identified using the MAP Program in the GCG Package. Potential transcription factor binding sites were detected with the TESS program (transcription element search software, URL:http://agave.humgen.upenn.edu/tess/index.html).

4. Data Analysis: Since the mode of inheritance of schizophrenia is unknown, binary logistic regression was used to test the DHFR deletion allele and the MTHFR heat-labile allele as genetic risk factors for schizophrenia. Either the DHFR deletion polymorphism or the MTHFR heat-labile allele could itself be a genetic risk factor for schizophrenia. The genotypes of the two folate gene polymorphisms were used as explanatory variables. Genotypes of schizophrenia patients, parents, or sibs were compared with those of controls.

Four files were constructed consisting of schizophrenia patients+controls, mothers of schizophrenia patients+controls, fathers of schizophrenia patients+controls, and sibs of schizophrenia patients+controls for input into the SAS System. Each dataset contained 6 variables. In order, these were:

1. six digit identification (ID) number;
2. response variable, i.e. affection status of the proband (0=unaffected, i.e. control individual; 1=affected, i.e. schizophrenia patient);
3. DHFR mutation-single dose (Ds);
4. DHFR mutation-double dose (Dd);
5. MTHFR mutation-single dose (Ms); and
6. MTHFR mutation-double dose (Md).

For mutation data, 0=mutation absent, 1=mutation present.

Results

Alleles of the DHFR 19 bp Deletion Polymorphism: Amplification of the region of intron 1 of DHFR defined by the primers in FIG. 1 gave two polymorphic bands of 232 and 213 bp after separation on a non-denaturing polyacrylamide gel (FIG. 2). Sequencing the PCR products from the two homozygotes showed that they differed by 19 bp (FIG. 3). The upper and lower bands (FIG. 2), non-deletion allele and deletion allele respectively, were designated alleles 1 and 2 respectively. Comparison with two published sequences showed that allele 1 was identical with one of them [Yang et al. *J. Mol. Biol.* 176:169–187 (1984)] indicating that allele 2 resulted from a 19 bp deletion. The other published sequence [Chen et al. *J. Biol. Chem.* 259:3933–3943 (1984)] was lacking one base pair of allele 1, an A indicated by "*" in FIG. 3. It is possible that this shorter reference sequence [Chen et al. *J. Biol. Chem.* 259:3933–3943 (1984)] resulted from a sequencing artifact.

Sequences in the 19 bp Deleted Region of DHFR Intron 1: The 19 bp sequence in the deleted region (FIG. 3) of DHFR intron 1 contained sites for several restriction enzymes including RsaI and ScrFI, and potential binding sites for transcription factors including Sp1, NF-kappaB, CP1 (NF-Y), E2F, ETF and GCF in the 19 base pair region.

Binary Logistic Regression Analysis: The number of individuals with each genotype of the two polymorphisms among 38 unrelated schizophrenia probands, 35 unrelated mothers of schizophrenia probands, 15 unrelated fathers of schizophrenia probands, 13 unrelated unaffected sibs of schizophrenia probands, and 211 unrelated unaffected control probands is shown in Table 13.

TABLE 13

DISTRIBUTION OF DHFR AND MTHFR MUTATION GENOTYPES AND ALLELES AMONG CONTROLS, SCHIZOPHRENICS, AND SCHIZOPHREMA FAMILY MEMBERS

| GenTyp | Schizophrenia | | | | Ctrl |
|---|---|---|---|---|---|
| | P | M | F | S | |
| DHFR 19 bp deletion polymorphism: | | | | | |
| 1/1 | 6 (.16) | 10 (.29) | 4 (.27) | 4 (.31) | 56 (.26) |
| 1/2 | 22 (.58) | 13 (.37) | 11 (.73) | 8 (.61) | 115 (.54) |
| 2/2 | 10 (.26) | 12 (.34) | 0 (0.0) | 1 (.08) | 40 (.19) |
| total | 38 (1.00) | 35 (1.00) | 15 (1.00) | 13 (1.00) | 211 (.99) |
| MTHFR 677C->T transition polymorphism: | | | | | |
| 1/1 | 14 (.37) | 16 (.46) | 11 (.73) | 4 (.31) | 103 (.49) |
| 1/2 | 18 (.47) | 18 (.51) | 3 (.20) | 8 (.61) | 78 (.37) |
| 2/2 | 6 (.16) | 1 (.03) | 1 (.07) | 1 (.08) | 30 (.14) |
| total | 38 (1.00) | 35 (1.00) | 15 (1.00) | 13 (1.00) | 211 (1.00) |

P = schizophrenia patients; M = mothers of schizophrenia patients; F = fathers of schizophrenia patients; S = unaffected sibs of schizophrenia patients; Ctrl = control individuals.

The four data files were analyzed using the logistic procedure of SAS (SAS Institute Inc., 1995) and the "descending" option, which modeled the probability that RESPONSE=1, that is, the probability that the proband was affected with schizophrenia. Note that the proband was not always the individual whose genotype data were used. For example, genotype data for mothers of schizophrenic probands were used to determine the probability that their children, the probands, were affected. Use of the "best" model selection options for logistic analysis in SAS gave the best models for two and three explanatory variables, (Table 14).

TABLE 14

BINARY LOGISTIC REGRESSION RESULTS

GENETIC RISK FACTOR
Odds Ratio (p, value)            MODEL: Ds Dd Ms Md

Schizophrenia Patients

Ds OR(p)    1.937 (.18)
Dd OR(p)    1.263 (.59)
Ms OR(p)    1.775 (.14)
Md OR(p)    0.914 (.86)

Mothers of Schizonhrenia Patients

Ds OR(p)    0.630 (.31)
Dd OR(p)    2.653 (.028)*
Ms OR(p)    1.439 (.34)
Md OR(p)    0.143 (.065)

TABLE 14-continued

BINARY LOGISTIC REGRESSION RESULTS

GENETIC RISK FACTOR
Odds Ratio (p, value)            MODEL: Ds Dd Ms Md

Fathers of Schizonhrenia Patients

Ds OR(p)    1.178 (.79)
Dd OR(p)    0.000 (.96)
Ms OR(p)    0.366 (.14)
Md OR(p)    0.841 (.88)

Unaffected Sibs of Schizophrenia Patients

Ds OR(p)    1.104 (.88)
Dd OR(p)    0.337 (.31)
Ms OR(p)    2.688 (.12)
Md OR(p)    0.317 (.29)

Notes For Table 14
DHFR 19 bp deletion:    Ds = single dose;    Dd = double dose
MTHFR 677C->T mutation:    Ms = single dose;    Md = double dose Logistic Regression Model Model with four explanatory variables (Ms, Md, Ds and Dd).

OR(p)=odds ratio and the corresponding p-value for that odds ratio determination *=significant at the $p \leq 0.05$ level.

0.000 odds ratios occurred since none of the fathers of schizophrenia patients had genotype Dd; there was a possibly quasi-complete separation in the sample points; the maximum likelihood estimate may not exist; and therefore validity of the model fit for these odds ratios was questionable.

The comparison of mothers of schizophrenia probands with control probands was statistically significant. Ds was not a significant genetic risk factor. Neither Ms nor Md in mothers was a significant genetic risk factor. However, the p-value for Md decreased and approached significance (p=0.065) at the $p \leq 0.05$ level.

Predicted Probabilities of the Various Genotypes: The "probs predicted" modality of SAS, gave the predicted probability that the proband was affected with schizophrenia (response=1) given genotype data for control probands and schizophrenia patients (probands), mothers of schizophrenia probands, fathers of schizophrenia probands, or sibs of schizophrenia probands. The maximum probabilities obtained are shown in Table 15. The highest maximum predicted probability that the proband was affected was obtained for genotype data from mothers of schizophrenia probands, next for schizophrenia probands, next for fathers of schizophrenia probands, and lowest for sibs of schizophrenia probands.

TABLE 15

MAXIMUM PREDICTED PROBABILITY

| Model | P | M | F | S |
|---|---|---|---|---|
| Ds Dd Ms Md | 0.24 | 0.29 | 0.12 | 0.11 |

Model and explanatory variables are the same as in Table 14.

Model and explanatory variables are the same as in Table 14.

Determination of Genotypes Conferring the Highest Risk: The predicted probabilities that the proband was affected with schizophrenia given specific genotypes of control probands and schizophrenia probands, mothers of schizophrenia probands, fathers of schizophrenia probands, or sibs of schizophrenia probands were determined using the model containing all four explanatory variables (Table 16). The predicted probabilities that the proband was affected with schizophrenia were highest for maternal genotypes (Table 15). The maternal genotype with the highest risk was Dd Ms, conferring a probability of 0.29 of schizophrenia in the proband (Table 16). The Dd Ms genotype also gave the highest predicted probability, 0.24, for schizophrenia patients.

TABLE 16

PREDICTED PROBABILITIES FOR SPECIFIC GENOTYPES
Model: Ds Dd Ms Md

| Genotype | Predicted Probability | Genotype | Predicted Probability |
|---|---|---|---|
| Schizophrenia Patients: | | | |
| Dnull + Mnull | 0.07 | Ds + Ms | 0.20 |
| Dnull + Ms | 0.12 | Ds + Md | 0.19 |
| Dnull + Md | 0.11 | Dd + Ms | 0.24 |
| Ds + Mnull | 0.12 | Dd + Md | 0.23 |
| Dd + Mnull | 0.15 | | |
| Mothers of Schizophrenia Patients: | | | |
| Dnull + Mnull | 0.16 | Ds + Ms | 0.13 |
| Dnull + Ms | 0.20 | Ds + Md | 0.02 |
| Dnull + Md | 0.03 | Dd + Ms | 0.29 |
| Dd + Mnull | 0.22 | Dd + Md | 0.06 |
| Ds + Mnull | 0.10 | | |
| Fathers of Schizophrenia Patients: | | | |
| Dnull + Mnull | 0.10 | Ds + Ms | 0.05 |
| Dnull + Ms | 0.04 | Ds + Md | 0.04 |
| Dnull + Md | 0.03 | Dd + Ms | 0.0 |
| Ds + Mnull | 0.12 | Dd + Md | 0.0 |
| Dd + Mnull | 0.0 | | |
| Unaffected Sibs of Schizophrenia Patients: | | | |
| Dnull + Mnull | 0.04 | Ds + Ms | 0.11 |
| Dnull + Ms | 0.10 | Ds + Md | 0.04 |
| Dnull + Md | 0.03 | Dd + Ms | 0.04 |
| Ds + Mnull | 0.04 | Dd + Md | 0.01 |
| Dd + Mnull | 0.02 | | |

Genotypes consist of the same explanatory variables described in Table 14 except that Dnull has no copy of the DHFR deletion and Mnull has no copy of the MTHFR 677C->T variant. Odds ratios of 0.0 were unsatisfactory as described in Table 14.

Discussion

Structure and Function of the DHFR 19 bp Deletion Polymorphism: DHFR polymorphisms have been reported previously [Feder et al., Nucl. Acids Res. 15:5906 (1987); Detera-Wadleigh et al., Nucl. Acids Res. 17:6432 (1989)]. It is known that introns are important for message regulation e.g., splicing, or as sites for binding transcription factors. Since the first intron is a relatively common location for regulatory elements, it is possible that the deleted region of DHFR intron 1 could play a role in regulation of DHFR or that the deletion could be a genetic risk factor for schizophrenia because it removes potential transcription factor binding sites. Abnormalities of transcription factors and their binding sites may play a role in disease. For example, a polymorphic Sp1 binding site in the collagen type I alpha 1 gene has been associated with reduced bone density and osteoporosis [Grant et al., Nature Genet. 14:203–205 (1996)].

The Nature of the Putative Folate Genetic Risk Factors for Schizophrenia: Dd in the mother of a schizophrenia proband conferred significantly increased risk of schizophrenia in her child (Table 14). The findings that Dd was a genetic risk factor in mothers but not fathers of schizophrenia probands (Table 15) and that Dd in mothers gave a higher predicted probability than in schizophrenia patients, fathers or sibs (Tables 15 and 16) was consistent with the role of DHFR as a teratogenic locus according to the gene-teratogen model (described above). The finding that a double dose but not a single dose of the DHFR deletion in mothers was a genetic risk factor (Table 16) supported a recessive mode of action in the mother. A teratogenic locus acting in the mother can also act as a modifying or specificity locus in the fetus.

Neither Ms nor Md in mothers of schizophrenia probands showed statistical significance as genetic risk factors for schizophrenia in probands (Table 14). However Md in mothers approached statistical significance (p=0.065) and appeared to be protective (odds ratio 0.14), while Ms in mothers appeared to increase risk modestly (odds ratio 1.44, p=0.34).

Role of Genetic and Environmental Factors in Schizophrenia: Since the probability that a schizophrenia co-twin is also affected is reported [Gottesman, Schizophrenia Genesis, Schizophrenia Genesis—The Origins of Madness, W. H. Freeman & Co. N.Y. (1991)] to be only 48%, a large part of the risk for schizophrenia would be anticipated to come from environmental factors. Therefore, some controls should have the genetic risk factors for schizophrenia but not be affected with schizophrenia. In the present data set, 6 of 35 schizophrenia mothers and 7 of 38 schizophrenia patients had Dd Ms, the genotype conferring the highest risk, compared with 15 of 211 controls. Since this genotype gave predicted probabilities of schizophrenia in probands of 0.29 and 0.24 respectively, polymorphisms of DHFR and MTHFR could account for a considerable portion of the genetic component of the risk of schizophrenia.

Relation of DHFR to Cytogenetic and Linkage Data for Schizophrenia: As discussed above, the DHFR gene has been located on chromosome 5 at 5q11.2–13.2. A schizophrenia translocation was reported (McGillivray et al. 1990; Bassett, 1992) affecting 5q11.2–5q13.3. Also two-point lod scores of 4.64 and 2.29 were found [Sherrington et al., Nature, 336:164–167 (1988)] for the polymorphic markers D5S76 and D5S39 respectively on chromosome 5, in this region [McGillivray et al., Am. J. Med. Genet., 35:10–13 (1990); Bassett, Br. J. Psychiatry, 161:323–334 (1992)]. Two other linkage studies found small positive lod scores in this region [Coon et al., Biol. Psychiatry, 34:277–289 (1993); Kendler and Diehl, Schizophr. Bull., 19:261–285 (1993)], but numerous other studies excluded this region under the assumptions and models used [Kendler and Diehl, Schizophr. Bull, 19:261–285 (1993)]. Recently, new studies have found suggestive evidence for a potential susceptibility locus at a different region of 5q, 5q31 [Schwab et al., Nat. Genet. 11:325–327 (1997)] and 5q22–31 [Straub et al., Molec Psychiatr. 2:148–155 (1997)].

The case-control study presented herein illustrates the usefulness of the DNA polymorphism-Diet-Cofactor-Development and the gene-teratogen models described above. More importantly, the results presented herein, clearly fail to reject the specific models, i.e., that folate gene polymorphisms can play a role in the etiology of schizophrenia.

The present invention is not to be limited in scope by specific embodiments described herein. Indeed, various modifications of the invention in addition to those described herein will become apparent to those skilled in the art from the foregoing description and the accompanying figures. Such modifications are intended to fall within the scope of the appended claims.

Various publications in addition to the immediately foregoing are cited herein, the disclosures of which are incorporated by reference in their entireties.

We claim:

1. A method of estimating the susceptibility of an individual to have offspring that develop a developmental disorder comprising:
   (a) collecting a biological sample from one or more participants; wherein a participant is either the individual or a blood relative of the individual; and wherein the biological sample contains nucleic acids and/or proteins of the participant;
   (b) analyzing the nucleic acids and/or proteins from the biological sample; wherein said analyzing results in a partial or full genotype for the alleles of two or more genes involved in folate, pyridoxine, and/or cobalamin metabolism; and wherein said partial or full genotype forms a dataset of genetic explanatory variables for the participants;
   (c) adding the datasets of genetic explanatory variables obtained from steps (a) and (b) to a genetic reference dataset therein forming a combined genetic dataset;
   (d) formulating a model comprising the genetic explanatory variables obtained from the participants; and
   (e) analyzing the combined genetic dataset by binary logistic regression;
   wherein a predicted probability for the individual to have offspring that develop a developmental disorder is determined; and wherein the genetic and environmental susceptibility of an individual to have offspring that develop a developmental disorder is estimated, and wherein the individual is a pregnant woman.

2. The method of claim 1 further comprising the step of:
   (f) modifying the model by adding or subtracting a genetic explanatory variable;

and re-analyzing the combined genetic dataset by binary logistic regression; wherein a model is chosen that best fits the data.

3. The method of claim 2 further comprising the step of:
(g) testing the model for goodness of fit.

4. A method of treating an asymptomatic individual determined by the method of claim 3 to be susceptible to have offspring that develop a developmental disorder comprising administering methylfolate, cobalamin or pyridoxine.

5. A method of lowering the risk of a pregnant woman who has been determined by the method of claim 3 to be susceptible to have offspring that develop a developmental disorder comprising administering methylfolate, cobalamin or pyridoxine to the pregnant woman, wherein said administering lowers the risk of the pregnant woman of giving birth to offspring with a developmental disorder.

6. A method of determining if any treatment is advisable for a pregnant woman who has been determined by the method of claim 3 to be susceptible to having offspring that develop a developmental disorder comprising determining the concentration of a risk factor from a tissue sample or body fluid from the pregnant woman; wherein when the concentration of the risk factor is statistically above or below an accepted normal range, treatment is advisable.

7. A method of monitoring the effect of the administration of methylfolate, cobalamin or pyridoxine to the pregnant woman of claim 6, comprising determining the concentration of a risk factor from a tissue sample or body fluid from the pregnant woman; and wherein when the concentration of the risk factor is statistically within an accepted normal range, the treatment is effective.

8. The method of claim 7 wherein the risk factor is selected from the group consisting of homocysteine, folate, and cobalamin.

* * * * *

SEQUENCE LISTING

<160> NUMBER OF SEQ ID NOS: 46

<210> SEQ ID NO 1
<211> LENGTH: 2187
<212> TYPE: DNA
<213> ORGANISM: Homo sapiens

<400> SEQUENCE: 1

```
gccatggtga acgaagccag aggaaacagc agcctcaacc cctgcttgga gggcagtgcc      60
agcagtggca gtgagagctc caaagatagt tcgagatgtt ccaccccggg cctggacccct    120 gagcggcatg agagactccg ggagaagatg aggcggcgat tggaatctgg tgacaagtgg     180
ttctccctgg aattcttccc tcctcgaact gctgagggag ctgtcaatct catctcaagg     240
tttgaccgga tggcagcagg tggccccctc tacatagacg tgacctggca cccagcaggt    300
gaccctggct cagacaagga gacctcctcc atgatgatcg ccagcaccgc cgtgaactac    360
tgtggcctgg agaccatcct gcacatgacc tgctgccgtc agcgcctgga ggagatcacg    420
ggccatctgc acaaagctaa gcagctgggc ctgaagaaca tcatggcgct gcggggagac    480
ccaataggtg accagtggga agaggaggag ggaggcttca actacgcagt ggacctggtg    540
aagcacatcc gaagtgagtt tggtgactac tttgacatct gtgtggcagg ttaccccaaa    600
ggccaccccg aagcagggag ctttgaggct gacctgaagc acttgaagga gaaggtgtct    660
gcgggagccg atttcatcat cacgcagctt ttcctttgagg ctgacacatt cttccgcttt    720
gtgaaggcat gcaccgacat gggcatcact tgccccatcg tccccgggat cttccccatc    780
cagggctacc actcccttcg gcagcttgtg aagctgtcca agctggaggt gccacaggag    840
atcaaggacg tgattgagcc aatcaaagac aacgatgctg ccatccgcaa ctatggcatc    900
gagctggccg tgagcctgtg ccaggagctt ctggccagtg gcttggtgcc aggcctccac    960
ttctacaccc tcaaccgcga gatggctacc acagaggtgc tgaagcgcct ggggatgtgg   1020
actgaggacc ccaggcgtcc cctaccctgg gctctcagtg cccacccccaa gcgccgagag  1080 gaaatgtac gtcccatctt ctgggcctcc agaccaaaga gttacatcta ccgtacccag   1140
gagtgggacg agttccctaa cggccgctgg ggcaattcct cttcccctgc ctttggggag  1200
ctgaaggact actacctctt ctacctgaag agcaagtccc caaggagga gctgctgaag   1260 atgtgggggg aggagctgac cagtgaagca agtgtcttg aagtctttgt tctttacctc   1320
tcgggagaac caaaccggaa tggtcacaaa gtgacttgcc tgccctggaa cgatgagccc   1380
ctggcggctg agaccagcct gctgaaggag gagctgctgc gggtgaaccg ccagggcatc  1440
ctcaccatca actcacagcc caacatcaac gggaagccgt cctccgaccc catcgtgggc   1500
tggggcccca gcggggggcta tgtcttccag aaggcctact tagagttttt cacttcccgc  1560
gagacagcgg aagcacttct gcaagtgctg aagaagtacg agctccgggt taattaccac  1620
cttgtcaatg tgaagggtga aaacatcacc aatgcccctg aactgcagcc gaatgctgtc   1680
acttggggca tcttccctgg gcgagagatc atccagccca ccgtagtgga tcccgtcagc  1740
ttcatgttct ggaaggacga ggcctttgcc ctgtggattg agcggtgggg aaagctgtat  1800
```

-continued

| | |
|---|---|
| gaggaggagt cccgtcccg caccatcatc cagtacatcc acgacaacta cttcctggtc | 1860 |
| aacctggtgg acaatgactt cccactggac aactgcctct ggcaggtggt ggaagacaca | 1920 |
| ttggagcttc tcaacaggcc cacccagaat gcgagagaaa cggaggctcc atgaccctgc | 1980 |
| gtcctgacgc cctgcgttgg agccactcct gtcccgcctt cctcctccac agtgctgctt | 2040 |
| ctcttgggaa ctccactctc cttcgtgtct ctcccacccc ggcctccact ccccacctg | 2100 |
| acaatggcag ctagactgga gtgaggcttc caggctcttc tggacctga gtcggcccca | 2160 |
| catgggaacc tagtactctc tgctcta | 2187 |

<210> SEQ ID NO 2
<211> LENGTH: 7122
<212> TYPE: DNA
<213> ORGANISM: Homo sapiens

<400> SEQUENCE: 2

| | |
|---|---|
| gcgcgtgtct ggctgctagg ccgacaccaa ggactggccg ggtacccggg aagaaagcac | 60 |
| gtgctccagc agttgccgcg cccagccccg agagaggccc tagggcgctg cgggctttcg | 120 |
| gggtccgcag tccccccgcg acgcgagcca acggggaggc tcaaaagacc cgggccttgt | 180 |
| gtggcaggct cgcctggcgc tggctggcgt ggcccttggc cgtcgtcacc tgtggagagc | 240 |
| acgtcttctc tgccgcgccc tctgcgcaag gaggagactc acaacatgt cacccgcgct | 300 |
| ccaagacctg tcgcaacccg aaggtctgaa gaaaaccctg cgggatgaga tcaatgccat | 360 |
| tctgcagaag aggattatgg tgctggatgg agggatgggg accatgatcc agcgggagaa | 420 |
| gctaaacgaa gaacacttcc gaggtcagga atttaaagat catgccaggc cgctgaaagg | 480 |
| caacaatgac attttaagta taactcagcc tgatgtcatt taccaaatcc ataaggaata | 540 |
| cttgctggct ggggcagata tcattgaaac aaatacttttt agcagcacta gtattgccca | 600 |
| agctgactat ggccttgaac acttggccta ccggatgaac atgtgctctg caggagtggc | 660 |
| cagaaaagct gccgaggagg taactctcca gacaggaatt aagaggtttg tggcaggggc | 720 |
| tctgggtccg actaataaga cactctctgt gtccccatct gtggaaaggc cggattatag | 780 |
| gaacatcaca tttgatgagc ttgttgaagc ataccaagag caggccaaag gacttctgga | 840 |
| tgcgggggtt gatatcttac tcattgaaac tattttttgat actgccaatg ccaaggcagc | 900 |
| cttgtttgca ctccaaaatc ttttttgagga gaaatatgct ccccggccta tctttatttc | 960 |
| agggacgatc gttgataaaa gtgggcggac tctttccgga cagacaggag agggatttgt | 1020 |
| catcagcgtg tctcatggag aaccactcta cattggatta aattgtgctt tgggtgcagc | 1080 |
| tgaaatgaga ccttttattg aaataattgg aaaatgtaca acagcctatg tcctctgtta | 1140 |
| tcccaatgca ggtcttccca caccctttgg tgactatgat gaaacgcctt ctatgatggc | 1200 |
| caagcaccta aaggattttg ctatggatgg cttggtcaat atagttggag atgctgtgg | 1260 |
| gtcaacacca gatcatatca gggaaattgc tgaagctgtg aaaaattgta agcctagagt | 1320 |
| tccacctgcc actgcttttg aaggacatat gttactgtct ggtctagagc ccttcaggat | 1380 |
| tggaccgtac accaactttg ttaacattgg agagcgctgt aatgttgcag gatcaaggaa | 1440 |
| gtttgctaaa ctcatcatgg caggaaacta tgaagaagcc ttgtgtgttg ccaaagtgca | 1500 |
| ggtggaaatg ggagcccagg tgttggatgt caacatggat gatggcatgc tagatggtcc | 1560 |
| aagtgcaatg accagatttt gcaacttaat tgcttccgag ccagacatcg caaaggtacc | 1620 |
| tttgtgcatc gactcctcca atttgctgt gattgaagct gggttaaagt gctgccaagg | 1680 |
| gaagtgcatt gtcaatagca ttagtctgaa ggaaggagag gacgacttct tggagaaggc | 1740 |

-continued

```
caggaagatt aaaaagtatg gagctgctat ggtggtcatg gcttttgatg aagaaggaca    1800
ggcaacagaa acagacacaa aaatcagagt gtgcacccgg gcctaccatc tgcttgtgaa    1860
aaaactgggc tttaatccaa atgacattat ttttgaccct aatatcctaa ccattgggac    1920
tggaatggag gaacacaact tgtatgccat taattttatc catgcaacaa agtcattaa    1980 agaaacatta cctggagcca gaataagtgg aggtcttcc aacttgtcct tctccttccg    2040
aggaatggaa gccattcgag aagcaatgca tggggttttc ctttaccatg caatcaagtc    2100
tggcatggac atgggatag tgaatgctgg aaacctccct gtgtatgatg atatccataa    2160
ggaacttctg cagctctgtg aagatctcat ctggaataaa gaccctgagg ccactgagaa    2220
gctcttacgt tatgcccaga ctcaaggcac aggagggaag aaagtcattc agactgatga    2280
gtggagaaat ggccctgtcg aagaacgcct tgagtatgcc cttgtgaagg gcattgaaaa    2340
acatattatt gaggatactg aggaagccag gttaaaccaa aaaaaatatc cccgacctct    2400
caatataatt gaaggacccc tgatgaatgg aatgaaaatt gttggtgatc tttttggagc    2460
tggaaaaatg tttctacctc aggttataaa gtcagcccgg gttatgaaga aggctgttgg    2520
ccaccttatc cctttcatgg aaaaagaaag agaagaaacc agagtgctta acggcacagt    2580
agaagaagag gacccttacc agggcaccat cgtgctggcc actgttaaag gcgacgtgca    2640
cgacataggc aagaacatag ttggagtagt ccttggctgc aataatttcc gagttattga    2700
tttaggagtc atgactccat gtgataagat actgaaagct gctcttgacc acaaagcaga    2760
tataattggc ctgtcaggac tcatcactcc ttccctggat gaaatgattt ttgttgccaa    2820
ggaaatggag agattagcta taaggattcc attgttgatt ggaggagcaa ccacttcaaa    2880
aacccacaca gcagttaaaa tagctccgag atacagtgca cctgtaatcc atgtcctgga    2940
cgcgtccaag agtgtggtgg tgtgttccca gctgttagat gaaaatctaa aggatgaata    3000
ctttgaggaa atcatggaag aatatgaaga tattagacag gaccattatg agtctctcaa    3060
ggagaggaga tacttaccct taagtcaagc cagaaaaagt ggtttccaaa tggattggct    3120
gtctgaacct cacccagtga agcccacgtt tattgggacc caggtctttg aagactatga    3180
cctgcagaag ctggtggact acattgactg gaagcctttc tttgatgtct ggcagctccg    3240
gggcaagtac ccgaatcgag gctttcccaa gatatttaac gacaaaacag taggtggaga    3300
ggccaggaag gtctacgatg atgcccacaa tatgctgaac acactgatta gtcaaaagaa    3360
actccgggcc cggggtgtgg ttgggttctg gccagcacag agtatccaag acgacattca    3420
cctgtacgca gaggctgctg tgccccaggc tgcagagccc atagccacct tctatgggtt    3480
aaggcaacag gctgagaagg actctgccag cacggagcca tactactgcc tctcagactt    3540
catcgctccc ttgcattctg gcatccgtga ctacctgggc ctgtttgccg ttgcctgctt    3600 tgggggtagaa gagctgagca aggcctatga ggatgatggt gacgactaca gcagcatcat    3660
ggtcaaggcg ctgggggacc ggctggcaga ggcctttgca gaagagctcc atgaaagagt    3720
tcgccgagaa ctgtgggcct actgtggcag tgagcagctg gacgtcgcag acctgcgcag    3780
gctgcggtac aagggcatcc gcccggctcc tggctacccc agccagcccg accacaccga    3840
gaagctcacc atgtggagac tcgcagacat cgagcagtct acaggcatta ggttaacaga    3900
atcattagca atggcacctg cttcagcagt ctcaggcctc tacttctcca atttgaagtc    3960
caaatatttt gctgtgggga agatttccaa ggatcaggtt gaggattatg cattgaggaa    4020
gaacatatct gtggctgagg ttgagaaatg gcttggaccc attttgggat atgatacaga    4080
```

-continued

```
ctaacttttt tttttttgc ctttttatt cttgatgatc ctcaaggaaa tacaacctag      4140
ggtgccttaa aaataacaac aacaaaaaac ctgtgtgcat ctggctgaca cttacctgct      4200
tctggttttc gaagactatt tagtggaacc ttgtagagga gcaggtctt cctgcagtgc      4260 ctggaaaaca ggcgctgttt ttttgggacc ttgcgtgaag agcagtgagc agggttcctg      4320
tggtttccct ggtccctctg agatggggac agactgaaga cagaggtcgt ttgatttcaa      4380
agcaagtcaa cctgcttttt tctgttttta cagtggaatc taggaggcca cttagtcgtc      4440
tttttttcct cttagaagaa aagcctgaaa ctgagttgaa tagagaagtg tgaccctgtg      4500
acaaaatgat actgtgaaaa atggggcatt ttaatctaag tggttataac agtggattct      4560
gacggggaag gtgtagctct gttctcttcg gaagacctcg ttttctaaag gctggactaa      4620
atggctgcag aactcccttt ggcaaaaggc atgcgctcac tgcttgcttg tcagaaacac      4680
tgaagccatt tgccccagtg tggtcaagca gccatgcttt ctgggcattt tcgtcctccc      4740
ataatttcat atttccgtac ccctgaggaa acaaaaagga aatgaggaga gaaagttact      4800
gttaagggtg gttaacattt tttttgtttt gttttgtttt ggttttttt ttttgagaca      4860 gagtctggcc ctgtcgccca ggctggagtg caggggcgca atctcggctc atagcaagct      4920
ccgcctcctg ggttcatgcc attctcctgc ctcagcctcc agagtagctg ggactacagg      4980
tgcccaccac cacacccggc taattttttg tgttttaca aaatacaaaa aagtagagac      5040
aggatttcac tgtgttagcc aggatggtct tgatctcccg acctcgtgat ctgcccacct      5100
cagcctccca aaatgctggg attacaggcg tgagccaccg agcctggccg gttaacatct      5160
tttaattgtt tccaggattg agcaggttct cagctgggct ctgatatccc gtgcggagtt      5220
ggacaagtgg gcagcataaa gtcactcatt tcttaccatt ttattcccct caattctcaa      5280
tatattcagt aatgaagaat ggtgccacca ctcaagcaac aagcctcaaa ctcaaccatg      5340
tcatcttttt cttggatgat tgcagttatt tcaaaaattt gcatgcaaaa tatacactca      5400
tcctacttca agatggtggt ggcaatagtc aggagaaggt aacattggag tcctggtttg      5460
attcgaagga tgaagacgaa gaagcaaggg aggaacaaat gaagaaccat ctttgttcat      5520
gaataggaat attcaagatt ataaaggtat caggtctcct aaaattgatc tatggattta      5580
ataccatttt caatggaaat tccaacagat tttattgaat gaaacaagca ggtgtttata      5640
tggagtagca aaggacttaa aattaccaaa tgcttctaaa tatgaaggag aggttgggga      5700
cacgcaccct atgtgatacc aagttttatt gtcaagacag tgtcatggtg cagaggtagg      5760
cattctgagc aggggaacaa aataagggcc tagaaactca cccgtgcata tgttgacctt      5820
tgcaaaatga cctggtgaca tggcaagtca gtggggacag gaaggaccac tccctaagta      5880
atcccagaac aatggctatt catgtgggaa aaaagaaat tttactttct ctcaccttac      5940
ctggtgataa gttccaaata tgttaagggc tttaatacaa aaagcaaaaa ttgtcagtgt      6000
ttggatgaaa aaagccttag ggcaggaaag aatctcttga acataaagt agtaatcata      6060 aaggacaaga tggttaagtc aattctgtta aaactcaagg cttatattaa gcaaacactt      6120
gaagtgagaa gatgatccac aacttgagaa gacatttata atacaaataa ctgatgaagg      6180
attcataatc acaaatatag agaattccta tttaaaaaaa tagaaaaata gtgaagacta      6240
cacaagagga aataggggctt ttaaataaat agatgttctg tagcattggt cagggaaata      6300
tgaattagga ccacaatgag attccatttt atatccataa gatttgcaaa ggttgggtct      6360
gacagtacca gttgttagat ctgtagggac ttgtacaaca ttgtggatgt gtaaacaggc      6420
accactgctt taaaaaacaa ttatcccctta cagacttgaa catttgcaga cgttatgatc      6480
```

-continued

```
ttgcttccaa ctcccacctg tatgtccagc aaactcttgc atgtggccac taggaggaat   6540
gtgtaagaat gttcatagtt acatatttat aatagttaat aactggaaaa agtgaaatgt   6600
atgtctgtct acaggaaaat aggtgaataa ttagatatat atattcattc tacgggatat   6660
tattcagtag tggaaatgag tgaactacag ctatacctca caataagaat gaatctcaga   6720
aaatattaag gaaaaaagca agtttgaaga gaccacatgg ggcgtactat ttttattggg   6780
cccaaaaaca agcaaaacca agaatatgt agtctaagca tacgtataca ataaaactat    6840
gctattaaaa aaaaaggta actgataaac caaaattgag catagtaatt acccacagaa    6900
ggaggaagtg gaagggacag gagcacatag gtagatgcca agttatgcag ctgttctggt   6960
tcctcctggt aggcttacaa gtgtttacta tatgctatta atacattata ctttataact   7020
aatagataac agttttttac atattaaata tgttctactt aaatatatta taaaaaataa   7080
aggcaaagtg gaatgtttaa aaaaaaaaaa aaaaaaaaaa aa                       7122

<210> SEQ ID NO 3
<211> LENGTH: 564
<212> TYPE: DNA
<213> ORGANISM: Homo sapiens

<400> SEQUENCE: 3
atggttggtt cgctaaactg catcgtcgct gtgtcccaga acatgggcat cggcaagaac     60
ggggacctgc cctggccacc gctcaggaat gaattcagat atttccagag aatgaccaca    120
acctcttcag tagaaggtaa acagaatctg gtgattatgg gtaagaagac ctggttctcc    180
attcctgaga gaatcgacc tttaaagggt agaattaatt tagttctcag cagagaactc    240
aaggaacctc cacaaggagc tcattttctt tccagaagtc tagatgatgc cttaaaactt    300
actgaacaac cagaattagc aaataaagta gacatggtct ggatagttgg tggcagttct    360
gtttataagg aagccatgaa tcacccaggc catcttaaac tatttgtgac aaggatcatg    420
caagactttg aaagtgacac gttttttcca gaaattgatt tggagaaata taaacttctg    480
ccagaatacc caggtgttct ctctgatgtc caggaggaga aaggcattaa gtacaaattt    540
gaagtatatg agaagaatga ttaa                                          564

<210> SEQ ID NO 4
<211> LENGTH: 2158
<212> TYPE: DNA
<213> ORGANISM: Homo sapiens

<400> SEQUENCE: 4
gcgcggcata acgacccagg tcgcggcgcg gcggggcttg agcgcgtggc cggtgccgca     60
ggagccgagc atggagtacc aggatgccgt gcgcatgctc aatacccctgc agaccaatgc   120 cggctacctg gagcaggtga agcgccagcg gggtgaccct cagacacagt ggaagccat    180 ggaactgtac ctggcacgga gtgggctgca ggtggaggac ttggaccggc tgaacatcat   240
ccacgtcact gggacgaagg ggaagggctc cacctgtgcc ttcacggaat gtatcctccg   300
aagctatggc ctgaagacgg gattctttag ctctccccac ctggtgcagg ttcgggagcg   360
gatccgcatc aatgggcagc ccatcagtcc tgagctcttc accaagtact ctgtgcgcct   420
ctaccaccgg ctggaggaga ccaaggatgg cagctgtgtc tccatgcccc cctacttccg    480
cttcctgaca ctcatggcct tccacgtctt cctccaagag aaggtggacc tggcagtggt   540
ggaggtgggc attggcgggg cttatgactg caccaacatc atcaggaagc ctgtggtgtg   600
```

-continued

```
cggagtctcc tctcttggca tcgaccacac cagcctcctg ggggatacgg tggagaagat      660
cgcatggcag aaaggggggca tctttaagca aggtgtccct gccttcactg tgctccaacc     720
tgaaggtccc ctggcagtgc tgagggaccg agcccagcag atctcatgtc ctctatacct     780
gtgtccgatg ctggaggccc tcgaggaagg ggggccgccg ctgaccctgg gcctggaggg     840
ggagcaccag cggtccaacg ccgccttggc cttgcagctg ccccactgct ggctgcagcg     900
gcaggaccgc catggtgctg gggagccaaa ggcatccagg ccagggctcc tgtggcagct     960
gcccctggca cctgtgttcc agcccacatc ccacatgcgg ctcgggcttc ggaacacgga    1020
gtggccgggc cggacgcagg tgctgcgcg cgggcccctc acctggtacc tggacggtgc     1080
gcacaccgcc agcagcgcgc aggcctgcgt gcgctggttc cgccaggcgc tgcagggccg    1140
cgagaggcca agcggtggcc ccgaggttcg agtcttgctc ttcaatgcta ccggggaccg    1200
ggacccggcg gccctgctga agctgctgca gccctgccag tttgactatg ccgtcttctg    1260
ccctaacctg acagaggtgt catccacagg caacgcagac caacagaact tcacagtgac    1320
actggaccag gtcctgctcc gctgcctgga acaccagcag cactggaacc acctggacga    1380
agagcaggcc agcccggacc tctggagtgc cccagcca gagcccggtg ggtccgcatc       1440
cctgcttctg gcgccccacc caccccacac ctgcagtgcc agctccctcg tcttcagctg    1500
catttcacat gccttgcaat ggatcagcca aggccgagac ccatcttcc agccacctag      1560
tcccccaaag ggcctcctca cccaccctgt ggctcacagt ggggccagca tactccgtga    1620
ggctgctgcc atccatgtgc tagtcactgg cagcctgcac ctggtgggtg gtgtcctgaa    1680
gctgctggag cccgcactgt cccagtagcc aaggcccggg gttggaggtg ggagcttccc    1740
acacctgcct gcgttctccc catgaactta catactaggt gccttttgtt tttggctttc    1800
ctggttctgt ctagactggc ctaggggcca gggctttggg atgggaggcc gggagaggat    1860
gtcttttta aggctctgtg ccttggtctc tccttcctct tggctgagat agcagagggg      1920
ctccccgggt ctctcactgt tgcagtggcc tggccgttca gcctgtctcc cccaacaccc    1980
cgcctgcctc ctggctcagg cccagcttat tgtgtgcgct gcctggccag gccctgggtc    2040
ttgccatgtg ctgggtggta gatttcctcc tcccagtgcc ttctgggaag ggagagggcc    2100
tctgcctggg acactgcggg acagagggtg gctggagtga attaaagcct tgtttttt     2158
```

<210> SEQ ID NO 5
<211> LENGTH: 7720
<212> TYPE: DNA
<213> ORGANISM: Homo sapiens

<400> SEQUENCE: 5

```
taagttgaca cttctcaggt tgtcacaaga ttcaggtatg gctcactgtt gcaggacata      60
agctgggatc tcctgggaat tggtctgctt gcaggcccta gagagccttc cttcttggtt    120
gattttcctc tagagatcca actgtcttct caggctcccc tgcctgcctc ctccttgggt    180
cctttcttgt ggcattgcca gattactggg cccccatttt ccctacactt actgccactc    240
atagtctgat ggttcccaca tctgcatcca acctggactc ttcccctgag ctttccctc     300
tacaaccacc ttccccgggc caagggcaca caggcacctc gacaaaacag tgttctatgt    360
ttcttcctgc ccaaacctgc ccctcccctct cccttttccc atctgtggta ccaccatggg    420
ctcagagaat aaaaaaaatg aaggcttctg tcattgactg gggtggagat ggaggggaaga   480
gttagcccag aatcacaggt gctgtagaaa ggataccctga gttgccggga gaggggtcc    540
atgagttggg gatggaagga gagcttggcc cttcaaacaa ttgaagatct gatcaaaaga    600
```

```
ttcagaacat ctgtgatttt gtggctggtg atgggtgaca cctgggctaa tggggttggg      660
ggagttggtg gctctacaat ttatggcctt gggagatcct tgctctctat agctgactgg      720
gaggttggaa gcctgggctc tagcccttgc cttgatcctc cggatctcat tttcctcatc      780
tgcctaacag gacagagggg ttggaaactg atgagattag ctcaaaggat cctggcagct      840
caggctgcaa gattttttc agacctcagt gtttgggaaa aaattgggta ggtgagctt        900 agggactggc cttaggcctg cactgttaat tcaccccctc ccactacccc atggaggcct     960
ggctggtgct cacatacaat aattaactgc tgagtggcct tcgcccaatc ccaggctcca     1020
ctcctgggct ccattcccac tccctgcctg tctcctaggc cactaaacca cagctgtccc    1080
ctggaataag gcaagggga gtgtagagca gagcagaagc ctgagccaga cggagagcca      1140
cctcctctcc caggtatgtg acactcccca tcccccttca gaggccacac accctatggc     1200
attcccacca tgtgttaagg attttctgaa ctggaagggc cctctgtttg cctgaaggcc     1260
agagaatctt gaagtggaga ctgaggccca gaccagagtg tggcctgctc aagattaaac    1320
gacaagttag tgttcatccc cctgaactag tacctgggct ctagcccttc agtccagagc     1380
tgagttctca gctcttctag tctggggccc caaggttggg tgtgggggtc atgattgttg     1440
gtggggaggg gtcacagctg gactaagacc tgaaggtgag actaggcagg tgggaaagga   1500
gcttgcagag tgatgctgct caaaaggaca ggaagagagc ctggcttcag aagcagccac   1560
agcaagagag actactgact gaacaggtgg gctccactgg gggctccgga aaggattttc    1620
tcagccccca tccccagcac tgtgtgttgg ccgcacccat gagagcctca gcactctgaa    1680
ggtgcagggg gcaaaggcca aaagagctct ggcctgaact tgggtggtcc ctactgtgtg    1740
acttggggca tggccctcat ctgtgctgaa atgattccac aaagattaaa ctggctatca    1800
tttgttgatt tccccttct tacatttaat ccttgcagga gaaagctaag cctcaagata    1860
gtttgcttct ctttccccca aggccaagga gaaggtggag tgagggctgg ggtcgggaca    1920
ggttgaacgg gaaccctgtg ctctaaacag ttagggtttg ttcccgcagg aactgaaccc    1980
aaaggatcac ctggtattcc ctgagagtac agatttctcc ggcgtggccc tcaaggttag    2040
tgagtgagca ggtccacagg ggcatgattg gatcctggaa tgaatgaatc aaccatgaga   2100
gagtgaatga acactggaat caatagagta gcagagtaat ggattgtgga gcaggaaaga   2160
gagctgctgg gtgggaattc aattccaggc ttatatgagc cctgctgtgc agtcggcctg    2220
gagacagccc agctcaggcc ctgcctagac ccctgtcaag gaggccctgt caagaggaga   2280
ggaggggcag cacggggggca aggcaagctt gtgagcggga aaggcatgtc cactttagcg    2340
actggtatgt ggaagatgag ttagaggaga cagatggaga gaagtcatag gaaataaatt   2400
ctgagcattt taggagggcc cagacacctg tgtccagtg gagtgaagga aacagtcgcc    2460
tcccaaaatt cagtgtctga ggtcaaagga ttgaagttct gtgatgacca aggagaagcc   2520
agctctgtgg tagggggcac aggagctccc caaggcccca gggctgtcca gctggctgtc   2580
ccctgccagc acccatgtcc tgtgacccca ccccaccaag atcccatggt tccgggaag    2640 ggcctactaa actagcttga gtgatgaggc tagaaagggg ctgggaccaa ggtttaaaaa    2700 gcaaacaaa ctaacaaaaa ccacactgca gccccccaa ctaaaacatt tttataaact      2760
tttttttttt ttttgagatg gagtctcgct ctgtcaccca ggctagagtg caatggcaca    2820
atcttggctc actgtaacct ccacctcctg gattcaagtg attctcctgc ctcagcctcc    2880
cacgtagctg ggactacagg cacacgacac cgcacccagc tcatttttgta tttttagtag    2940
```

-continued

```
agacagggtt tcactatgtt ggccaggctg gtctcaaact tctgacctca ggtgatccac    3000
ccacctcagc cttccaaagt gctgggatta caggcatgag ccaccgcgcc cagcccattt    3060
ttgtaaactt ttacaatgaa gtaatttggt gtcaaaatct gacctgaaaa ttaatgtgag    3120
tttatgtata gttttaattt atcccactag tgtaactgtt tcaccccaga atatacactt    3180
gattattggg tatatgaaaa aaatattttc tttgaatcac ctttgatgaa atcctaaaaa    3240
attttaaccc tgaaacattt gaataaggca ttgtggacct atggcaaact cctggctatt    3300
tctgcatttt gcccaaatcc atccttgaat tatatcacct gaacctcgtg accacctgga    3360
gaaggcaatg aggctcaagc cagggagggg tggtgtctaa tcctaccttt cattggatct    3420
gggaaaactg agggagatgg gggcagggct ctatctgccc caggcttccg tccaggcccc    3480
accctcctgg agccctgcac acaacttaag gccccacctc cgcattcctt ggtgccactg    3540
accacagctc tttcttcagg gacagacatg gctcagcgga tgacaacaca gctgctgctc    3600
cttctagtgt gggtggctgt agtagggag gctcagacaa ggattgcatg ggccaggact    3660
gagcttctca atgtctgcat gaacgccaag caccacaagg aaaagccagg ccccgaggac    3720
aagttgcatg agcaggtggg ccaggggtg atctggggtg gtgagggact ggctcaggaa    3780
gaggaaacga ggacatggaa atgccaaacc ccattggcac tggtgaactg aagtggagga    3840
gcccttcagt ttgcattaat atgggtgact tatttcagag acactgtgcc aaatgtcggt    3900
acaatgccaa cagttcacct tcttggttgt tgagtttccg cattacagaa ataaggaagc    3960
aggcccaaag gagagcctgg gaaatgaagt tggagtgacc catcctgggg ttgcttgatt    4020
tagggattta gactgggaat gactcctcca aagatctgag ggaagaaact gcacactgtg    4080
catagtggcc tcttttctgc cagccctaaa cagctcaaga agggagagtc tctcacatta    4140
tgaggctgtg tgcaaagcat tctttttttt ttttcctgag acaaagtctc catatgttgc    4200
ccaggctggt ctcaaattcc tggactcaag tgatcctccc acctcagccc tcccaaagtg    4260
tgggattaca gaaatgagcc gtacgccctc ctgaagcatc ttggttcatg catctcgcaa    4320
aactttgggc tgtgtctctc gaccacattg gacctgaggt ctccctataa catttatttt    4380
gctaccaccc ctttaatatc ctgaacatga tgatataact aaagaaaaag cagaggaaaa    4440
gtaatttgta ggccaggtgt tacggctcac gcctgtaatc ccaacactgt gggatgtcga    4500
gatgggcaga tcacttgagc tcaggagttc gagaccagcc tgggcaagat ggcaaaaccc    4560
catctctact aaaaaataaa aaaaattagt caggtgtggt ggcacatgcc tgcagtccca    4620
gctactcagg aggctgaggt gggcaggtca gttgagccca ggaggcagag attgtagatc    4680
gtgccactgc actccagcct gggcaacaga gtgagacctt gtcaaaagaa agaaagaacg    4740
aaaaaaagaa agaaaggaag gaaggaaggg gaggaaggaa agggagggag gaaagggagg    4800
gaggaaaggg agggaggcaa gggagagaaa cttgtaatac gcatttcttt ttttttttct    4860
tgagatagag ttttgctctt gttgcccagg gtggatggca gtggcacaat ctcagctcac    4920
tgcaacctcc acctcccagg ttcaagtgat tctcctgcct cagcctcctg agtaggcaca    4980
cgccaccaca cccagctaat ttttttgttg tttgtttgtt ttgtttgttg gtattttag    5040
tagagatggg ggtttcacca tgttggccag gctggtctcg aactcctcac ctcataatcc    5100
gcccctcttg gcctcccaaa gtgctgagat tacaggtgtg agccactgcg cccggcctta    5160
agtgcacatt ttatttattt atttatttat ttatttattg agatggagtc ttgctctgtt    5220
gcccaggctg gagtgcagtg gcacaatctc agctcactgc aacctccacc tcccaggttc    5280
aagcaattct tctgccttgg cctccagagt agctgggact ataggcacct gccaccatgc    5340
```

```
ctagctaatt tttgtatttt tagtagaaat ggggttttgc catgttggcc aggctggtct    5400
ccattcttga ccttaagtga tctgtccacc tccacctccc aaagtgctgg gattacaggc    5460
actatgtgag ccactgtgcc ggcccacatt ttaatattta gcttgtcagc cttaagtaat    5520
gagattcagg aagcttgagg ataggcacac aggagcatag tttcaagttg tcctgaattt    5580
tgcagccatc acaagttagt ttttaaggaa aaagattagt tcctaagttg tttctcaata    5640
acttataata aaataacatc cacaattgat tggctataca ttgttttttt gtatcacaaa    5700
ttccacaaac agataatggg tgaggcagct agtcagggac aaaacacttc caagtagct    5760 gggattacag gtgtccgcca ccacacttgg ctagttttt gtttgtttat tttttgagat    5820
ggagtcttgc tctgtcgccc aggctggagt gcagtggcat gatctcggct cactgcaagc    5880
tccacctgcc gggttcacac cattctcctg cctcagcctc caagtagct gggactacag    5940 gtgccagcca ccacgcccgg ctaatttttt gtatttttag tagagacggg gtttcaccat    6000
gttggccagg atggtcttga tctcttagcc tcgtgatcca cccgcctcgg cctcccaaaa    6060
tgctgggatt acaggcgtga gccaccgcac ccggcctaat ttttatattt ttagtagaga    6120
cggggtttca ccatgttggc caggctggtc tcaaactctt gatctcaggt gatccacctg    6180
ccttggcctc ccaaagtgct gggattacac aagtaagcca ctgcacccag cctgggtta    6240 caatttaaat tgcttttta ccttcaaatc tttgacacct cagtgaggct taatctgacc    6300
gcactattac actacaagtc cccatccgtc tctgcttaat ttttgtccaa agcaaaaatc    6360
aggtgatgtg ttcattgttg taacccccagt ttctacaaaa gtacctgggt gagagtaagt    6420
aggatctcaa taaaggttga attaacaaat tttgtaatga ctgcaactcc agcaggagct    6480 ccctttggg ctcccactgt ctctgacggc cctctcccct aaagaggtcc caatagcaag    6540
tattttcctg ggtgacttcc agtgggctgg ggaatcaagg actaagaggg gagacactgc    6600
atgtggaata ttctggctgt gctggctgtg ctggctgtgg actgagtcct ctgtcttccc    6660
ccatccagtg tcgaccctgg aggaagaatg cctgctgttc taccaacacc agccaggaag    6720
cccataagga tgtttcctac ctatatagat tcaactggaa ccactgtgga gagatggcac    6780
ctgcctgcaa acggcatttc atccaggaca cctgcctcta cgagtgctcc cccaacttgg    6840
ggccctggat ccagcaggta tgcatggctt cctgcaggta caagacctag cggagcagct    6900
gagctttcca ggcatctctg caggctgcaa ccccagctcc agttctattc ggggctgagt    6960
tgctgggatt cttgaacctg agcccttctt ttgtatcaaa atcacccagg tggatcagag    7020
ctggcgcaaa gagcgggtac tgaacgtgcc cctgtgcaaa gaggactgtg agcaatggtg    7080
ggaagattgt cgcacctcct acacctgcaa gagcaactgg cacaagggct ggaactggac    7140
ttcaggtgag ggctggggtg ggcaggaatg gagggatttg gaagtggagg tgtgtgggtg    7200
tggaacaggt atgtgacaat ttggagttgt agggctggca gacctcaaga tagttccggg    7260
cccagtggct aaaggtcttc cctcctctct acagggttta acaagtgcgc agtgggagct    7320
gcctgccaac ctttccattt ctacttcccc acacccactg ttctgtgcaa tgaaatctgg    7380
actcactcct acaaggtcag caactacagc cgagggagtg gccgctgcat ccagatgtgg    7440
ttcgacccag cccagggcaa ccccaatgag gaggtggcga ggttctatgc tgcagccatg    7500
agtggggctg ggccctgggc agcctggcct ttcctgctta gcctggccct aatgctgctg    7560
tggctgctca gctgacctcc ttttaccttc tgatacctgg aaatccctgc cctgttcagc    7620
cccacagctc ccaactattt ggttcctgct ccatggtcgg gcctctgaca gccactttga    7680
```
ataaaccaga caccgcacat gtgtcttgag aattatttgg        7720

<210> SEQ ID NO 6
<211> LENGTH: 255
<212> TYPE: PRT
<213> ORGANISM: Homo sapiens

<400> SEQUENCE: 6

Met Val Trp Lys Trp Met Pro Leu Leu Leu Leu Val Cys Val Ala
 1               5                  10                  15

Thr Met Cys Ser Ala Gln Asp Arg Thr Asp Leu Leu Asn Val Cys Met
                 20                  25                  30

Asp Ala Lys His His Lys Thr Lys Pro Gly Pro Glu Asp Lys Leu His
             35                  40                  45

Asp Gln Cys Ser Pro Trp Lys Lys Asn Ala Cys Cys Thr Ala Ser Thr
         50                  55                  60

Ser Gln Glu Leu His Lys Asp Thr Ser Arg Leu Tyr Asn Phe Asn Trp
 65                  70                  75                  80

Asp His Cys Gly Lys Met Glu Pro Ala Cys Lys Arg His Phe Ile Gln
                 85                  90                  95

Asp Thr Cys Leu Tyr Glu Cys Ser Pro Asn Leu Gly Pro Trp Ile Gln
            100                 105                 110

Gln Val Asn Gln Thr Trp Arg Lys Glu Arg Phe Leu Asp Val Pro Leu
        115                 120                 125

Cys Lys Glu Asp Cys Gln Arg Trp Trp Glu Asp Cys His Thr Ser His
    130                 135                 140

Thr Cys Lys Ser Asn Trp His Arg Gly Trp Asp Trp Thr Ser Gly Val
145                 150                 155                 160

Asn Lys Cys Pro Ala Gly Ala Leu Cys Arg Thr Phe Glu Ser Tyr Phe
                165                 170                 175

Pro Thr Pro Ala Ala Leu Cys Glu Gly Leu Trp Ser His Ser Tyr Lys
            180                 185                 190

Val Ser Asn Tyr Ser Arg Gly Ser Gly Arg Cys Ile Gln Met Trp Phe
        195                 200                 205

Asp Ser Ala Gln Gly Asn Pro Asn Glu Glu Val Ala Arg Phe Tyr Ala
    210                 215                 220

Ala Ala Met His Val Asn Ala Gly Glu Met Leu His Gly Thr Gly Gly
225                 230                 235                 240

Leu Leu Leu Ser Leu Ala Leu Met Leu Gln Leu Trp Leu Leu Gly
                245                 250                 255

<210> SEQ ID NO 7
<211> LENGTH: 817
<212> TYPE: DNA
<213> ORGANISM: Homo sapiens

<400> SEQUENCE: 7
cgcaggaata gatggacatg gcctggcaga tgatgcagct gctgcttctg gctttggtga        60
ctgctgcggg gagtgcccag cccaggagtg cgcgggccag gacggacctg ctcaatgtct       120
gcatgaacgc caagcaccac aagacacagc ccagccccga ggacgagctg tatggccagt       180
gcagtccctg gaagaagaat gcctgctgca cggccagcac cagccaggag ctgcacaagg       240
acacctcccg cctgtacaac tttaactggg atcactgtgg taagatggaa cccacctgca       300
agcgccactt tatccaggac agctgtctct gagtgctcac ccaacctggg gcctggatc        360 cggcaggtca accagagctg gcgcaaagag cgcattctga acgtgcccct gtgcaaagag       420

| | |
|---|---:|
| gactgtgagc gctggtggga ggactgtcgc acctcctaca cctgcaaaag caactggcac | 480 |
| aaaggctgga attggacctc agggattaat gagtgtccgg ccggggccct ctgcagcacc | 540 |
| tttgagtcct acttccccac tccagccgcc ctttgtgaag gcctctggag ccactccttc | 600 |
| aaggtcagca actatagtcg agggagcggc cgctgcatcc agatgtggtt tgactcagcc | 660 |
| cagggcaacc ccaatgagga ggtggccaag ttctatgctg cggccatgaa tgctggggcc | 720 |
| ccgtctcgtg ggattattga ttcctgatcc aagaagggtc tctgggggtt cttccaacaa | 780 |
| cctattctaa tagacaaatc cacatgaaaa aaaaaaa | 817 |

<210> SEQ ID NO 8
<211> LENGTH: 1669
<212> TYPE: DNA
<213> ORGANISM: Homo sapiens

<400> SEQUENCE: 8

| | |
|---|---:|
| gctaggcagc ttcgaaccag tgcaatgacg atgccagtca acggggccca caaggatgct | 60 |
| gacctgtggt cctcacatga caagatgctg cacaaccccc tcaaagacag tgatgttgag | 120 |
| gtttacaaca tcattaagaa ggagagtaac cggcagaggg ttggattgga gctgattgcc | 180 |
| tcggagaatt tcgccagccg agcagttttg gaggccctag gctcttgctt aaataacaaa | 240 |
| tactctgagg ggtacccggg ccagagatac tatggcggga ctgagtttat tgatgaactg | 300 |
| gagaccctct gtcagaagcg agccctgcag gcctataagc tggacccaca gtgctggggg | 360 |
| gtcaacgtcc agccctactc aggctcccct gcaaactttg ctgtgtacac tgccctggtg | 420 |
| gaacccatg ggcgcatcat gggcctggac cttccggatg ggggccacct gacccatggg | 480 |
| ttcatgacac acaagaagaa aatctctgcc acgtccatct tctttgaatc tatgccctac | 540 |
| aaggtgaacc cagatactgg ctacatcaac tatgaccagc tggaggagaa cgcacgcctc | 600 |
| ttccacccga agctgatcat cgcaggaacc agctgctact cccgaaacct ggaatatgcc | 660 |
| cggctacgga agattgcaga tgagaacggg gcgtatctca tggcggacat ggctcacatc | 720 |
| agcgggctgg tggcggctgg cgtggtgccc tccccatttg aacactgcca tgtggtgacc | 780 |
| accaccactc acaagaccct gcgaggctgc cgagctggca tgatcttcta caggaaagga | 840 |
| gtgaaaagtg tggatcccaa gactggcaaa gagattctgt acaacctgga gtctcttatc | 900 |
| aattctgctg tgttccctgg cctgcaggga ggtccccaca accacgccat gctgggggtt | 960 |
| gctgtggcac tgaagcaagc tatgactctg gaatttaaag tttatcaaca ccaggtggtg | 1020 |
| gccaactgca gggctctgtc tgaggccctg acggagctgg gctacaaaat agtcacaggt | 1080 |
| ggttctgaca accatttgat ccttgtggat ctccgttcca aaggcacaga tggtggaagg | 1140 |
| gctgagaagg tgctagaagc ctgttctatt gcctgcaaca agaacacctg tccaggtgac | 1200 |
| agaagcgctc tgcggcccag tggactgcgg ctggggaccc cagcactgac gtcccgtgga | 1260 |
| cttttggaaa aagacttcca aaaagtagcc cactttattc acagagggat agagctgacc | 1320 |
| ctgcagatcc agagcgacac tggtgtcaga gccaccctga aagagttcaa ggagagactg | 1380 |
| gcaggggata gtaccaggc ggccgtgcag gctctccggg aggaggttga gagcttcgcc | 1440 |
| tctctcttcc ctctgcctgg cctgcctgac ttctaaagga gcgggcccac tctggaccca | 1500 |
| cctggcgcca cagaggaagc tgcctgccgg agaccccac ctgagagatg gatgagctgc | 1560 |
| tccaaaggga actgttgaca ctcgggccct tgaggggt ttcttttgga ctttttcat | 1620 |
| gttttcttca caaatcaaaa tttgtttaag tctcattgtt agtaattct | 1669 |

-continued

<210> SEQ ID NO 9
<211> LENGTH: 3112
<212> TYPE: DNA
<213> ORGANISM: Homo sapiens

<400> SEQUENCE: 9

| | | | | | |
|---|---|---|---|---|---|
| gtggaacctc | gatattggtg | gtgtccatcg | tgggcagcgg | actaataaag | gccatggcgc | 60 |
| cagcagaaat | cctgaacggg | aaggagatct | ccgcgcaaat | aagggcgaga | ctgaaaaatc | 120 |
| aagtcactca | gttgaaggag | caagtacctg | gtttcacacc | acgcctggca | atattacagg | 180 |
| ttggcaacag | agatgattcc | aatctttata | taaatgtgaa | gctgaaggct | gctgaagaga | 240 |
| ttgggatcaa | agccactcac | attaagttac | caagaacaac | cacagaatct | gaggtgatga | 300 |
| agtacattac | atctttgaat | gaagactcta | ctgtacatgg | gttcttagtg | cagctacctt | 360 |
| tagattcaga | gaattccatt | aacactgaag | aagtgatcaa | tgctattgca | cccgagaagg | 420 |
| atgtggatgg | attgactagc | atcaatgctg | ggagacttgc | tagaggtgac | ctcaatgact | 480 |
| gtttcattcc | ttgtacgcct | aagggatgct | tggaactcat | caaagagaca | ggggtgccga | 540 |
| ttgccggaag | gcatgctgtg | gtggttgggc | gcagtaaaat | agttggggcc | ccgatgcatg | 600 |
| acttgcttct | gtggaacaat | gccacagtga | ccacctgcca | ctccaagact | gcccatctgg | 660 |
| atgaggaggt | aaataaaggt | gacatcctgg | tggttgcaac | tggtcagcct | gaaatggtta | 720 |
| aggggagtg | gatcaaacct | gggcaatag | tcatcgactg | tggaatcaat | tatgtcccag | 780 |
| atgataaaaa | accaaatggg | agaaaagttg | tgggtgatgt | ggcatacgac | gaggccaaag | 840 |
| agagggcgag | cttcatcact | cctgttcctg | gcggcgtagg | gcccatgaca | gttgcaatgc | 900 |
| tcatgcagag | cacagtagag | agtgccaagc | gtttcctgga | gaaatttaag | ccaggaaagt | 960 |
| ggatgattca | gtataacaac | cttaacctca | agacacctgt | tccaagtgac | attgatatat | 1020 |
| cacgatcttg | taaaccgaag | cccattggta | agctggctcg | agaaattggt | ctgctgtctg | 1080 |
| aagaggtaga | attatatggt | gaaacaaagg | ccaaagttct | gctgtcagca | ctagaacgcc | 1140 |
| tgaagcaccg | gcctgatggg | aaatacgtgg | tggtgactgg | aataactcca | acaccctgg | 1200 |
| gagaagggaa | aagcacaact | acaatcgggc | tagtgcaagc | ccttggtgcc | catctctacc | 1260 |
| agaatgtctt | tgcgtgtgtg | cgacagcctt | ctcagggccc | cacctttgga | ataaaaggtg | 1320 |
| gcgctgcagg | aggcggctac | tcccaggtca | ttcctatgga | agagtttaat | ctccacctca | 1380 |
| caggtgacat | ccatgccatc | actgcagcta | taaacctcgt | tgctgcggcc | attgatgctc | 1440 |
| ggatatttca | tgaactgacc | cagacagaca | aggctctctt | taatcgtttg | gtgccatcag | 1500 |
| taaatggagt | gagaaggttc | tctgacatcc | aaatccgaag | gttaaagaga | ctaggcattg | 1560 |
| aaaagactga | ccctaccaca | ctgacagatg | aagagataaa | cagatttgca | agattggaca | 1620 |
| ttgatccaga | aaccataact | tggcaaagag | tgttggatac | caatgataga | ttcctgagga | 1680 |
| agatcacgat | tggacaggct | ccaacggaga | agggtcacac | acggacggcc | cagtttgata | 1740 |
| tctctgtggc | cagtgaaatt | atggctgtcc | tggctctcac | cacttctcta | gaagacatga | 1800 |
| gagagagact | gggcaaaatg | gtggtggcat | ccagtaagaa | aggagagccc | gtcagtgccg | 1860 |
| aagatctggg | ggtgagtggt | gcactgacag | tgcttatgaa | ggacgcaatc | aagcccaatc | 1920 |
| tcatgcagac | actggagggc | actccagtgt | tgtccatgc | tggcccgttt | gccaacatcg | 1980 |
| cacatggcaa | ttcctccatc | attgcagacc | ggatcgcact | caagcttgtt | ggcccagaag | 2040 |
| ggtttgtagt | gacggaagca | ggatttggag | cagacattgg | aatggaaaag | ttttttaaca | 2100 |
| tcaaatgccg | gtattccggc | ctctgccccc | acgtggtggt | gcttgttgcc | actgtcaggg | 2160 |

-continued

| | |
|---|---|
| ctctcaagat gcacgggggc ggccccacgg tcactgctgg actgcctctt cccaaggctt | 2220 |
| acatacagga gaacctggag ctggttgaaa aaggcttcag taacttgaag aaacaaattg | 2280 |
| aaaatgccag aatgtttgga attccagtag tagtggccgt gaatgcattc aagacggata | 2340 |
| cagagtctga gctggacctc atcagccgcc tttccagaga acatggggct tttgatgccg | 2400 |
| tgaagtgcac tcactgggca gaaggggca agggtgcctt agccctggct caggccgtcc | 2460 |
| agagagcagc acaagcaccc agcagcttcc agctccttta tgacctcaag ctcccagttg | 2520 |
| aggataaaat caggatcatt gcacagaaga tctatggagc agatgacatt gaattacttc | 2580 |
| ccgaagctca acacaaagct gaagtctaca cgaagcaggg ctttgggaat ctccccatct | 2640 |
| gcatggctaa acacacttg tctttgtctc acaacccaga gcaaaaaggt gtccctacag | 2700 |
| gcttcattct gcccattcgc gacatccgcg ccagcgttgg ggctggtttt ctgtacccct | 2760 |
| tagtaggaac gatgagcaca atgcctggac tccccacccg gccctgtttt tatgatattg | 2820 |
| atttggaccc tgaaacagaa caggtgaatg gattattcta aacagatcac catccatctt | 2880 |
| caagaagcta ctttgaaagt ctggccagtg tctattcagg cccactggga gttaggaagt | 2940 |
| ataagtaagc caagagaagt cagcccctgc ccagaagatc tgaaactaat agtaggagtt | 3000 |
| tccccagaag tcattttcag ccttaattct catcatgtat aaattaacat aaatcatgca | 3060 |
| tgtctgttta ctttagtgac gttccacaga ataaaaggaa acaagtttgc ca | 3112 |

<210> SEQ ID NO 10
<211> LENGTH: 1792
<212> TYPE: DNA
<213> ORGANISM: Homo sapiens

<400> SEQUENCE: 10

| | |
|---|---|
| cgcagcccag actcagactg gggaagcaaa caggggctgg acaggccagg agagcctgtc | 60 |
| ggacagtgat cctgagatgt gggagttgct gcagagggaa aaggacaggc agtgtcgtgg | 120 |
| cctggagctc attgcctcag agaacttctg cagccgagct gcgctggagg ccctggggtc | 180 |
| ctgtctgaac aacaagtact cggagggtta tcctggcaag agatactatg ggggagcaga | 240 |
| ggtggtggat gaaattgagc tgctgtgcca gcgccgggcc ttggaagcct ttgacctgga | 300 |
| tcctgcacag tggggagtca atgtccagcc tactccgggg tccccagcca acctggccgt | 360 |
| ctacacagcc cttctgcaac ctcacgaccg gatcatgggg ctggacctgc ccgatggggg | 420 |
| ccatctcacc cacggctaca tgtctgacgt caagcggata tcagccacgt ccatcttctt | 480 |
| cgagtctatg ccctataagc tcaaccccaa aactggcctc attgactaca accagctggc | 540 |
| actgactgct cgacttttcc ggccacggct catcatagct ggcaccagcg cctatgctcg | 600 |
| cctcattgac tacgcccgca tgagagaggt gtgtgatgaa gtcaaagcac acctgctggc | 660 |
| agacatggcc cacatcagtg gcctggtggc tgccaaggtg attccctcgc ctttcaagca | 720 |
| cgcggacatc gtcaccacca ctactcacaa gactcttcga ggggccaggt cagggctcat | 780 |
| cttctaccgg aaaggggtga aggctgtgga ccccaagact ggccgggaga tcctttacac | 840 |
| atttgaggac cgaatcaact tgccgtgtt cccatccctt caggggggcc cccacaatca | 900 |
| tgccattgct gcagtagctg tggccctaaa gcaggcctgc accccatgt ccgggagta | 960 |
| ctccctgcag gttctgaaga atgctcgggc catggcagat gccctgctag agcgaggcta | 1020 |
| ctcactggta tcaggtggta ctgacaacca cctggtgctg gtggacctgc ggcccaaggg | 1080 |
| cctggatgga gctcgggctg agcgggtgct agagcttgta tccatcactg ccaacaagaa | 1140 |

-continued

| | |
|---|---:|
| cacctgtcct ggagaccgaa gtgccatcac accgggcggc ctgcggcttg gggcccagc | 1200 |
| cttaacttct cgacagttcc gtgaggatga cttccggaga gttgtggact ttatagatga | 1260 |
| aggggtcaac attggcttag aggtgaagag caagactgcc aagctccagg atttcaaatc | 1320 |
| cttcctgctt aaggactcag aaacaagtca gcgtctggcc aacctcaggc aacgggtgga | 1380 |
| gcagtttgcc agggccttcc ccatgcctgg ttttgatgag cattgaaggc acctgggaaa | 1440 |
| tgaggcccac agactcaaag ttactctcct tcccctacc tgggccagtg aaatagaaag | 1500 |
| cctttctatt ttttggtgcg ggagggaaga cctctcactt agggcaagag ccaggtatag | 1560 |
| tctcccttcc cagaatttgt aactgagaag atcttttctt tttccttttt ttggtaacaa | 1620 |
| gacttagaag gagggcccag gcactttctg tttgaaccc tgtcatgatc acagtgtcag | 1680 |
| agacgcgtcc tctttcttgg ggaagttgag gagtgccctt cagagccagt agcaggcagg | 1740 |
| ggtgggtagg caccctcctt cctgttttta tctaataaaa tgctaacctg ca | 1792 |

<210> SEQ ID NO 11
<211> LENGTH: 18596
<212> TYPE: DNA
<213> ORGANISM: Homo sapiens

<400> SEQUENCE: 11

| | |
|---|---:|
| cctgtagtcc cagctacgcg agaggctgag gcagcagaat tacttgaacc caggaggcgg | 60 |
| aggttgcagt gagccgagat cgcgccactg cactccagcc tgggtgagag agcgagactc | 120 |
| tgtctcaaaa aaaaaaaaaa aagaccgcca gggctcaaac aaaaaaccctc ggaaaagccc | 180 |
| tggcggtctt tttttttttt tttttttttt tttttggga cagtcttgct ctgtcgccca | 240 |
| ggctggagta caatggtcgg atcttggctc actgcaacct ctgcctccca ggttcaagca | 300 |
| attcttctgc ctcagcctcc caagtagcca ccacgcccag ctaatttttg tacttttagt | 360 |
| agagacgggg gtttcaccat gttgtccagg ctggtcttga actcctgacc tcaggtgatc | 420 |
| cacccgcctc ggccccccaa agtactagga ttacaggcgt gagccaccgc gtccagcgcc | 480 |
| ctggcggttt ttaatcaagt agaaaagctg cattatacca cttgcttcgg ttgcttcagt | 540 |
| gagaacgaag aaatggaaat gcaaatccct tattagttgt aggaaacaga tctcaaacag | 600 |
| cagttttgtt gacaagaccg caggaaaacg tgggaactgt gctgctggct tagagaaggc | 660 |
| gcggtcgacc agacggttcc caaagggcgc agtccttccc agccaccgca cctgcatcca | 720 |
| ggttcccggg tttcctaaga ctctcagctg tggccctggg ctccgttctg tgccacaccc | 780 |
| gtggctcctg cgtttccccc tggcgcacgc tctctagagc gggggccgcc cgacccccgc | 840 |
| cgagcaggaa gaggcggagc gcgggacggc cgcgggaaaa ggcgcgcgga agggtcctg | 900 |
| ccaccgcgcc acttggcctg cctccgtccc gccgcgccac ttggcctgcc tccgtcccgc | 960 |
| cgcgccactt cgcctgcctc cgtccccgc ccgccgcgcc atgcctgtgg ccggctcgga | 1020 |
| gctgccgcgc cggcccttgc ccccgccgc acaggagcgg gacgccgagc cgcgtccgcc | 1080 |
| gcacggggag ctgcagtacc tggggcagat ccaacacatc ctccgctgcg gcgtcaggaa | 1140 |
| ggacgaccgc acgggcaccg gcaccctgtc ggtattcggc atgcaggcgc gctacagcct | 1200 |
| gagaggtgac gccgcgggcc cctgcgggac gggtggcggg aaggagggag gcgcggctgg | 1260 |
| ggagagcgct cgggagctgc cgggcgctgc ggaccccgtt tagtcctaac ctcaatcctg | 1320 |
| ccagggaggg gacgcatcgt cctcctcgcc ttacagacgc gaaacggag ggtcccatta | 1380 |
| gggacgtgac tggcgcgggc aacacacaca gcagcgacag ccgggaggta agccgcgtcc | 1440 |
| cagcggctcc gcggccgggc tcgcagtcgc cccagtgatg ccgtggcccc cgaggcgggc | 1500 |

-continued

```
gtcatcgggc agcgtttgcc cagtgctgga gggttaggga gagctgcctg ggcttgaccg    1560
cgcgccggtc tcaaagtcct ggctttggcc cctcctccgt tttcccctgt ggaccattcc    1620
gcttcgcagc gttttcaaaa actggagcga aagtgatgtg ggcggggcaa aggcggcggg    1680
aagaggacag cactgaagct ggcgcgggaa cttggtttcc tggtggcctc ccatccaatc    1740
cccacgaacc agctttcctc ttaaaccttg aaaagagaaa ttcgggagtt cgagttctta    1800
gtcgtccttt cctctttcct ttccgacagg agcaccccag gcaaaaaatg tctcgcgggt    1860
cattggcgcc aggctttcag gggacagtgg ggcggggcgg ggtgggcaca ggacgttagg    1920
cagccgttgg ccctccctaa ggccacaccg tcctgccgtc ctggatcctg cgccagctgc    1980 gcggggagg ggactcgaag gtgtgtgagc caggggctga ccttgaccgc tcagataaat     2040
ggagcgcagc cttgacacag gggtggaggt ggttttgaat ggggaaaccc attcgtggtg    2100
aagcagattc actgtagcta gcggaaaagc cctccggccc acggacccat ctagagacga    2160
atacatagca gctgctgtgg ctgattggcg tgggacagcg tggggagttt tgtctgagga    2220
gagggatcca cttttctgca gctccaagcc caggggcctt tgatgagcca tagacctcat    2280
ttttaaccca cctttctgct tagacattga gcaagttact tctcatatag cttccctata    2340
tgttaaaaat ggagaaaata atgcttagta ggcaattctg ataaaagcag gtgcttgcaa    2400
aaatctctct gttgtctgaa tataaactgt accacaagcg agtgcggatg aacgaggact    2460
gcatttaaag ataagttttt acactttcat ttctctgtgg ctcgacactt ctgatgcctc    2520 ccttttttgtt cctgggacac atgcttggtg ttgtcttcac acctttgtga caggattagc    2580
actagtgggc agtggatgat agctcctcct cccttttgcc acatgttcat ccctgccctc    2640
gccaccatct cactgtgtgg aattcctgtg tccactggtc accggggcac agaagtgctg    2700
tctcagcctg aatcgggcca ctgatgggac ttgcagcctg ggagctccac cgtgatctct    2760
ggcccacttt gcgggagtct aggctttctg gatgctccag gcctcacgtc ccagggcagt    2820
tttcttccct gaagaaagtt ggatggcatg atctgtcttc ccatcttgaa accgtatggc    2880
aaattgtttt tcagatgaat tccctctgct gacaaccaaa cgtgtgttct ggaagggtgt    2940
tttggaggag ttgctgtggt ttatcaaggt aaagaagtcg ctgctattag aagtcagtag    3000
tctgttctca acacagcagc cagtgagatc ctttcaaaac tcaaagcagc caggtgtggt    3060
ggctcacgcc tgtaatccca ccgctttggg aggctgagtc agatcacctg aggttaggaa    3120
tttgggacca gcctggccaa catggcgaca ccccagtctc tactaataac acaaaaaatt    3180
agccaggtgt gctggtgcat gtctgtaatc ccagctactc aggaggctga ggcatgagaa    3240
ttgctcacga ggcggaggtt gtagtgagct gagatcgtgg cactgtactc cagcctggcg    3300
acagagggag aacccatgtc aaaaacaaaa aaagacacca ccaaaggtca aagcatatca    3360
ttcctcaccc tcaagccctt agtggctcca tttcactcag taagagccac ggtccttatg    3420
gtgtccgttt ttcagctctg accttagctg ctgctctctg caccaccctg ctgttcttgt    3480 gagttttttga gcacaccggg acatccccac tccctggaac cttcttcccc cacacttggc    3540
ttcttccttt gagtctctac tccactcggg caagccttcc tagacctcct gatttaaaac    3600
tgtgactctc ccccaacctc cttggtgttt ctccgtagac gaacatcacc atctgatgta    3660
tgtcagcctt tcccttcccc tgttagaagg gggacagcag gtagtaaaag tgaaatgtgc    3720
tgtaagcttt atgagggcag aggatttgtt tctcgtgttc actgttgtat cgccagggcc    3780
tcaaacacag cctgccacat agtaggagtc aacatatatt gatcactaaa tgtagatacc    3840
```

```
acctgtgttc ccatgttcat ataaattcta gaagagtctc ttcagtaaca aggtgaaccc    3900
cttccagagg gctgagtagg tacctcaggc cggggccaga gtgctgtgaa gacagcagca    3960
gcccagacca agcttctctg tgttccgtgt cctggtctag aaccagcgat gttctttctg    4020
accagtgctt tttggaaggt ggctgaggtc tgggctcagg tctgggccat actagaagct    4080
gggatccctt ctatagagca cttggtatgg cttgtatggt cttggggcaa gccagaccca    4140
agccctctta tcccatttta gaaagggctt caatttggat ccagcccag gtctgcctta     4200 gctctgtatt cttggggtat tttgttctgt attggcctat cttgactaac aatgagcctt    4260
ggatttgaaa catatcatca gaaacctcag aagacaacat tcttaaactg ctagagcct     4320 ggtctgaatg gatgaaaagg agagactttt gaagcaatat gtaaaagatt gagaaatgat    4380
ttgttggaaa tttctcaatt ggagaaattt ctttgatttg ttggaaattt ctttgattct    4440
ttctcaatca agaaaatcg ggacaaactc aacaatagaa agggaggaag caagatactc     4500
agaaataaaa tgcattcccc tgtttcaact taatgcttca attcaggatt ctaaggaatc    4560
cttgccagga atgtcagact caccttgata gttggagtta ctccattggt gactcgatca    4620
aatacaggag ttgaggcacc tgcactgtaa aatactgatt agtctgatca ttaggaatat    4680
cctgtatgcc aggtagaaga tacattgaac agattgcatg taggcattaa attcattttg    4740
gggtattaca tatagacaac acatttcatt aagaaacata aaactgtcag atcggtggaa    4800
tacttaaaag cacttggagg tgtttagcct aaaaagctta gttgagggga atggaagaaa    4860
agatctggga gggtggttcc aaagaaggga tcagactatc ctaaagccct caggaatctg    4920
ggctgggacc acctacttaa agataggatg gcagctggg tgtggtggct cacgcctgta     4980
atcccagcac ttcgggaggc cgaagcgggc ggatcacctg aggtcaggag ttcgaggcca    5040
gcctgaccaa catgagaaa cgctgtctct actaaaaata caaaattagc tgggtgtagt     5100
ggcgcatgcc tgtaatccca gctactcggg aggctgaggc aggggaatcg cttgaacctg    5160
ggaggtggag ggtgccgtga gccacgatcg cgccattgca ctccagcctg gcaacaaga    5220 gcgaaactct caaaaaacaa aaaaaaggat gggttccata tgggtggtgt caagtgccca    5280
cctcctagca agtcagcagg ggccagaggc ccttgtaagt ggtgtctcgg ggggatcaac    5340
tgagatggct taagatttac ctggatgcct gctctgctct ccccatctct tccaggatc     5400 cacaaatgct aaagagctgt cttccaaggg agtgaaaatc tgggatgcca atggatcccg    5460 agacttttg gacagcctgg gattctccac cagagaagaa ggggacttgg gcccagttta    5520
tggcttccag tggaggcatt ttggggcaga atacagagat atggaatcag gtgaggagat    5580
agaacaatgc cttccatttc cgggtgccct tcctagcacg tgtttgctcc gttgttttag    5640
ataaggtctg ggggatgagt caatgtcaca ggagctgatg tatagctttg accttgtgag    5700
gggtggtgcc aggttgaagc cacaattaac gcctactgaa ggccgtttca catcttttt     5760 tttttttttt ttttaattat tatactttaa gttttagggt acatgtgcac aatgtgcagg    5820
ttagttacat atgtatacat gtgccatgct ggtgcgctgc accactaact caccatctag    5880
catcaggtat atctcccaat gctatccctc cccctcctc ccaccccaca acatcccag      5940 agtgtgatgt tccccttcct gtgtccatat gttctcgttg ttcgattccc actatgagtg    6000
agaatatgcg gtgtttggtt ttttgttctt gcgatagttt actgagaatg atgatttcca    6060
tttcaccacg tccctacaga ggacatgaac tcatcatttt ttatggctgc atagtattcc    6120
atggtgtata tgtgccacat tttcttaatc cagtctatca tgttggacat ttgggttggt    6180
tccaagtctt tgcctattgt gaatagtgcc acaataaaca tacgtgtgca tgtgtcttta    6240
```

```
tagcagcatg atttaatagt cctttgggta tatacccagt aatgggatgg ctgggtcaaa    6300
tggtatttct agttctagat ccccgaggaa tcgccacact gacttccaca atggttgaac    6360
tagtttacag tcccaccaac agtgtcaaag tgtcctattt ctccacatcc tctccagcac    6420
ctgttgtttc ctgactttt aatgattgcc attctaactg gtgtgagatg gtatctcatt    6480
gtggttttga tttgcgtttc tctgatggcc agtgatggtg agcattttt catgtgtttt    6540 ttggctgcat aaatgtcttc ttttgagaag tgtctgttca tgtccttcgc ccacttttg    6600 atggggttgt ttttttctta taaatttgtt tgagttcatt gtagattctg gatattagcc    6660
ctttgtcaga tgagtaggtt gcaaaaatgt tctcccattt tgtgggttgc ctgttcactc    6720
tgatggtagt ttcttttgct gtgcagaagc tctttagttt aattagatcc catttgtcaa    6780
ttttggcttt tgttgccatt gcttttggca taggcatgaa gtccttgccc atgcctatgt    6840
cctgaatggt aatgcctagg ttttcttcta gggtttttat ggttttaggt ctaacgttta    6900
agtctttaat ccatcttgaa ttgattttg tataaggtgt aaggaaggga tccagtttca    6960 gcttttaca tatggctagc cagttttccc agcaccattt attacatagg gaatcctttc    7020
cccattgctt gtttttctca ggtttgtcaa agatcagata gttgtagata tgcggcgtta    7080
tttctgaggg ctctgttctg ttccattgat ctatgtgtct gttttggtac cagtaccata    7140
ctgttttggt tactgtagcc ttgtagtata gtttgaagtc aggtagcgtg atgcctccag    7200
ctttgttctt ttggcttagg attgacttgg cgatgcgggc tctttttgg ttccatatga    7260 actttaaagt agttttttcc aattctgtga agaaagtcat tggtagcttg atggggatgg    7320
cattgaatct ataaattacc ttgggcagta tggccatttt cacgatattg attcttccta    7380
cccatgagca tggaatggtc ttccatttct ttgtatcctc tttatttca ttgagcagtg    7440 gtttgtagtt ctccttgaag aggtccttca catcccttt aaggtggatt cctaggtatt    7500
ttattctctt tgaagcaatt gtgagtggaa gttcactcat gatttggctc tctgtttgtc    7560
tgttattggt gtataagaat gcttgtgatt tttgcagatt gattttatat cctgagactt    7620
tgctgaagct gcttatcagc ttaaggagat tttgggctga gacaatgggg ttttctagat    7680
atacaatcat gtcgtctgca aacagggaca atttgacttc ctcttttcct aattgaatac    7740
cctttatttc cttctcctgc ctaattgccc tggccagaac ttccaacact atgttgaata    7800
ggagtggtga gagagggcat ccctgtcttg tgccagtttt caaagggaat gcttccagtt    7860
tttgcccatt cactatgata ttggctgtgg ctttgtcata gatagctctt attattttga    7920
aatatgttcc atcaatacct aatttattga gagtttttag catgatgtgt tgttgaattt    7980
tgtcaaaggc ttttttctgca tctattgaga taatcatgtg gttttgtct ttggatctgt    8040 ttatatgctg gattacattt attgatttgc gtatattgaa ccagccttgc atcctaggga    8100
tgaagcccac atgatcatgg tggataagct ttttgatgtg ctgctggatt cggtttgcca    8160 gtatttatt gaggatttt gcatcaatgt tcatcaagga tattggtcta aaattctctt    8220
ttttggtgtg tctctgccca gctttggtat caggatgatg ttggcttcat aaaatgagtt    8280
agggaggatt ccctcttttt ctattgattg gaatagtttc agaaggaatg gtaccagttc    8340
ctctttgtac ctctggagaa ttcggctgtg aatccatctg gtcctggact ctctttggtt    8400
ggtaagctat tgattattgc cacaatttca gctcctgtta ttggtctatt cagagattca    8460
acttcttcct ggtttagtct tgggagagtg tatgtgtcaa ggaatttatc catttcttct    8520
agattttcta gtttatttgc gtagaggtgt ttgtagtaat ctctgatggt agtttgtatt    8580
```

```
tctgtgggat cggtggtgat atccccttta tcatttttta ttgcgtctat ttgattcttc   8640
tcttttcctt tattagtctt gctagcggtc tataaatttt gttgatcctt tcaaaaaacc   8700
agctcctgga ttcattaatt ttttgaaggg ttttttgtgt ctctatttcc ttcagttctg   8760
ctctgatttt agttatttct tgccttctgc tagcttttga atatgtttgc tcttgctttt   8820
ctagttcttt taattgtgat gttagggtgt caattttgga tctttcctgc tttctcttgt   8880
gggcatttag tgctataaat ttccctctac acactgcttt gaatgtgtcc cagaggttct   8940
ggtatgttgt gtctttgttc ttgttggttt caaagaacat ctttatttct gccttcattt   9000
cgttatgtac ccagtagtca ttcaggagca ggttgttcag tttccatgta gttgagcagt   9060
tttgagtgag attcttaatc ctgagttcta gtttgattgc actgtggtct gagagatagt   9120
ttgttataat ttctgttctt ttacatttgc tgaggagagc tttacttcca actatgtggt   9180
cggttttgga ataggtgtgg tgtggtgctg aaaaaaatgt atattctgtt gatttgggat   9240
ggagttctgt agatgtctat taggtctgct tggtgcagag ctgagttcaa ttcctgggta   9300
tccttgttga ctttctgtct cgttgatctg tgtactgttg acagtgggtg ttaaagtctc   9360
ccattattaa tgtgtggagt ctaagtctct ttgtaggtca ctcagatgat ggcacttac    9420 tgggcgcttg gcactttcca tactgtgtca tcggcagata gctgcatggt tggtgttcgt   9480
gctggggaat gggaagttca tcggtgggac aaggacaaaa tgcccccatt gctttgttgt   9540
ggctttaatc tccctttcga ggctgagcca cagcgtgctg taggtggcgc tgctgtgaag   9600
cgcagtacca gggtcacact ccactcccag ctctgcagag gtggagaaag aatgaaacat   9660
ctcactcctg gacttccact ttcctgtcac tgttggtgtc acctcttact ggatgtcaca   9720
gagcccagcc cctcccacct gtgcctagga aaagcagatg ccaccttgga atgtggggtt   9780
tgtgtgtgca atttactagc tgggcagaga ccagcaacct ggagagcagg tgtctcgtct   9840
aaggggacag tcacatttca cctccagcca cctggaggaa tttgggcctg gtgatgtcag   9900
aattcttcaa taaaagccta aaatctatat tttatgtgcg gtcatgagat ctgttaaatg   9960
ttagcaactt caggaagttt aaaaatgctg tgtggaccta aataggcaa gttcttaaag   10020 gcagaaagtg gaatgctagt ttccagggac tggggaacag ggaggaatgg ggagttcatg   10080
tttaatgggc acagaggttt tgttagggat gacgaaaaag ttcggagat ggtgatggtg    10140 atggagatgg tgatggtgat ggagatggtg atggtgatgg tgatggtgat gggtgatggt   10200
gatggtgatg gtgatggtga tggagatggt gatggtgatg gtgatggaga tggtgatggt   10260
gatggtgatg gtgatggaga tggtgatggt gatggagatg gtgatggtga tggtgatgga   10320
gatggtgatg gtgatggtga tggtgatggt gatggtgatg gtgatggaga tggagatggt   10380
gatggtgatg gttgcctaac atcaggaacg tgcttaatgc ttctgaattg cacacaaaaa   10440
tggcaagttt aatattatgt gtactttatc acaatgaaaa aagctgctgc gtgggccaag   10500
ttacttgtgc aggtaatgtt ctgcaggtgg ttgcctgcac ctcagttgta gggtgtccgt   10560
aggatgtgag gccagtcccc gggcttaatg atgctttaaa tcctgcctag tattcaatta   10620
tttcttgtcg cttaaaaggc ctaataaaat tatggtctta gttacagtg gtatgaatgc    10680 ttagctgttg gattttagta ggaaagttcg tccctttttg ttttaatt tgttttacag     10740 attcacagga atttttttt tttttttttt tttttttttt taatgcacag aaagtttccc    10800
tggactctct acccagtttc cccagtgata atatcttggg taacatcctg tatacattca   10860
cattggtgca ttcctcagag ttgtcagatt ttgctagttt tacgtgcact tgtgtatgtg   10920
tgtatttgca attttagcac gtgtagactc ttgtaaccac tacaatcaag ttacagaact   10980
```

```
acactaccaa ggttcatctt tttaaaatct ttgatgttac cttttttgga acagtgacca    11040
tgagaggact ttcctcccaa aattttgaaa actactgaac cagaatatag tctgacacta    11100
ataggtagaa atttaaccaa aggagattat gaagctctgc acttgagtta acaaaatcac    11160
ttctcagctt ccagttccat ctcagaagga aggaaaaggg attaaaaatc cagagaccag    11220
aaaatgggag caaagtacaa ggtggtgtaa tcattacaga ggtttcctga tgtttccaag    11280
tcagtcgtgt gttgagctgc taaactctaa agtaatttta ggtggaatgt tggaaacatg    11340
ctgctgaggt gatagaaagg aatccatggt cctctgttag ttggaaagta tatggaatac    11400
tatattctac ataagataca atactctctg tgagacaagg ataaagtaga ttttgtcagt    11460
gaaattgtga caagaatcgc tgatgggttt agagcctaag tttgcgagga gcactggaag    11520
aaattaagat tgttgagatt ggaaagggtt agctatgggg aacaggagg aggtgactcc     11580
atgcagacc aaatattcaa aggactgtgt agaagaggaa aaagactttg ttagggctcc     11640
agaggacaga gccaggagtc agacagggcc ttgaactcaa cccaccgaga tctgcaaact    11700
ttgcaggatg caccagatgt cttgtagcca tgggtcaagg ggggaccctg ggtaagagac    11760
tgtaatagat gacctctaag gccatctcat gacatgtgtg attaatgtat gtacctgtcc    11820
tctcttttg acaattctac agattattca ggacagggag ttgaccaact gcaaagagtg     11880
attgacacca tcaaaaccaa ccctgacgac agaagaatca tcatgtgcgc ttggaatcca    11940
agaggttgaa agaaccccgt cgtcttcatt tatactaacc atactcttag agggaagcaa    12000
tctggttttg tgcagaggca ctgagggagg caggaccctg ggcaacttcc cccagccaca    12060
tggttgtgtg acgttgggca agtcacattt tgctgcactt tcaccttcag atcatgaggt    12120
tgggcccaga ggatttttt ttttttttt tttttgaga cagagttttg ctctgttgcc       12180
caggctggaa tgcaacggcg tgatcttggc tcactgtaac ctctgcctcc tgggttcgag    12240
tgattctcct gcctcagcct ccaagtagct gggattacag catgtgccac catgcctggc    12300
taattttgta tttttagtag agacgggttc acatgttggt caggctggtc ttgactcctg    12360
accctcagat gatctgcctt gcctcagcct cccaaccgag tgatcttaag ttgtgtatta    12420
tactcattct tacacaaaaa gggctttaaa tgcctagaaa ctacatgaag atgttaacat    12480
tttaaatgga agcagatgaa gttccagctc gctgccacct cactaacatt tttaacaatt    12540
atattgtaaa attcaactct accagggtgt agagccaggt gtggtggctc acacctgtaa    12600
ttccaacaac tccagaggcc aaggcgagag gatcatttga acccacggaa tttgaggctg    12660
tagtgagtca tgatcacgcc attgcactcc atcctgggca acagagtgag accctgaata    12720
tttaaaaaca acaacaacaa caaaactcta tcaggatatc ataagtactt agagtgaaat    12780
acttgcatct gtaatagaga cttatttttt tttttttga gacacagtct caccctgttg    12840
cccaggctgg agtgcagtgg tttgatctcc gctcacggca acctccatct cccaggttca    12900
agtgagttcc cattcctcag ccccagagct gggaccacag gcgcgcgaat ttttgtattt    12960
ttagcagaga cggggtttca ctatgttggc caggctagtc tcaaactcaa gttggcctca    13020
agtgatctgc ccaccctggc gtcccagtgt tgggatttca ggcatgagcc actgtgcctg    13080
gccatgtaat agagactttt aatataggag ggtgtaccag aagcaccagt ttcctgtggc    13140
aaacagaatt attcctgctg tatttgtaat ttggtgccac gaggtagccc agatcccttc    13200
agctctgatg gaagagcatt gcttcagccg taaatggaca cctgcagaaa ccttgcaccg    13260
atggatagtc tccctcagct ccgtgccatc gctgcagggg ctgttatgga catcactgca    13320
```

-continued

```
gcccagtggc tctctctcct ggtctccacc atatgagttg gcttctgttt ctctcctgtt    13380
ttactttgcc tttagctgtg gtctttcaaa ccaccatccc tccttatctt cctctgctgg    13440
ttcctcagat cttcctctga tggcgctgcc tccatgccat gccctctgcc agttctatgt    13500
ggtgaacagt gagctgtcct gccagctgta ccagagatcg ggagacatgg gcctcggtgt    13560
gcctttcaac atcgccagct acgccctgct cacgtacatg attgcgcaca tcacgggcct    13620
gaaggtgggc tgtctcggga agggtgactt gccagcctac cacatgagct cttcagttct    13680
ttaatatggg aaaacaaatt gcagagttta gtctctgatt agcttttaaa tttgatatgt    13740
gtaagtaaga catgaaccag cttttacttt gaaaccttcc ttttctggaa ggttttctgg    13800
ccctgtggta tatgcactaa cagatctata caggttgttt gtgatacagc ttctatggat    13860
cttctcaaaa gctatgctga ggttgggtat ggtggctcat gcctgtaatc ccagcacttt    13920
ggaagactga gacaggagca attgcttgag gtctggagtt caataccagc ctgggcaaca    13980
taacaagatg ctgttgctac aaaaaaatgg aaaagctaca ctaaattatt tttttaaaaa    14040
aagccttgcg gtgtctgcat attctaatgt ttttaaatga tgttttaaag aattgaaact    14100
aacatactgt tctgctttct cccggtttat agccaggtga ctttatacac actttgggag    14160
atgcacatat ttacctgaat cacatcgagc cactgaaaat tcaggtaaga attagatgtt    14220
atacttttgg gtttggtacc ttctcttgat aaaaggttga ctgtggaaca ggtatctgct    14280
caatgctgtg tccaagataa agatgactgc tccaaatgtg gggcttcagt ttagggagaa    14340
gtggtgggca ggtgggcagg acaaggcagg catctgcctc agcaaccatg gcacttaact    14400
tgtcaggtgc tgtgaggtac taagcaccag taccagagag ggaagagcca cattcaagcc    14460
aggggattgt ccaaaaggag gcattttaac tcattttaac ttgaaggaga attgaagtgc    14520
aaatgttttt ccttttcttt tttttgaga tggagtcttt ctctgtcggc caggctggag    14580
tgtgccgtgg tgcgatctca gctcactgca acctccacct cccgggttca agcaattctt    14640
ctgcctcagc ctcccaggta gctgggatta caggcacatg ccaccacacc cagctaattt    14700
tttgtattat tagtagagat ggggtttcgt catgttggcc aggctgatct caaactcctg    14760
acttcaagtg taccacctgc ctcagcctcc gaaagttctg gaattacagg cataagccac    14820
caccctggcc ataaatattt tttgttaatt ttacattaag tacaatattt aggtccaaac    14880
ttcaaaagtc tgttgaaatc cctgaagtta tagcagccaa caattgatat gaaatggcaa    14940
taaaaatgta agttcatctg cttcatgagc cttaaggaaa aaaactcaga accagacact    15000
ttttagcccc ttccaggtta gatccaggtt ttaaaagtta ttcctttgag ggagtttggc    15060
tgcttttgag tggaggtgac ttcaggctta ttctctctgg ctctctgctc tggtcatttt    15120
tagacatagt aataggttgt gacctgtctt cacatcctaa ttgccactgt ctgttcatcc    15180
caggaatcct ggctttcatc cctttctgtt cactgtccat gcatgtcatc tttccttctt    15240
tctgccaggg accagatggg ttagggattg tgaattcaag taaacgtaga gctactatga    15300
gttacagatt gactgtgttc ctgtctttaa taaatttgcc aagagtggtt ataagaactt    15360
acacctgatg aggcaccagg ctcctgatgc tgtgtaatgt cacaaaatac ccctcactct    15420
cgatctgtgc aagagaacag ctggttgcgc tccaatcatg ttacataacc tacgcgaagg    15480
tatcgacagt atcatactcc tgtaaaatag aactttgttg atcacatcct gtgtacttgt    15540
ttcacggaca tgaggagcaa ttacaacagg tcgtacaatt atggcaaaat aatggcctta    15600
ttttgttttt agcttcagcg agaacccaga ccttttcccaa agctcaggat tcttcgaaaa    15660
gttgagaaaa ttgatgactt caaagctgaa gactttcaga ttgaagggta caatccgcat    15720
```

```
ccaactatta aaatggaaat ggctgtttag ggtgctttca aaggagctcg aaggatattg    15780 tcagtctttta ggggttgggc tggatgccga ggtaaaagtt cttttttgctc taaaagaaaa   15840 aggaactagg tcaaaaatct gtccgtgacc tatcagttat taattttttaa ggatgttgcc   15900 actggcaaat gtaactgtgc cagttctttc cataataaaa ggctttgagt taactcactg   15960
agggtatctg acaatgctga ggttatgaac aaagtgagga gaatgaaatg tatgtgctct   16020
tagcaaaaac atgtatgtgc atttcaatcc cacgtactta taaagaaggt tggtgaattt   16080
cacaagctat ttttggaata tttttagaat attttaagaa tttcacaagc tattccctca   16140
aatctgaggg agctgagtaa caccatcgat catgatgtag agtgtggtta tgaactttaa   16200
agttatagtt gttttatatg ttgctataat aaagaagtgt tctgcattcg tccacgcttt   16260
gttcattctg tactgccact tatctgctca gttccttcct aaaatagatt aaagaactct   16320
ccttaagtaa acatgtgctg tattctggtt tggatgctac ttaaaagagt atattttaga   16380
aataatagtg aatatatttt gccctatttt tctcatttta actgcatctt atcctcaaaa   16440
tataatgacc atttaggata gagttttttt ttttttttt taaacttttta taaccttaaa   16500 gggttatttt aaaataatct atggactacc attttgccct cattagcttc agcatggtgt   16560
gacttctcta ataatatgct tagattaagc aaggaaaaga tgcaaaacca cttcggggtt   16620
aatcagtgaa atatttttcc cttcgttgca taccagatac ccccggtgtt gcacgactat   16680 tttattctg ctaatttatg acaagtgtta aacagaacaa ggaattattc caacaagtta   16740
tgcaacatgt tgcttatttt caaattacag tttaatgtct aggtgccagc ccttgatata   16800 gctattttg taagaacatc ctcctggact ttgggttagt taaatctaaa cttatttaag   16860
gattaagtag gataacgtgc attgatttgc taaaagaatc aagtaataat tacttagctg   16920
attcctgagg gtggtatgac ttctagctga actcatcttg atcggtagga ttttttaaat   16980
ccatttttgt aaaactattt ccaagaaatt ttaagccctt tcacttcaga aagaaaaaag   17040
ttgttggggc tgagcactta attttcttga gcaggaagga gtttcttcca aacttcacca   17100
tctggagact ggtgtttctt tacagattcc tccttcattt ctgttgagta gccgggatcc   17160
tatcaaagac caaaaaaatg agtcctgtta acaaccacct ggaacaaaaa cagatttttat  17220 gcatttatgc tgctccaaga aatgctttta cgtctaagcc agaggcaatt aattaatttt   17280
tttttttttg acatggagtc actgtccgtt gcccaggctg cagtgcagtg gcgcaatctt   17340
ggctcactgc aacctccacc tcccaggttc aagtgattct cctgcctcag cctcccatgt   17400
agctgggatc acaggcacct gccaccatgc ccggctaatt ttttgtattt tttgtagaga   17460
cagggtttca ccatgttggc caggctggtc tcaaacacct gacctcaaat gatccacctg   17520
cctcagcctc ccaaagtgtt gggattacag gcgtaagcca ccatgcccag ccctgaatta   17580
atatttttaa aataagtttg gagactgttg gaaataatag ggcagaggaa catattttac   17640
tggctacttg ccagagttag ttaactcatc aaactctttg ataatagttt gacctctgtt   17700
ggtgaaaatg agccatgatc tcttgaacat gatcagaata aatgcccag ccacacaatt    17760 gtagtccaaa cttttttaggt cactaacttg ctagatggtg ccaggttttt ttgcacaagg   17820
agtgcaaatg ttaagatctc cactagtgag gaaaggctag tattacagaa gccttgtcag   17880
aggcaattga acctccaagc cctggccctc aggcctgagg attttgatac agacaaactg   17940
aagaaccgtt tgttagtgga tattgcaaac aaacaggagt caaagcttgg tgctccacag   18000
tctagttcac gagacaggcg tggcagtggc tggcagcatc tcttctcaca ggggccctca   18060
```

| | | | | |
|---|---|---|---|---|
| ggcacagctt | accttgggag | gcatgtagga | agcccgctgg | atcatcacgg gatacttgaa | 18120 |
| atgctcatgc | aggtggtcaa | catactcaca | caccctagga | ggagggaatc agatcgggc | 18180 |
| aatgatgcct | gaagtcagat | tattcacgtg | gtgctaactt | aaagcagaag gagcgagtac | 18240 |
| cactcaattg | acagtgttgg | ccaaggctta | gctgtgttac | catgcgtttc taggcaagtc | 18300 |
| cctaaacctc | tgtgcctcag | gtccttttct | tctaaaatat | agcaatgtga ggtgggact | 18360 |
| ttgatgacat | gaacacacga | agtccctctg | agaggttttg | tggtgccctt taaaagggat | 18420 |
| caattcagac | tctgtaaata | tccagaatta | tttgggttcc | tctggtcaaa agtcagatga | 18480 |
| atagattaaa | atcaccacat | tttgtgatct | atttttcaag | aagcgtttgt atttttcat | 18540 |
| atggctgcag | cagctgccag | gggcttgggg | tttttttggc | aggtagggtt gggagg | 18596 |

<210> SEQ ID NO 12
<211> LENGTH: 3291
<212> TYPE: DNA
<213> ORGANISM: Homo sapiens

<400> SEQUENCE: 12

| | | | | |
|---|---|---|---|---|
| accgggcaag | cgggaaccag | gtggccaccc | ggtgtcggtt | tcattttcct ttggaatttc | 60 |
| tgctttacag | acagaacaat | ggcagcccga | gtacttataa | ttggcagtgg aggaagggaa | 120 |
| catacgctgg | cctggaaact | tgcacagtct | catcatgtca | aacaagtgtt ggttgcccca | 180 |
| ggaaacgcag | gcactgcctg | ctctgaaaag | atttcaaata | ccgccatctc aatcagtgac | 240 |
| cacactgccc | ttgctcaatt | ctgcaaagag | aagaaaattg | aatttgtagt tgttggacca | 300 |
| gaagcacctc | tggctgctgg | gattgttggg | aacctgaggt | ctgcaggagt gcaatgcttt | 360 |
| ggcccaacag | cagaagcggc | tcagttagag | tccagcaaaa | ggtttgccaa agagtttatg | 420 |
| gacagacatg | gaatcccaac | cgcacaatgg | aaggctttca | ccaaacctga agaagcctgc | 480 |
| agcttcattt | tgagtgcaga | cttccctgct | ttggttgtga | aggccagtgg tcttgcagct | 540 |
| ggaaaagggg | tgattgttgc | aaagagcaaa | gaagaggcct | gcaaagctgt acaagagatc | 600 |
| atgcaggaga | aagcctttgg | ggcagctgga | gaaacaattg | tcattgaaga acttcttgac | 660 |
| ggagaagagg | tgtcgtgtct | gtgtttcact | gatggcaaga | ctgtggcccc catgccccca | 720 |
| gcacaggacc | ataagcgatt | actggaggga | gatggtggcc | ctaacacagg gggaatggga | 780 |
| gcctattgtc | cagcccctca | ggtttctaat | gatctattac | taaaaattaa agatactgtt | 840 |
| cttcagagga | cagtggatgg | catgcagcaa | gagggtactc | catatacagg tattctctat | 900 |
| gctggaataa | tgctgaccaa | gaatggccca | aaagttctag | agtttaattg ccgtttggt | 960 |
| gatccagagt | gccaagtaat | cctcccactt | cttaaaagtg | atctttatga agtgattcag | 1020 |
| tccaccttag | atggactgct | ctgcacatct | ctgcctgttt | ggctagaaaa ccacaccgcc | 1080 |
| ctaactgttg | tcatggcaag | taaaggttat | cctggagact | acaccaaggg tgtagagata | 1140 |
| acagggtttc | ctgaggctca | agctctagga | ctggaggtgt | tccatgcagg cactgccctc | 1200 |
| aaaaatggca | agtagtaac | tcatgggggt | agagttcttg | cagtcacagc catccgggaa | 1260 |
| aatctcatat | cagcccttga | ggaagccaag | aaaggactag | ctgctataaa gtttgaggga | 1320 |
| gcaatttata | ggaaagacgt | cggctttcgt | gccatagctt | tcctccagca gcccaggagt | 1380 |
| ttgacttaca | aggaatctgg | agtagatatc | gcagctggaa | atatgctggt caagaaaatt | 1440 |
| cagcctttag | caaaagccac | ttccagatca | ggctgtaaag | ttgatcttgg aggttttgct | 1500 |
| ggtctttttg | atttaaaagc | agctggtttc | aaagatcccc | ttctggcctc tggaacagat | 1560 |
| ggcgttggaa | ctaaactaaa | gattgcccag | ctatgcaata | acatgatac cattggtcaa | 1620 |

-continued

```
gatttggtag caatgtgtgt taatgatatt ctggcacaag gagcagagcc cctcttcttc    1680
cttgattact tttcctgtgg aaaacttgac ctcagtgtaa ctgaagctgt tgttgctgga    1740
attgctaaag cttgtggaaa agctggatgt gctctccttg gaggtgaaac agcagaaatg    1800
cctgacatgt atcccctgg agagtatgac ctagctgggt ttgccgttgg tgccatggag    1860
cgagatcaga aactccctca cctggaaaga atcactgagg gtgatgttgt tgttggaata    1920
gcttcatctg gtcttcatag caatggattt agccttgtga ggaaaatcgt tgcaaaatct    1980
tccctccagt actcctctcc agcacctgat ggttgtggtg accagacttt agggacttta    2040
cttctcacgc ctaccagaat ctacagccat tcactgttac ctgtcctacg ttcaggacat    2100
gtcaaagcct tgcccatat tactggtgga ggattactag agaacatccc cagagtcctc    2160
cctgagaaac ttggggtaga tttagatgcc cagacctgga ggatcccag ggttttctca    2220 tggttgcagc aggaaggaca cctctctgag gaagagatgg ccagaacatt taactgtggg    2280
gttggcgctg tccttgtggt atcaaaggag cagacagagc agattctgag ggatatccag    2340
cagcacaagg aagaagcctg ggtgattggc agtgtggttg cacgagctga aggttcccca    2400
cgtgtgaaag tcaagaatct gattgaaagc atgcaaataa atgggtcagt gttgaagaat    2460
ggctccctga caaatcattt ctcttttgaa aaaaaaagg ccagagtggc tgtcttaata    2520
tctggaacag gatcgaacct gcaagcactt atagacagta ctcgggaacc aaatagctct    2580
gcacaaattg atattgttat ctccaacaaa gccgcagtag ctgggttaga taaagcggaa    2640
agagctggta ttcccactag agtaattaat cataaactgt ataaaaatcg tgtagaattt    2700
gacagtgcaa ttgacctagt ccttgaagag ttctccatag acatagtctg tcttgcagga    2760
ttcatgagaa ttcttttctgg ccccttttgtc caaaagtgga atgaaaaat gctcaatatc    2820 cacccatcct tgctcccttc ttttaagggt tcaaatgccc atgagcaagc cctggaaacc    2880
ggagtcacag ttactgggtg cactgtacac tttgtagctg aagatgtgga tgctggacag    2940
attattttgc aagaagctgt tcccgtgaag aggggtgata ctgtcgcaac tctttctgaa    3000
agagtaaaat tagcagaaca taaaatattt cctgcagccc ttcagctggt ggccagtgga    3060
actgtacagc ttggagaaaa tggcaagatc tgttgggtta agaggaatg aagccttta    3120 attcagaaat ggggccagtt tagaaagaat tatttgctgt ttgcatggtg gtttttatc    3180 atggacttgg cccaaaagaa aaactgctaa agacaaaaa agacctcacc cttacttcat    3240 ctatttttt aataaataga gactcactaa aaaaaaaaa aaaaaaaaa a    3291
```

<210> SEQ ID NO 13
<211> LENGTH: 1776
<212> TYPE: DNA
<213> ORGANISM: Homo sapiens

<400> SEQUENCE: 13

```
atggtgccct ccagcccagc ggtggagaag caggtgcccg tggaacctgg gcctgacccc      60
gagctccggt cctggcggcg cctcgtgtgc tacctttgct tctacggctt catggcgcag     120
atacggccag gggagagctt catcaccccc tacctcctgg ggcccgacaa gaacttcacg     180
cgggacgagg tcacgaacga gatcacgccg gtgctgtcgt actcctacct ggccgtgctg     240
gtgcccgtgt tcctgctcac cgactacctg cgctacacgc cggtgctgct gctgcagggg     300
ctcagcttcg tgtcggtgtg gctgctgctg ctgctgggcc actcggtggc gcacatgcag     360
ctcatggagc tcttctacag cgtcaccatg gccgcgcgca tcgcctattc ctcctacatc     420
```

| | |
|---|---|
| ttctctctcg tgcggcccgc gcgctaccag cgtgtggccg gctactcgcg cgctgcggtg | 480 |
| ctgctgggcg tgttcaccag ctccgtgctg ggccagctgc tggtcactgt gggccgagtc | 540 |
| tccttctcca cgctcaacta catctcgctg gccttcctca ccttcagcgt ggtcctcgcc | 600 |
| ctcttcctga agcgccccaa gcgcagcctc ttcttcaacc gcgacgaccg ggggcggtgc | 660 |
| gaaacctcgg cttcggagct ggagcgcatg aatcctggcc caggcgggaa gctgggacac | 720 |
| gccctgcggg tggcctgtgg ggactcagtg ctggcgcgga tgctgcggga gctggggac | 780 |
| agcctgcggc ggccgcagct gcgcctgtgg tccctctggt gggtcttcaa ctcggccggc | 840 |
| tactacctgg tggtctacta cgtgcacatc ctgtggaacg aggtggaccc caccaccaac | 900 |
| agtgcgcggg tctacaacgg cgcggcagat gctgcctcca cgctgctggg cgccatcacg | 960 |
| tccttcgccg cgggcttcgt gaagatccgc tgggcgcgct ggtccaagct gctcatcgcg | 1020 |
| ggcgtcacgg ccacgcaggc ggggctggtc ttccttctgg cgcacacgcg ccacccgagc | 1080 |
| agcatctggc tgtgctatgc ggccttcgtg ctgttccgcg gctcctacca gttcctcgtg | 1140 |
| cccatcgcca cctttcagat tgcatcttct ctgtctaaag agctctgtgc cctggtcttc | 1200 |
| ggggtcaaca cgttctttgc caccatcgtc aagaccatca tcactttcat tgtctcggac | 1260 |
| gtgcgggggcc tgggcctccc ggtccgcaag cagttccagt tatactccgt gtacttcctg | 1320 |
| atcctgtcca tcatctactt cttgggggcc atgctggatg gctgcgcga ctgccagcgg | 1380 |
| ggccaccacc gcggcagcc cccggcccag ggcctgagga gtgccgcgga ggagaaggca | 1440 |
| gcacagcgac tgagcgtgca ggacaagggc ctcggaggcc tgcagccagc ccagagcccg | 1500 |
| ccgctttccc cagaagacag cctgggggct gtggggccag cctccctgga gcagagacag | 1560 |
| agcgacccat acctgcccca ggccccggcc cgcaggcag ctgaattcct gagcccagtg | 1620 |
| acaaccccctt ccccctgcac tctgtcgtcc gcccaagcct caggccctga ggctgcagat | 1680 |
| gagacttgtc cccagctggc tgtccatcct cctggtgtca gcaagctggg tttgcagtgt | 1740 |
| cttccaagcg acggtgttca gaatgtgaac cagtga | 1776 |

<210> SEQ ID NO 14
<211> LENGTH: 2500
<212> TYPE: DNA
<213> ORGANISM: Homo sapiens

<400> SEQUENCE: 14

| | |
|---|---|
| tgaatcgccc ggggtcgccg tctccgcctc gccgcagtcg gggcagccgc tgccctcttt | 60 |
| tccatgtatc gtccaggatc ccatgacaga ttctgttgtc acgtctcctt acagagtttg | 120 |
| agcggtgctg aactgtcagc acatctgtcc ggtccagcat gccttctgag acccccagg | 180 |
| cagaagtggg gcccacaggc tgcccccacc gctcagggcc acactcggcg aaggggagcc | 240 |
| tggagaaggg gtccccagag gataaggaag ccaaggagcc cctgtggatc cggcccgatg | 300 |
| ctccgagcag gtgcacctgg cagctgggcc ggcctgcctc cgagtcccca catcaccaca | 360 |
| ctgccccggc aaaatctcca aaaatcttgc cagatattct gaagaaaatc ggggacaccc | 420 |
| ctatggtcag aatcaacaag attgggaaga agttcggcct gaagtgtgag ctcttggcca | 480 |
| agtgtgagtt cttcaacgcg ggcgggagcg tgaaggaccg catcagcctg cggatgattg | 540 |
| aggatgctga gcgcgacggg acgctgaagc ccggggacac gattatcgag ccgacatccg | 600 |
| ggaacaccgg gatcgggctg gccctggctg cggcagtgag gggctatcgc tgcatcatcg | 660 |
| tgatgccaga gaagatgagc tccgagaagg tggacgtgct gcgggcactg ggggctgaga | 720 |
| ttgtgaggac gcccaccaat gccaggttcg actccccgga gtcacacgtg ggggtggcct | 780 |

```
ggcggctgaa gaacgaaatc cccaattctc acatcctaga ccagtaccgc aacgccagca      840
accccctggc tcactacgac accaccgctg atgagatcct gcagcagtgt gatgggaagc      900
tggacatgct ggtggcttca gtgggcacgg gcggcaccat cacgggcatt gccaggaagc      960
tgaaggagaa gtgtcctgga tgcaggatca ttggggtgga tcccgaaggg tccatcctcg     1020
cagagccgga ggagctgaac cagacggagc agacaaccta cgaggtggaa gggatcggct     1080
acgacttcat ccccacggtg ctggacagga cggtggtgga caagtggttc aagagcaacg     1140
atgaggaggc gttcaccttt gcccgcatgc tgatcgcgca agaggggctg ctgtgcggtg     1200
gcagtgctgg cagcacggtg gcggtggccg tgaaggctgc gcaggagctg caggagggcc     1260
agcgctgcgt ggtcattctg cccgactcag tgcggaacta catgaccaag ttcctgagcg     1320
acaggtggat gctgcagaag ggctttctga aggaggagga cctcacggag aagaagccct     1380
ggtggtggca cctccgtgtt caggagctgg gcctgtcagc cccgctgacc gtgctcccga     1440
ccatcacctg tgggcacacc atcgagatcc tccgggagaa gggcttcgac caggcgcccg     1500
tggtggatga ggcgggggta atcctgggaa tggtgacgct gggaacatg ctctcgtccc     1560 tgcttgccgg gaaggtgcag ccgtcagacc aagttggcaa agtcatctac aagcagttca     1620
aacagatccg cctcacggac acgctgggca ggctctcgca catcctggag atggaccact     1680
tcgccctggt ggtgcacgag cagatccagt accacagcac cggaagtcc agtcagcggc     1740 agatggtgtt cggggtggtc accgccattg acttgctgaa cttcgtggcc gcccaggagc     1800
gggaccagaa gtgaagtccg gagcgctggg cggtgcggag cggcccgcc acccttgccc     1860 acttctcctt cgctttcctg agccctaaac acacgcgtga ttggtaactg cctggcctgg     1920
caccgttatc cctgcagacg gcacagagca tccgtctccc ctcgttaaca catggcttcc     1980
taaatggccc tgtttacggc ctatgagatg aaatatgtga ttttctctaa tgtaacttcc     2040
tcttaggatg tttcaccaag gaaatattga gagagaagtc ggccaggtag gatgaacaca     2100
ggcaatgact gcgcagagtg gattaaaggc aaaagagaga agagtccagg aaggggcggg     2160
gagaagcctg ggtggctcag catcctccac gggctgcgcg tctgctcggg gctgagctgg     2220
cgggagcagt ttgcgtgttt gggttttta attgagatga aattcaaata acctaaaaat     2280
caatcacttg aaagtgaaca atcagcggca tttagtacat ccagaaagtt gtgtaggcac     2340
cacctctgtc acgttctgga acattctgtc atcaccccgt gaagcaatca tttccccctcc     2400 cgtcttcctc ctccccctggc aactgctgat cgactttgtg tctctgttgt ctaaaatagg     2460
ttttccctgt tctggacatt tcatataaat ggaatcacac                           2500
```

<210> SEQ ID NO 15
<211> LENGTH: 2068
<212> TYPE: DNA
<213> ORGANISM: Homo sapiens

<400> SEQUENCE: 15

```
cggcagccct cctacctgcg cacgtggtgc cgctgctgct gcctcccgct cgccctgaac       60
ccagtgcctg cagccatggc tcccggccag ctcgccttat ttagtgtctc tgacaaaacc      120
ggccttgtgg aatttgcaag aaacctgacc gctcttggtt tgaatctggt cgcttccgga      180
gggactgcaa aagctctcag ggatgctggt ctggcagtca gagatgtctc tgagttgacg      240
ggatttcctg aaatgttggg gggacgtgtg aaaactttgc atcctgcagt ccatgctgga      300
atcctagctc gtaatattcc agaagataat gctgacatgg ccagacttga tttcaatctt      360
```

| | |
|---|---|
| ataagagttg ttgcctgcaa tctctatccc tttgtaaaga cagtggcttc tccaggtgta | 420 |
| actgttgagg aggctgtgga gcaaattgac attggtggag taaccttact gagagctgca | 480 |
| gccaaaaacc acgctcgagt gacagtggtg tgtgaaccag aggactatgt ggtggtgtcc | 540 |
| acggagatgc agagctccga gagtaaggac acctccttgg agactagacg ccagttagcc | 600 |
| ttgaaggcat tcactcatac ggcacaatat gatgaagcaa tttcagatta tttcaggaaa | 660 |
| cagtacagca aaggcgtatc tcagatgccc ttgagatatg aatgaaccc acatcagacc | 720 |
| cctgcccagc tgtacacact gcagcccaag cttcccatca cagttctaaa tggagcccct | 780 |
| ggatttataa acttgtgcga tgcttttgaac gcctggcagc tggtgaagga actcaaggag | 840 |
| gctttaggta ttccagccgc tgcctctttc aaacatgtca gcccagcagg tgctgctgtt | 900 |
| ggaattccac tcagtgaaga tgaggccaaa gtctgcatgg tttatgatct ctataaaacc | 960 |
| ctcacaccca tctcagcggc atatgcaaga gcaagagggg ctgataggat gtcttcattt | 1020 |
| ggtgattttg ttgcattgtc cgatgttgt gatgtaccaa ctgcaaaaat tatttccaga | 1080 |
| gaagtatctg atggtataat tgccccagga tatgaagaag aagccttgac aatactttcc | 1140 |
| aaaaagaaaa atgaaactaa ttgtgtcctt cagatggacc aatcttacaa accagatgaa | 1200 |
| aatgaagttc gaactctctt tggtcttcat ttaagccaga agagaaataa tggtgtcgtc | 1260 |
| gacaagtcat tattagcaa tgttgttacc aaaaataaag atttgccaga gtctgccctc | 1320 |
| cgagacctca tcgtagccac cattgctgtc aagtacactc agtctaactc tgtgtgctac | 1380 |
| gccaagaacg ggcaggttat cggcattgga gcaggacagc agtctcgtat acactgcact | 1440 |
| cgccttgcag gagataaggc aaactattgg tggcttagac accatccaca agtgctttcg | 1500 |
| atgaagttta aaacaggagt gaagagagca gaaatctcca atgccatcga tcaatatgtg | 1560 |
| actggaacca ttggcgagga tgaagatttg ataaagtgga aggcactgtt tgaggaagtc | 1620 |
| cctgagttac tcactgaggc agagaagaag gaatgggttg agaaactgac tgaagtttct | 1680 |
| atcagctctg atgccttctt cccctttccga gataacgtag acagagctaa aaggagtggt | 1740 |
| gtggcgtaca ttgcggctcc ctccggttct gctgctgaca aagttgtgat tgaggcctgc | 1800 |
| gacgaactgg gaatcatcct cgctcatacg aaccttcggc tcttccacca ctgattttac | 1860 |
| cacacactgt ttttggctt gcttatgtgt aggtgaacag tcacgcctga aactttgagg | 1920 |
| ataactttt aaaaaaataa aacagtatct cttaaaacaa tgttttgatc tacataaaca | 1980 |
| ttgtaaaaat tttcaatcac gcttttttaac tttcttacca caaaaaaatg ataagtgggt | 2040 |
| gaagtgatgg ttatgttaat tagcgtgc | 2068 |

<210> SEQ ID NO 16
<211> LENGTH: 857
<212> TYPE: DNA
<213> ORGANISM: Homo sapiens

<400> SEQUENCE: 16

| | |
|---|---|
| gcgtgggcgt gagatggcgg cggcagcggt gagcagcgcc aagcggagcc tgcggggaga | 60 |
| gctgaagcag cgtctgcggg cgatgagtgc cgaggagcgg ctacgccagt cccgcgtact | 120 |
| gagccagaag gtgattgccc acagtgagta tcaaaagtcc aaaagaattt ccatctttct | 180 |
| gagcatgcaa gatgaaattg agacagaaga gatcatcaag gacattttcc aacgaggcaa | 240 |
| aatctgcttc atccctcggt accggttcca gagcaatcac atggatatgg tgagaataga | 300 |
| atcaccagag gaaatttctt tacttcccaa aacatcctgg aatatccctc agcctggtga | 360 |
| gggtgatgtt cgggaggagg ccttgtccac aggggggactt gatctcatct tcatgccagg | 420 |

-continued

| | |
|---|---|
| ccttgggttt gacaaacatg gcaaccgact ggggaggggc aagggctact atgatgccta | 480 |
| tctgaagcgc tgtttgcagc atcaggaagt gaagccctac accctggcgt tggctttcaa | 540 |
| agaacagatt tgcctccagg tcccagtgaa tgaaaacgac atgaaggtag atgaagtcct | 600 |
| ttacgaagac tcgtcaacag cttaaatctg gattactaca gccaataat cagtgtttta | 660 |
| tatgagagta aagcaaagta tgtgtatttt tcccttgtca aaaattagtt gaaattgttc | 720 |
| attaatgtga atacagactg cattttaaaa ttgtaattat gaaataccttt atataaaacc | 780 |
| atctttaaaa accaatagaa gtgtgaatag tagaatatta attaaaatgg aggctatcag | 840 |
| cctgtgattt tcagctt | 857 |

<210> SEQ ID NO 17
<211> LENGTH: 3762
<212> TYPE: DNA
<213> ORGANISM: Homo sapiens

<400> SEQUENCE: 17

| | |
|---|---|
| cccgcgagcg tccatccatc tgtccggccg actgtccagc gaaagggct ccaggccggg | 60 |
| cgcacgtcga cccgggggac cgaggccagg agaggggcca agagcgcggc tgacccttgc | 120 |
| gggccgggc aggggacggt ggccgcggcc atgcagtcct gtgccagggc gtggggctg | 180 |
| cgcctgggcc gcgggtcgg gggcggccgc cgcctggctg ggggatcggg gccgtgctgg | 240 |
| gcgccgcgga gccgggacag cagcagtggc ggcggggaca gcgccgcggc tggggcctcg | 300 |
| cgcctcctgg agcgccttct gcccagacac gacgacttcg ctcggaggca catcggccct | 360 |
| ggggacaaag accagagaga gatgctgcag accttgggc tggcgagcat tgatgaattg | 420 |
| atcgagaaga cggtccctgc caacatccgt ttgaaaagac ccttgaaaat ggaagaccct | 480 |
| gtttgtgaaa atgaaatcct tgcaactctg catgccattt caagcaaaaa ccagatctgg | 540 |
| agatcgtata ttggcatggg ctattataac tgctcagtgc cacagacgat tttgcggaac | 600 |
| ttactggaga actcaggatg gatcacccag tatactccat accagcctga ggtgtctcag | 660 |
| gggaggctgg agagtttact caactaccag accatggtgt gtgacatcac aggcctggac | 720 |
| atggccaatg catccctgct ggatgagggg actgcagccg cagaggcact gcagctgtgc | 780 |
| tacagacaca acaagaggag gaaatttctc gttgatcccc gttgccaccc acagacaata | 840 |
| gctgttgtcc agactcgagc caaatatact ggagtcctca ctgagctgaa gttaccctgt | 900 |
| gaaatggact tcagtggaaa agatgtcagt ggagtgttgt tccagtaccc agacacggag | 960 |
| gggaaggtgg aagactttac ggaactcgtg gagagagctc atcagagtgg gagcctggcc | 1020 |
| tgctgtgcta ctgaccttttt agctttgtgc atcttgaggc cacctggaga atttggggta | 1080 |
| gacatcgccc tgggcagctc ccagagattt ggagtgccac tgggctatgg ggacccccat | 1140 |
| gcagcatttt ttgctgtccg agaaagcttg gtgagaatga tgcctggaag aatggtgggg | 1200 |
| gtaacaagag atgccactgg gaaagaagtg tatcgtcttg ctcttcaaac cagggagcaa | 1260 |
| cacattcgga gagacaaggc taccagcaac atctgtacag ctcaggccct cttggcgaat | 1320 |
| atggctgcca tgtttcgaat ctaccatggt tcccatgggc tggagcatat tgctaggagg | 1380 |
| gtacataatg ccactttgat tttgtcagaa ggtctcaagc gagcagggca tcaactccag | 1440 |
| catgacctgt tctttgatac cttgaagatt cattgtggct gctcagtgaa ggaggtcttg | 1500 |
| ggcaggcgg ctcagcggca gatcaatttt cggcttttttg aggatggcac acttggtatt | 1560 |
| tctcttgatg aaacagtcaa tgaaaaagat ctggacgatt tgttgtggat ctttggttgt | 1620 |

-continued

```
gagtcatctg cagaactggt tgctgaaagc atgggagagg agtgcagagg tattccaggg    1680
tctgtgttca agaggaccag cccgttcctc acccatcaag tgttcaacag ctaccactct    1740
gaaacaaaca ttgtccggta catgaagaaa ctggaaaata agacatttc ccttgttcac     1800
agcatgattc cactgggatc ctgcaccatg aaactgaaca gttcgtctga actcgcacct    1860
atcacatgga agaatttgc aaacatccac ccctttgtgc ctctggatca agctcaagga    1920
tatcagcagc ttttccgaga gcttgagaag gatttgtgtg aactcacagg ttatgaccag    1980
gtctgtttcc agccaaacag cggagcccag ggagaatatg ctggactggc cactatccga    2040
gcctacttaa accagaaagg agaggggcac agaacggttt gcctcattcc gaaatcagca    2100
catgggacca acccagcaag tgcccacatg gcaggcatga agattcagcc tgtggaggtg    2160
gataaatatg ggaatatcga tgcagttcac ctcaaggcca tggtggataa gcacaaggag    2220
aacctagcag ctatcatgat tacatacccca tccaccaatg gggtgtttga agagaacatc    2280
agtgacgtgt gtgacctcat ccatcaacat ggaggacagg tctacctaga cggggcaaat    2340
atgaatgctc aggtgggaat ctgtcgccct ggagacttcg ggtctgatgt ctcgcaccta    2400
aatcttcaca agaccttctg cattcccac ggaggaggtg gtcctggcat ggggcccatc    2460
ggagtgaaga acatctcgc cccgtttttg cccaatcatc ccgtcatttc actaaagcgg     2520
aatgaggatg cctgtcctgt gggaaccgtc agtgcggccc catggggctc cagttccatc    2580
ttgcccattt cctgggctta tatcaagatg atgggaggca agggtcttaa acaagccacg    2640
gaaactgcga tattaaatgc caactacatg gccaagcgat tagaaacaca ctacagaatt    2700
cttttcaggg gtgcaagagg ttatgtgggt catgaattta ttttggacac gagacccttc    2760
aaaaagtctg caaatattga ggctgtggat gtggccaaga gactccagga ttatggatttc    2820
cacgccccta ccatgtcctg gctgtggca gggaccctca tggtggagcc cactgagtcg    2880
gaggacaagg cagagctgga cagattctgt gatgccatga tcagcattcg gcaggaaatt    2940
gctgacattg aggagggccg catcgacccc agggtcaatc cgctgaagat gtctccacac    3000
tccctgacct gcgttacatc ttcccactgg gaccggcctt attccagaga ggtggcagca    3060
ttcccactcc ccttcatgaa accagagaac aaattctggc aacgattgc ccggattgat     3120
gacatatatg gagatcagca cctggttttgt acctgcccac ccatggaagt ttatgagtct    3180
ccattttctg aacaaaagag ggcgtcttct tagtcctctc tccctaagtt taaaggactg    3240
atttgatgcc tctccccaga gcatttgata agcaagaaag atttcatctc ccaccccagc    3300
ctcaagtagg agtttatat actgtgtata tctctgtaat ctctgtcaag gtaaatgtaa    3360
atacagtagc tggagggagt cgaagctgat ggttggaaga cggatttgct ttggtattct    3420
gcttccacat gtgccagttg cctggattgg gagccatttt gtgttttgcg tagaaagttt    3480
taggaacttt aacttttaat gtggcaagtt tgcagatgtc atagaggcta tcctggagac    3540
ttaatagaca tttttttgtt ccaaaagagt ccatgtggac tgtgccatct gtgggaaatc    3600
ccagggcaaa tgtttacatt ttgtataccc tgaagaactc tttttcctct aatatgccta    3660
atctgtaatc acatttctga gtgttttcct cttttttctgt gtgaggtttt tttttttttt    3720
aatctgcatt tattagtatt ctaataaaag cattttgatc gg                         3762
```

<210> SEQ ID NO 18
<211> LENGTH: 1192
<212> TYPE: DNA
<213> ORGANISM: Homo sapiens

<400> SEQUENCE: 18

-continued

| | | | | | |
|---|---|---|---|---|---|
| ggctccctcc | ggccgcgaac | tgccctccc | cgccccgcct | cccggcgcgg | gtggccgagg | 60 |
| cgtagcgccg | cgacccccgc | accctgcga | acatggcgct | gcgagtggtg | cggagcgtgc | 120 |
| gggccctgct | ctgcaccctg | cgcgcggtcc | cgttacccgc | cgcgccctgc | cgccgaggc | 180 |
| cctggcagct | ggggtgggc | gccgtccgta | cgctgcgcac | tggacccgct | ctgctctcgg | 240 |
| tgcgtaaatt | cacagagaaa | cacgaatggg | taacaacaga | aaatggcatt | ggaacagtgg | 300 |
| gaatcagcaa | ttttgcacag | gaagcgttgg | gagatgttgt | ttattgtagt | ctccctgaag | 360 |
| ttgggacaaa | attgaacaaa | caagatgagt | ttggtgcttt | ggaaagtgtg | aaagctgcta | 420 |
| gtgaactata | ttctccttta | tcaggagaag | taactgaaat | taatgaagct | cttgcagaaa | 480 |
| atccaggact | tgtaaacaaa | tcttgttatg | aagatggttg | gctgatcaag | atgcactga | 540 |
| gtaacccttc | agaactagat | gaacttatga | gtgaagaagc | atatgagaaa | tacataaaat | 600 |
| ctattgagga | gtgaaaatgg | aactcctaaa | taaactagta | tgaaataacg | aagccagcag | 660 |
| agttgtctta | aattagtggt | ggatagagac | ttagaataga | aactttagt | attaccgatg | 720 |
| gggcaaaaaa | aaactactgt | taacactgct | aatgaaagaa | atgcccttt | aactttgtaa | 780 |
| tgattataga | taaatataat | atgcgtcttt | ttcacaatat | cctatgatt | ttagactagg | 840 |
| ctctagtgtt | cagaattcat | gaaattatcc | atggtaaaaa | ctagttataa | aaattacata | 900 |
| attcaaagat | aacattgtta | ttcttaagcc | ttatataata | ttgtaacttg | catgtatcca | 960 |
| tacctggatt | tgggatgaaa | tacttaatga | tctttccatt | ggaaataact | ggaagtgaag | 1020 |
| aggttttgtt | gcttgtacag | tgtcagatga | ggaacaccac | tatcttaatt | ttgcgataca | 1080 |
| ctgcatttgc | tggtgctatt | tttatacagt | gaagcaacag | ctttgcagca | aaataataaa | 1140 |
| atacttcttc | gttaaaaaaa | aaaaaaaaaa | aaaaaaaaaa | aaaaaaaaaa | aa | 1192 |

<210> SEQ ID NO 19
<211> LENGTH: 2102
<212> TYPE: DNA
<213> ORGANISM: Homo sapiens

<400> SEQUENCE: 19

| | | | | | |
|---|---|---|---|---|---|
| tgcccacgcc | cccttcagat | cctttgctcc | ggagagagac | ctgtccgagc | agaggcctgg | 60 |
| actacatctc | ccggcgtgcc | tggcagtgtg | gtggcctctg | tgcgccgtct | gcactcgttg | 120 |
| caggcgacga | tgcagagggc | tgtaagtgtg | gtggcccgtc | tgggctttcg | cctgcaggca | 180 |
| ttccccccgg | ccttgtgtcg | tccacttagt | tgcgcacagg | aggtgctccg | caggacaccg | 240 |
| ctctatgact | tccacctggc | ccacggcggg | aaaatggtgg | cgtttgcggg | ttggagtctg | 300 |
| ccagtgcagt | accgggacag | tcacactgac | tcgcacctgc | acacacgcca | gcactgctcg | 360 |
| ctctttgacg | tgtctcatat | gctgcagacc | aagatacttg | gtagtgaccg | ggtgaagctg | 420 |
| atggagagtc | tagtggttgg | agacattgca | gagctaagac | caaaccaggg | gacactgtcg | 480 |
| ctgtttacca | acgaggctgg | aggcatctta | gatgacttga | ttgtaaccaa | tacttctgag | 540 |
| ggccacctgt | atggtgtgtc | caacgctggc | tgctgggaga | agatttggc | cctcatgcag | 600 |
| gacaaggtca | gggagcttca | gaaccagggc | agagatgtgg | gcctggaggt | gttggataat | 660 |
| gccctgctag | ctctgcaagg | ccccactgca | gcccaggtac | tacaggccgg | cgtggcagat | 720 |
| gacctgagga | aactgcccct | catgaccagt | gctgtgatgg | aggtgtttgg | cgtgtctggc | 780 |
| tgccgcgtga | cccgctgtgg | ctacacagga | gaggatggtg | tggagatctc | ggtgccggta | 840 |
| gcgggggcag | ttcacctggc | aacagctatt | ctgaaaaacc | cagaggtgaa | gctggcaggg | 900 |

```
ctggcagcca gggacagcct gcgcctggag gcaggcctct gcctgtatgg gaatgacatt      960
gatgaacaca ctacacctgt ggagggcagc ctcagttgga cactgggaa  gcgccgccga     1020
gctgctatgg acttccctgg agccaaggtc attgttcccc agctgaaggg cagggtgcag     1080
cggaggcgtg tggggttgat gtgtgagggg cccccatgc  gggcacacag tcccatcctg     1140
aacatggagg gtaccaagat tggtactgtg actagtggct gccccctccc ctctctgaag     1200
aagaatgtgg cgatgggtta tgtgccctgc gagtacagtc gtccagggac aatgctgctg     1260
gtagaggtgc ggcggaagca gcagatggct gtagtcagca agatgccctt tgtgcccaca     1320
aactactata ccctcaagtg aagctggctc agggtgggc  tgtcccttcc aggagttttg     1380
cccctacaag gggttagtca agaagctgag gcagaactca ctgggggtgg cagttaagg     1440
tggaggctga ttctaattgt ctggttgagg ggccacacca cctattcccc ccacctaact     1500
catgccattc cagcttcctt caggaccctg cttctgagtg acggaccagc tcacacaatg     1560
tcttgtttca gtccatgatc ccactgacct actcttgcct gctggagggt aatgagaagc     1620
tttggttctg ccatctctcc cactctgcca ggtgctggct gtggagcaaa ggctcacctt     1680
tgtggagaga ataaaacctg cccaacctac ctcaccatgg tttttcacat tgcaaagggt     1740
aataacatgg gcagtgcgga cttaggctac cccctccagt ttgctttccg taaatgcaaa     1800
ttgtccttac tgcaagtcag gaatgattgc tgactcacag tagggctgct atgcctgtgt     1860
gtaaacttgg ggatggctga gggaacatag actcactctt ccacattccc aagttggtct     1920
agtgtgctgc ccagtagcaa accatggcag actcaccacc tattctgagt tccagggctg     1980
ctgtagggca gggtgggctt cctcccagac ttgccttacc ctgggctgat ctttgccct     2040
ggtatgcatt aatggactcc actgaatcct gaaaaaaaaa ttaaacttcc ttcttacttg     2100
cc                                                                    2102

<210> SEQ ID NO 20
<211> LENGTH: 3228
<212> TYPE: DNA
<213> ORGANISM: Homo sapiens

<400> SEQUENCE: 20
aaaaaactca ggcaaagtca cagcctcaaa attgttcact gaaagaacgc tgagtggaga       60
agtgtgagaa gatgaatgga ccggtggatg gcttgtgtga ccactctcta agtgaaggag      120
tcttcatgtt cacatcggag tctgtgggag agggacaccc ggataagatc tgtgaccaga      180
tcagtgatgc agtgctggat gcccatctca agcaagaccc caatgccaag gtggcctgtg      240
agacagtgtg caagaccggc atggtgctgc tgtgtggtga gatcacctca atggccatgg      300
tggactacca gcgggtggtg agggacacca tcaagcacat cggctacgat gactcagcca      360
agggctttga cttcaagact tgcaacgtgc tggtggcttt ggagcagcaa tccccagata      420
ttgcccagtg cgtccatctg gacagaaatg aggaggatgt gggggcagga gatcagggtt      480
tgatgttcgg ctatgctacc gacgagacag aggagtgcat gcccctcacc atcatccttg      540
ctcacaagct caacgcccgg atggcagacc tcaggcgctc cggcctcctc ccctggctgc      600
ggcctgactc taagactcag gtgacagttc agtacatgca ggacaatggc agtcatcc        660
ctgtgcgcat ccacaccatc gtcatctctg tgcagcacaa cgaagacatc acgctggagg      720
agatgcgcag ggccctgaag gagcaagtca tcagggccgt ggtgccggcc aagtacctgg      780
acgaagacac cgtctaccac ctgcagccca gtgggcggtt tgtcatcgga ggtcccagg      840
gggatgcggg tgtcactggc cgtaagatta ttgtggacac ctatggcggc tgggggggctc      900
```

-continued

```
atggtggtgg ggccttctct gggaaggact acaccaaggt agaccgctca gctgcatatg      960
ctgcccgctg ggtggccaag tctctggtga agcagggct ctgccggaga gtgcttgtcc      1020
aggtttccta tgccattggt gtggccgagc cgctgtccat ttccatcttc acctacggaa      1080
cctctcagaa gacagagcga gagctgctgg atgtggtgca taagaacttc gacctccggc      1140
cgggcgtcat tgtcagggat ttggacttga gaagcccat ctaccagaag acagcatgct      1200
acggccattt cggaagaagc gagttcccat gggaggttcc caggaagctt gtattttaga      1260
gccaggggga gctgggcctg tctcaccct ggaggcacct ggtggccatg ctcctcttcc       1320
ccagacgcct ggctgctgat cgccttcccc acccaccaac cctcagggca aagccaggtc      1380
cctctcattt agcctgtcct gtcatcatca tggccagctg gaggcagggg cttcctggtg      1440
ctggaggttg gatcttgatg taaggatggg catggtgttc tcctgctgct ccctcagact      1500
ggggcaatgt taatttagtg gaaaaggcac ccccgtcaag agtgaattcc ctcactcgtc      1560
tcccccaaca gctggaccct gaccagctcc ccctccctcc ccttgcctgt gccaggtgag      1620
gtcagcacat ctcaacaggc ctcagggctc cttgtgggcc tgggctcctg gaccccctt      1680
tcacaggcag ccagtgccct gagccagggt ctccagaaag ccccacccag gccaggcatg      1740
tgcaggggt tagagcagga ctgatgtctc ctaagcacct gtaatgtgcg agggacccag      1800
ctaataactg atctcgtttt ttcttcactg caacatgatg aggtagtacc ttttatatcc      1860
catttataga tggggaaaag caaagcacag agagtctgga taacttccac agggtcccac      1920
agccacgtgt ttagacctag atgtataact aggagctttg actcaggagc ctgtgacata      1980
cccccttccc caccgttgtc tcatgccagt aacaggctca aacaatgaca aagcagattc      2040
agaaatgagg ccatggactc tgtcctgaag gcctgaggtt actggaaatt agggattaa       2100
cccactagct cttgttgagc cgtgggcaat tgtctgaaaa gtgaagacag aaccacaggg      2160
ctattttgtt tgcttcatgt gtcccagaag atgactgagg gtgagttggc ttacctggcc      2220
catcaggta ggctggagtt agggactgac cagcagcttt agaatcccag cccctgacc       2280
actcagagac atgcagagat tgggttttg gacttctggg gtaagtggtc taagtccagt      2340
ccagtcctat gtgggcttcc tggagcagaa gcagcaactt gtcctagcac agatggccag      2400
cccccttagac agaggccctc aagtctttct ctttccctgg tcccttgtat ccctgcagg      2460
ctgagtgcat ttggagggag tgagtggccc tttcggatcc agggaggctg gtcctatggc      2520
ctcatgttaa ataggcgggg cttgccttct ggtgttggac aagcttctga gacgtcatga      2580
ggagattctg cctttgccag gtgactgtct ggggagcggg tctgctccca aggggcctga      2640
gcagtccttg gcctgctaag gtcttggaac ttgcctgcct ttccatccat ggccagcagc      2700
acctgcccta cctgccccac ttgtccttag cctggacctc tgacagcagc atctctacct      2760
tctcccagc tcccaggacc acaggctcag gcagggcctc catgggcccc agggaacac        2820
tggggacttg gcctctctct agggtacatg gtgctgggag aggcagccca ggaagtctca      2880
tctggggagc aggcagccag catctgggcc ttggcctgga gcacaaagac cctggctttc      2940
attttctctc aggtgaaagg aaattaaggc aacaaaagaa gcccggctcc tggtcaccta      3000
ggaagcctca gattccttcc catggaggga gggagtggtt tgcaggtggc caagttcctc      3060
taacttggct cacactcgac atgaaaattc agaatttat actttcccta ccctctagag       3120
aaataagatc ttttttgtca gtttgtttgt atgaaactaa agctttattt gttaatagtt      3180
cctgctaaaa caatgaataa aaactcaagg agcaactaaa aaaaaaa                    3228
```

<210> SEQ ID NO 21
<211> LENGTH: 344
<212> TYPE: PRT
<213> ORGANISM: Homo sapiens

<400> SEQUENCE: 21

```
Met Ser Ala Leu Ala Ala Arg Leu Leu Gln Pro Ala His Ser Cys Ser
  1               5                  10                  15

Leu Arg Leu Arg Pro Phe His Leu Ala Ala Val Arg Asn Glu Ala Val
                 20                  25                  30

Val Ile Ser Gly Arg Lys Leu Ala Gln Gln Ile Lys Gln Glu Val Arg
             35                  40                  45

Gln Glu Val Glu Glu Trp Val Ala Ser Gly Asn Lys Arg Pro His Leu
         50                  55                  60

Ser Val Ile Leu Val Gly Glu Asn Pro Ala Ser His Ser Tyr Val Leu
 65                  70                  75                  80

Asn Lys Thr Arg Ala Ala Val Val Gly Ile Asn Ser Glu Thr Ile
                 85                  90                  95

Met Lys Pro Ala Ser Ile Ser Glu Glu Glu Leu Leu Asn Leu Ile Asn
                100                 105                 110

Lys Leu Asn Asn Asp Asp Asn Val Asp Gly Leu Leu Val Gln Leu Pro
            115                 120                 125

Leu Pro Glu His Ile Asp Glu Arg Arg Ile Cys Asn Ala Val Ser Pro
        130                 135                 140

Asp Lys Asp Val Asp Gly Phe His Val Ile Asn Val Gly Arg Met Cys
145                 150                 155                 160

Leu Asp Gln Tyr Ser Met Leu Pro Ala Thr Pro Trp Gly Val Trp Glu
                165                 170                 175

Ile Ile Lys Arg Thr Gly Ile Pro Thr Leu Gly Lys Asn Val Val Val
                180                 185                 190

Ala Gly Arg Ser Lys Asn Val Gly Met Pro Ile Ala Met Leu Leu His
            195                 200                 205

Thr Asp Gly Ala His Glu Arg Pro Gly Gly Asp Ala Thr Val Thr Ile
        210                 215                 220

Ser His Arg Tyr Thr Pro Lys Glu Gln Leu Lys Lys His Thr Ile Leu
225                 230                 235                 240

Ala Asp Ile Val Ile Ser Ala Ala Gly Ile Pro Asn Leu Ile Thr Ala
                245                 250                 255

Asp Met Ile Lys Glu Gly Ala Ala Val Ile Asp Val Gly Ile Asn Arg
                260                 265                 270

Val His Asp Pro Val Thr Ala Lys Pro Lys Leu Val Gly Asp Val Asp
            275                 280                 285

Phe Glu Gly Val Arg Gln Lys Ala Gly Tyr Ile Thr Pro Val Pro Gly
        290                 295                 300

Gly Val Gly Pro Met Thr Val Ala Met Leu Met Lys Asn Thr Ile Ile
305                 310                 315                 320

Ala Ala Lys Lys Val Leu Arg Leu Glu Glu Arg Glu Val Leu Lys Ser
                325                 330                 335

Lys Glu Leu Gly Val Ala Thr Asn
            340
```

<210> SEQ ID NO 22
<211> LENGTH: 1283
<212> TYPE: DNA
<213> ORGANISM: Homo sapiens

<400> SEQUENCE: 22

```
tttcgcagcc gctgccgcct cgccgctgct ccttcgtaag gccacttccg cacaccgaca    60
ccaacatgaa cggacagctc aacggcttcc acgaggcgtt catcgaggag ggcacattcc   120
ttttcacctc agagtcggtc ggggaaggcc acccagataa gatttgtgac caaatcagtg   180
atgctgtcct tgatgcccac cttcagcagg atcctgatgc caaagtagct tgtgaaactg   240
ttgctaaaac tggaatgatc cttcttgctg gggaaattac atccagagct gctgttgact   300
accagaaagt ggttcgtgaa gctgttaaac acattggata tgatgattct tccaaaggtt   360
ttgactacaa gacttgtaac gtgctggtag ccttggagca acagtcacca gatattgctc   420
aaggtgttca tcttgacaga atgaagaag acattggtgc tggagaccag ggcttaatgt   480
ttggctatgc cactgatgaa actgaggagt gtatgccttt aaccattgtc ttggcacaca   540
agctaaatgc caaactggca gaactacgcc gtaatggcac tttgccttgg ttacgccctg   600
attctaaaac tcaagttact gtgcagtata tgcaggatcg aggtgctgtg cttcccatca   660
gagtccacac aattgttata tctgttcagc atgatgaaga ggtttgtctt gatgaaatga   720
gggatgccct aaaggagaaa gtcatcaaag cagttgtgcc tgcgaaatac cttgatgagg   780
atacaatcta ccacctacag ccaagtggca gatttgttat tggtgggcct cagggtgatg   840
ctggtttgac tggacggaaa atcattgtgg acacttatgg cggttggggt gctcatggag   900
gaggtgcctt tcaggaaag gattatacca aggtcgaccg ttcagctgct tatgctgctc   960
gttgggtggc aaaatcccct tgttaaaggag gtctgtgccg gagggttctt gttcaggtct  1020
cttatgctat tggagtttct catccattat ctatctccat tttccattat ggtacctctc  1080
agaagagtga gagagagcta ttagagattg tgaagaagaa tttcgatctc cgccctgggg  1140
tcattgtcag ggatctggat ctgaagaagc caatttatca gaggactgca gcctatggcc  1200
actttggtag ggacagcttc ccatgggaag tgcccaaaaa gcttaaatat tgaaagtgtt  1260
agccttttt ccccagactt gtt                                           1283
```

<210> SEQ ID NO 23
<211> LENGTH: 3259
<212> TYPE: DNA
<213> ORGANISM: Homo sapiens

<400> SEQUENCE: 23

```
caaggttggt ggaagtcgcg ttgtgcaggt tcgtgcccgg ctggcgcggc gtggtttcac    60
tgttacatgc cttgaagtga tgaggaggtt tctgttacta tatgctacac agcagggaca   120
ggcaaaggcc atcgcagaag aaatgtgtga gcaagctgtg gtacatggat tttctgcaga   180
tcttcactgt attagtgaat ccgataagta tgacctaaaa accgaaacag ctcctcttgt   240
tgttgtggtt tctaccacgg gcaccggaga cccacccgac acagcccgca agtttgttaa   300
ggaaatacag aaccaaacac tgccggttga tttctttgct cacctgcggt atgggttact   360
gggtctcggt gattcagaat acacctactt tgcaatgggg ggaagataa ttgataaacg   420
acttcaagag cttggagccc ggcatttcta tgacactgga catgcagatg actgtgtagg   480
tttagaactt gtggttgagc cgtggattgc tggactctgg ccagccctca gaaagcattt   540
taggtcaagc agaggacaag aggagataag tggcgcactc ccggtggcat cacctgcatc   600
cttgaggaca gaccttgtga agtcagagct gctacacatt gaatctcaag tcgagcttct   660
gagattcgat gattcaggaa gaaaggattc tgaggttttg aagcaaaatg cagtgaacag   720
```

```
caaccaatcc aatgttgtaa ttgaagactt tgagtcctca cttacccgtt cggtaccccc      780
actctcacaa gcctctctga atattcctgg tttaccccca gaatatttac aggtacatct      840
gcaggagtct cttggccagg aggaaagcca agtatctgtg acttcagcag atccagtttt      900
tcaagtgcca atttcaaagg cagttcaact tactacgaat gatgccataa aaaccactct      960
gctggtagaa ttggacattt caaatacaga cttttcctat cagcctggag atgccttcag     1020
cgtgatctgc cctaacagtg attctgaggt acaaagccta ctccaaagac tgcagcttga     1080
agataaaaga gagcactgcg tccttttgaa aataaaggca gacacaaaga gaaaggagc      1140 taccttaccc cagcatatac ctgcgggatg ttctctccag ttcattttta cctggtgtct     1200
tgaaatccga gcaattccta aaaaggcatt tttgcgagcc cttgtggact ataccagtga     1260
cagtgctgaa aagcgcaggc tacaggagct gtgcagtaaa caaggggcag ccgattatag     1320
ccgctttgta cgagatgcct gtgcctgctt gttggatctc ctcctcgctt tcccttcttg     1380
ccagccacca ctcagtctcc tgctcgaaca tcttcctaaa cttcaaccca gaccatattc     1440
gtgtgcaagc tcaagtttat ttcacccagg aaagctccat tttgtcttca acattgtgga     1500
atttctgtct actgccacaa cagaggttct gcggaaggga gtatgtacag gctggctggc     1560
cttgttggtt gcttcagttc ttcagccaaa catacatgca tcccatgaag acagcgggaa     1620
agccctggct cctaagatat ccatctctcc tcgaacaaca aattctttcc acttaccaga     1680 tgaccccctca atccccatca taatggtggg tccaggaacc ggcatagccc cgtttattgg     1740
gttcctacaa catagagaga aactccaaga acaacaccca gatggaaatt ttggagcaat     1800
gtggttgttt tttggctgca ggcataagga tagggattat ctattcagaa aagagctcag     1860
acatttcctt aagcatggga tcttaactca tctaaaggtt tccttctcaa gagatgctcc     1920
tgttggggag gaggaagccc cagcaaagta tgtacaagac aacatccagc ttcatggcca     1980
gcaggtggcg agaatcctcc tccaggagaa cggccatatt tatgtgtgtg agatgcaaa     2040 gaatatggcc aaggatgtac atgatgccct tgtgcaaata ataagcaaag aggttggagt     2100
tgaaaaacta gaagcaatga aaaccctggc cactttaaaa gaagaaaaac gctaccttca     2160
ggatatttgg tcataaaacc agaaattaaa gaaagaggat taagctttttt tgactgaaag     2220 tactaaaagt cagctttact agtgccaaac ctttaaattt tcaaaagaaa attttctttc     2280
aacatttctt gaaggacatg gagtggagat tggatcattt aacaatataa caaaacttcc     2340
tgatttgatt ttacgtatct tctatctacg cccttcctgt gcctgtgact ctccccaaat     2400
tgccctgttg ccttgagctc ttctgagcta aaggcagcct tcagtcccta tcagcgcctc     2460
ctttacttcc cagagaactt cacagagact ctgtccttcc atgcaaaggc ttcctgaaat     2520 agggggagact gactgagtag ctcattcttg tgacttacag tgccaacatt taaaaaagta     2580
tgaaaatgat ttatttttat atgatgtata cccataaaga atgctcatat taatgtactt     2640
aaattacaca tgtagagcat atctgttata tgttatgta actatcaaat ggttatttgt     2700
tactaaagct atatttctga taaaaaatat tttaggataa ttgcctacag agggatttat     2760
ttttatgatg ctgggaaata tgaaatgtat tttaaaattt cactctgggc atatggattt     2820
atctatcacc attactttttt tttaagtcac aatttcagaa ttttgggaca tttgcattca     2880
atttacaggt accagtacgt acatatttta atagaaagat acaacctttt tatttcact      2940 cctttattt ctgctgcttg gcacatttt gagttttccc acattatttg tctccatgat      3000
accactcaag cagtgtgctg gacctaaaat actgacttta gttagtatcc ttggatttt      3060 agattcccca gtgtctaatt ccctgttata atttgcacaa acaaaacaaa atgttatgat     3120
```

```
aatctttctc cactgttcta atatatattg tatttttatt tgatagcttg ggatttaaaa    3180
catctctgtt gaaggctttt gatccttttg agaaataaag atctgaaaga aatggcataa    3240
tcttaaaaaa aaaaaaaaa                                                 3259

<210> SEQ ID NO 24
<211> LENGTH: 1805
<212> TYPE: DNA
<213> ORGANISM: Homo sapiens

<400> SEQUENCE: 24
aagagactga actgtatctg cctctatttc caaaagactc acgttcaact ttcgctcaca      60
caaagccggg aaaatttat tagtccttt tttaaaaaaa gttaatataa aattatagca     120
aaaaaaaaaa ggaacctgaa ctttagtaac acagctggaa caatcgcagc ggcggcggca     180
gcggcgggag aagaggttta atttagttga ttttctgtgg ttgttggttg ttcgctagtc     240
tcacggtgat ggaagctgca cattttttcg aagggaccga gaagctgctg gaggtttggt     300
tctcccggca gcagcccgac gcaaaccaag gatctgggga tcttcgcact atcccaagat     360
ctgagtggga catacttttg aaggatgtgc aatgttcaat cataagtgtg acaaaaactg     420
acaagcagga agcttatgta ctcagtgaga gtagcatgtt tgtctccaag agacgtttca     480
ttttgaagac atgtggtacc accctcttgc tgaaagcact ggttcccctg ttgaagcttg     540
ctagggatta cagtgggttt gactcaattc aaagcttctt ttattctcgt aagaatttca     600
tgaagccttc tcaccaaggg tacccacacc ggaatttcca ggaagaaata gagtttctta     660
atgcaatttt cccaaatgga gcaggatatt gtatgggacg tatgaattct gactgttggt     720
acttatatac tctggatttc ccagagagtc gggtaatcag tcagccagat caaaccttgg     780
aaattctgat gagtgagctt gacccagcag ttatggacca gttctacatg aaagatggtg     840
ttactgcaaa ggatgtcact cgtgagagtg gaattcgtga cctgatacca ggttctgtca     900
ttgatgccac aatgttcaat ccttgtgggt attcgatgaa tggaatgaaa tcggatggaa     960
cttattggac tattcacatc actccagaac cagaattttc ttatgttagc tttgaaacaa    1020
acttaagtca gacctcctat gatgacctga tcaggaaagt tgtagaagtc ttcaagccag    1080
gaaaatttgt gaccaccttg tttgttaatc agagttctaa atgtcgcaca gtgcttgctt    1140
cgccccagaa gattgaaggt tttaagcgtc ttgattgcca gagtgctatg ttcaatgatt    1200
acaatttttgt ttttaccagt tttgctaaga agcagcaaca acagcagagt tgattaagaa    1260
aaatgaagaa aaaacgcaaa agagaacac atgtagaagg tggtggatgc tttctagatg    1320
tcgatgctgg gggcagtgct ttccataacc accactgtgt agttcagaa agccctagat    1380
gtaatgatag tgtaatcatt tgaattgta tgcattatta tatcaaggag ttagatatct    1440
tgcatgaatg ctctcttctg tgtttaggta ttctctgcca ctcttgctgt gaaattgaag    1500
tggatgtaga aaaaaccttt tactatatga aactttacaa cacttgtgaa agcaactcaa    1560
tttggtttat gcacagtgta atatttctcc aagtatcatc caaaattccc cacagacaag    1620
gctttcgtcc tcattaggtg ttggcctcag cctaaccctc taggactgtt ctattaaatt    1680
gctgccagaa ttttacatcc agttacctcc actttctaga acatattctt tactaatgtt    1740
attgaaacca atttctactt catactgatg tttttggaaa cagcaattaa agttttctt    1800
ccatg                                                                1805

<210> SEQ ID NO 25
```

-continued

```
<211> LENGTH: 254
<212> TYPE: PRT
<213> ORGANISM: Homo sapiens

<400> SEQUENCE: 25

Gln Asp Ile Leu Val Phe Arg Ser Lys Thr Tyr Gly Asn Val Leu Val
 1               5                  10                  15

Leu Asp Gly Val Ile Gln Cys Thr Glu Arg Asp Glu Phe Ser Tyr Gln
                20                  25                  30

Glu Met Ile Ala Asn Leu Pro Leu Cys Ser His Pro Asn Pro Arg Lys
         35                  40                  45

Val Leu Ile Ile Gly Gly Asp Gly Gly Val Leu Arg Glu Val Val
     50                  55                  60

Lys His Pro Ser Val Glu Ser Val Val Gln Cys Glu Ile Asp Glu Asp
 65                  70                  75                  80

Val Ile Gln Val Ser Lys Lys Phe Leu Pro Gly Met Ala Ile Gly Tyr
                 85                  90                  95

Ser Ser Ser Lys Leu Thr Leu His Val Gly Asp Gly Phe Glu Phe Met
            100                 105                 110

Lys Gln Asn Gln Asp Ala Phe Asp Val Ile Ile Thr Asp Ser Ser Asp
        115                 120                 125

Pro Met Gly Pro Ala Glu Ser Leu Phe Lys Glu Ser Tyr Tyr Gln Leu
    130                 135                 140

Met Lys Thr Ala Leu Lys Glu Asp Gly Val Leu Cys Cys Gln Gly Glu
145                 150                 155                 160

Cys Gln Trp Leu His Leu Asp Leu Ile Lys Glu Met Arg Gln Phe Cys
                165                 170                 175

Gln Ser Leu Phe Pro Val Val Ala Tyr Ala Tyr Cys Thr Ile Pro Thr
            180                 185                 190

Tyr Pro Ser Gly Gln Ile Gly Phe Met Leu Cys Ser Lys Asn Pro Ser
        195                 200                 205

Thr Asn Phe Gln Glu Pro Val Gln Pro Leu Thr Gln Gln Gln Val Ala
    210                 215                 220

Gln Met Gln Leu Lys Tyr Tyr Asn Ser Asp Val His Arg Ala Ala Phe
225                 230                 235                 240

Val Leu Pro Glu Phe Ala Arg Lys Ala Leu Asn Asp Val Ser
                245                 250

<210> SEQ ID NO 26
<211> LENGTH: 2211
<212> TYPE: DNA
<213> ORGANISM: Homo sapiens

<400> SEQUENCE: 26
ctgaggccca gcccccttcg cccgtttcca tcacgagtgc cgccagcatg tctgacaaac      60
tgccctacaa agtcgccgac atcggcctgg ctgcctgggg acgcaaggcc ctggacattg     120
ctgagaacga gatgccgggc ctgatgcgta tgcgggagcg gtactcggcc tccaagccac     180
tgaagggcgc ccgcatcgct ggctgcctgc acatgaccgt ggagacggcc gtcctcattg     240
agaccctcgt cacccctggg gctgaggtgc agtggtccag ctgcaacatc ttctccaccc     300
agaaccatgc ggcggctgcc attgccaagg ctggcattcc ggtgtatgcc tggaagggcg     360
aaacggacga ggagtacctg tggtgcattg agcagaccct gtacttcaag gacgggcccc     420
tcaacatgat tctggacgac gggggcgacc tcaccaacct catccacacc aagtacccgc     480
agcttctgcc aggcatccga ggcatctctg aggagaccac gactggggtc acaacctct     540
```

-continued

```
acaagatgat ggccaatggg atcctcaagg tgcctgccat caatgtcaat gactccgtca      600
ccaagagcaa gtttgacaac ctctatggct gccgggagtc cctcatagat ggcatcaagc      660
gggccacaga tgtgatgatt gccggcaagg tagcggtggt agcaggctat ggtgatgtgg      720
gcaagggctg tgcccaggcc ctgcggggtt tcggagcccg cgtcatcatc accgagattg      780 acccatcaa cgcactgcag gctgccatgg agggctatga ggtgaccacc atggatgagg       840
cctgtcagga gggcaacatc tttgtcacca ccacaggctg tattgacatc atccttggcc      900
ggtaggtgcc agatgggggg tcccggggag tgagggagga gggcagagtt gggacagctt      960
tctgtccctg acaatctccc acggtcttgg gctgcctgac aggcactttg agcagatgaa     1020
ggatgatgcc attgtgtgta acattggaca ctttgacgtg gagatcgatg tcaagtggct     1080
caacgagaac gccgtggaga aggtgaacat caagccgcag gtggaccggt atcggttgaa     1140
gaatgggcgc cgcatcatcc tgctggccga gggtcggctg gtcaacctgg ttgtgccat      1200 ggccacccc agcttcgtga tgagtaactc cttcaccaac caggtgatgg cgcagatcga      1260
gctgtggacc catccagaca agtaccccgt tggggttcat ttcctgccca agaagctgga     1320
tgaggcagtg gctgaagccc acctgggcaa gctgaatgtg aagttgacca agctaactga     1380
gaagcaagcc cagtacctgg gcatgtcctg tgatggcccc ttcaagccgg atcactaccg     1440
ctactgagag ccaggtctgc gtttcaccct ccagctgctg tccttgccca ggccccacct     1500
ctcctcccta agagctaatg gcaccaactt tgtgattggt ttgtcagtgt ccccatcga      1560 ctctctgggg ctgatcactt agttttggc ctctgctgca gccgtcatac tgttccaaat      1620
gtggcagcgg gaacagagta ccctcttcaa gccccggtca tgatggaggt cccagccaca     1680
gggaaccatg agctcagtgg tcttggaaca gctcactaag tcagtccttc cttagcctgg     1740
aagtcagtag tggagtcaca aagcccatgt gttttgccat ctaggccttc acctggtctg     1800
tggacttata cctgtgtgct tggtttacag gtccagtggt tcttcagccc atgacagatg     1860 agaagggct atattgaagg gcaaagagga actgttgttt gaattttcct gagagcctgg      1920
cttagtgctg ggccttctct taaacctcat tacaatgagg ttagtacttt tagtccctgt    1980
tttacagggg ttagaataga ctgttaaggg gcaactgaga agaacagag aagtgacagc      2040 taggggttga gaggggccag aaaaacatga atgcaggcag atttcgtgaa atctgccacc     2100
actttataac cagatggttc cttcacaac cctgggtcaa aagagaata atttggccta       2160 taatgttaaa agaaagcagg aaggtgggta aataaaaatc ttggtgcctg g             2211
```

<210> SEQ ID NO 27
<211> LENGTH: 2436
<212> TYPE: DNA
<213> ORGANISM: Homo sapiens

<400> SEQUENCE: 27

```
cgaccacctg tctggacacc acaaagatgc cacccgttgg gggcaaaaag gccaagaagg       60
gcatcctaga acgtttaaat gctggagaga ttgtgattgg agatggaggg tttgtctttg      120
cactggagaa gaggggctac gtaaaggcag accctggac tcctgaagct gctgtggagc      180
acccagaagc agttcgccag cttcatcgag agttcctcag agctggctca aacgtcatgc      240
agaccttcac cttctatgcg agtgaagaca agctggagaa caggggcaac tatgtcttag      300
agaagatatc tggcaggaa gtcaatgaag ctgcttgcga catcgcccga caagtggctg       360
atgaaggaga tgctttggta gcaggaggag tgagtcagac accttcatac cttagctgca     420
```

-continued

```
agagtgaaac tgaagtcaaa aaagtatttc tgcaacagtt agaggtcttt atgaagaaga      480
acgtggactt cttgattgca gagtattttg aacacgttga agaagctgtg tgggcagttg      540
aaaccttgat agcatccggt aaacctgtgg cagcaaccat gtgcattggc ccagaaggag      600
atttgcatgg cgtgcccccc ggcgagtgtg cagtgcgcct ggtgaaagca ggagcatcca      660
tcattggtgt gaactgccac tttgacccca ccattagttt aaaaacagtg aagctcatga      720
aggagggctt ggaggctgcc caactgaaag ctcacctgat gagccagccc ttggcttacc      780
acactcctga ctgcaacaag cagggattca tcgatctccc agaattccca tttggactgg      840
aacccagagt tgccaccaga tgggatattc aaaaatacgc cagagaggcc tacaacctgg      900
gggtcaggta cattggcggg tgctgtggat ttgagcccta ccacatcagg gcaattgcag      960
aggagctggc cccagaaagg ggcttttttgc caccagcttc agaaaaacat ggcagctggg     1020
gaagtggttt ggacatgcac accaaacccct gggttagagc aagggccagg aaggaatact     1080
gggagaatct tcggatagcc tcaggccggc catacaaccc ttcaatgtca agccagatg      1140 gctggggagt gaccaaagga acagccgagc tgatgcagca gaaagaagcc acaactgagc     1200
agcagctgaa agagctcttt gaaaaacaaa aattcaaatc acagtagcct cgatagaagc     1260 tattttttgat gaatttctag gtgtttgggt cacagttcct acaaatacgg aaaaggggt      1320 taaaaagcag tgcttttcatg aatgccatcc tacacatatt attgctatta cctgaacaaa     1380
atagaattac aaatagcact tgataatttt aaagtatgtt ttagaaattt tcttaggagc     1440
aaaataagta caaagtaaat cttgaacagg ttcactaagc acccaccctg tgaaaagtat     1500
tatggaaatc actgcagcac aggaaaagta attcagatgt taatgccact tgaagaagtt     1560
ggtaggctag caaagaggat gagacatgaa ctgtcataaa ggactcagca accagccagg     1620
gacagataaa gcgctatgga aaggggcttc caagttcttt tgaacatgac ccttagtaac     1680
aaacacaatt tatataatga cccagcaaaa cacatcacat cttactgtcg aaattaaatg     1740
tgtgatccat cctagtattt tctgttccat tcctttttcat tctatttcat ttataaaaca     1800
tgctagttga gacttttcaa atggatttttt atgacccact actgggtttg gatccacagt     1860
ttgaaaaata ttgctacaag acacttaagg agaccatcct gtttaagttt attcttataa     1920
gtaggtcagt catatgagac ctgatcaata aatatccaat acccagagtc ctgctctcag     1980
agttcttctg tttcgtgacc cacttttcta ccagtaaaag acatagacca atggggagga     2040
ggggaggaga gatggatatt tcagccctct ccatcctagt caacactgga tccacctagt     2100
gcctctgggc cataaggctg agcagagtga gcttgtatta gttggtagct tttaaaaaat     2160
ataataaaaa aaagtagag attctccaaa ctctagcctg gtttcctaga ttgagaacta     2220 tgatatttt ctctgataat ttaatatcta ctctcctaca aaagctcaag cctgaagata     2280
caagactatt agaagaaaca tgactacccct cagtgtatta gaaaagaggt catgcagctt     2340
tctaaacatt attgaattgt ttgagctgtt ttgaaattgt aattcttttc agctattaaa     2400 agaagagca atgagaaaaa aaaaaaaaaa aaaaaa                                 2436
```

<210> SEQ ID NO 28
<211> LENGTH: 1326
<212> TYPE: DNA
<213> ORGANISM: Homo sapiens

<400> SEQUENCE: 28

```
ttcttttcct ctcttcttct ttcgcggttc agcatgcagg aaaaagacgc ctcctcacaa       60
ggtttcctgc cacacttcca acatttcgcc acgcaggcga tccatgtggg ccaggatccg      120
```

-continued

```
gagcaatgga cctccagggc tgtagtgccc cccatctcac tgtccaccac gttcaagcaa      180
ggggcgcctg gccagcactc gggttttgaa tatagccgtt ctggaaatcc cactaggaat      240
tgccttgaaa aagcagtggc agcactggat ggggctaagt actgtttggc ctttgcttca      300
ggtttagcag ccactgtaac tattacccat cttttaaaag caggagacca aattatttgt      360
atggatgatg tgtatggagg tacaaacagg tacttcaggc aagtggcatc tgaatttgga      420
ttaaagattt cttttgttga ttgttccaaa atcaaattac tagaggcagc aattacacca      480
gaaaccaagc ttgtttggat cgaaaccccc acaaacccca cccagaaggt gattgacatt      540
gaaggctgtg cacatattgt ccataagcat ggagacatta ttttggtcgt ggataacact      600
tttatgtcac catatttcca cgcccttttg gctctgggag ctgatatttc tatgtattct      660
gcaacaaaat acatgaatgg ccacagtgat gttgtaatgg gcctggtgtc tgttaattgt      720
gaaagccttc ataatagact tcgtttcttg caaaactctc ttggagcagt tccatctcct      780
attgattgtt acctctgcaa tcgaggtctg aagactctac atgtccgaat ggaaaagcat      840
ttcaaaaacg gaatggcagt tgcccagttc ctggaatcta atccttgggt agaaaaggtt      900
atttatcctg ggctgcccct tcatccacag catgagttgg tgaagcgtca gtgtacaggt      960
tgtacaggga tggtcacctt ttatattaag ggcactcttc agcatgctga gattttcctc     1020
aagaacctaa agctatttac tctggccgag agcttgggag gattcgaaag ccttgctgag     1080
cttccggcaa tcatgactca tgcatcagtt cttaagaatg acagagatgt ccttggaatt     1140
agtgacacac tgattcgact ttctgtgggc ttagaggatg aggaagacct actggaagat     1200
ctagatcaag ctttgaaggc agcacaccct ccaagtggaa ttcacagcta gtattccaga     1260
gctgctatta gaagctgctt cctgtgaaga tcaatcttcc tgagtaatta atggaccaac     1320
aatgag                                                              1326
```

<210> SEQ ID NO 29
<211> LENGTH: 49
<212> TYPE: DNA
<213> ORGANISM: Artificial Sequence
<220> FEATURE:
<223> OTHER INFORMATION: Description of Artificial Sequence:PCR product

<400> SEQUENCE: 29

```
cccacggtcg gggtacctgg gcgggacgcg ccaggccgac tcccggcga               49
```

<210> SEQ ID NO 30
<211> LENGTH: 3464
<212> TYPE: DNA
<213> ORGANISM: Homo sapiens

<400> SEQUENCE: 30

```
tttaatggac acataattta attatatatt ttttcttaca gatacccagg tgttctctct       60
gatgtccagg aggagaaagg cattaagtac aaatttgaag tatatgagaa gaatgattaa      120
tatgaaggtg ttttctagtt taagttgttc cccctccctc tgaaaaaagt atgtatttt       180 acattagaaa aggttttttg ttgactttag atctataatt atttctaagc aactagtttt      240
tattccccac tactcttgtc tctatcagat accatttatg agacattctt gctataacta      300
agtgcttctc caagacccca actgagtccc cagcacctgc tacagtgagc tgccattcca      360
cacccatcac atgtggcact cttgccagtc cttgacattg tcgggctttt cacatgttgg      420
taatatttat taaagatgaa gatccacata cccttcaact gagcagtttc actagtggaa      480
```

-continued

| | |
|---|---|
| ataccaaaag cttcctacgt gtatatccag aggtttgtag ataaatgttg ccaccttgtt | 540 |
| tgtaacagtg aaaaattgaa aacaacctgg aagtccagtg atgggaaaat gagtatgttt | 600 |
| ctgtcttaga ttggggaacc caaagcagat tgcaagactg aaatttcagt gaaagcagtg | 660 |
| tatttgctag gtcataccag aaatcatcaa ttgaggtacg gagaaactga actgagaagg | 720 |
| taagaaaagc aatttaaagt cagcgagcag gttctcattg ataacaagct ccatactgct | 780 |
| gagatacagg gaaatggagg ggggaaagct ggagtattga tcccgccccc ctccttggtt | 840 |
| gtcagctccc tgtcctgtgt gtgggcggaa catagtccag ctgctctata gcaagtctca | 900 |
| ggtgtttgca gtaagaagct gctggcatgc acgggaacag tgaatgccaa acacttaaag | 960 |
| caattcgatg tttaagtatg taagttcttt tttttttaga cagcgtttcg ctcttgttgc | 1020 |
| ccaggctagc atgcaatggt gtgacctcgg cttactgcaa cctccgcctt cccagattca | 1080 |
| agcgattctc ctgcctcagg ctcccaagta gctaggacca ggtgcgcgcc accacgcccg | 1140 |
| gctaattttt gtattttgta ttttagtag agatgggggtt tcaccatgtt ggtcaggcta | 1200 |
| gtctcgaact cgtgaccgca agcgattcac ccacctcagc ctcccaaagt gctgggatta | 1260 |
| ccggcttgag ccaccacacc cggcacatct tcattctttt tatgtagtaa aaagtataag | 1320 |
| gccacacatg gtttatttga agtattttat aatttaaaaa aatacagaag caggaaaacc | 1380 |
| aattataagt tcaagtgagg gatgatggtt gcttgaacca aagggttgca tgtagtaaga | 1440 |
| aattgtgatt taagatatat tttaaagtta taagtagcag gatattctga tggagtttga | 1500 |
| ctttggtttt gggcccaggg agtttcgat gcctttgaga aatgaatgaa gtagagagaa | 1560 |
| aataaaagaa aaaccagcca ggcacagtgg ctcacacctg taatcccagc gctttgggag | 1620 |
| gctaaggcag gcagatcact tgagaccagc ttgggcaaca tggcaaagcc ccatctctac | 1680 |
| aaaaaacaca aaaattagct gggcattgtg gcgcacacct gtattcccat ctagtcagga | 1740 |
| agctgagatg gaagaattaa ttgagcccac gagttcaagg ctgcagtgag tcgtgattgt | 1800 |
| gccactgcac tccagccggg gtgacagaag agaccttgtc tcgaaaacga atctgaaaac | 1860 |
| aatggaacca tgccttcata attctagaaa gttattttca actgataaat ctatattcac | 1920 |
| ccaaataatc aagggtgaag gtaaaataat acatttttag acaagcaaag actcaggggt | 1980 |
| tacctccatg tgcccttttt agggaagctg ttggagaaaa tactccagca aaatgaagga | 2040 |
| gtacacaaac cagagaatga catgaatcca gcaaatagga tccaacacag gcaatattcc | 2100 |
| agctatggag ctagctttaa aaaggaacag taaaaatatt aatcggttag ctgggtggaa | 2160 |
| tggcccatgc ctgtagtccc agctactcag gaggctcagc agcaggacga cttgagccca | 2220 |
| agagttccag accagcctgg ccaccttagt gagatcccct ctcttaaaaa taataactta | 2280 |
| ttgccagatt tggggcattt ggaaagaagt tcattgaaga taaagcaaaa gtaaaaaaaa | 2340 |
| aaaaaaaaaa aacaagggga aagggttggt taggcaatca ttctagggca gaaagaagta | 2400 |
| caggatagga agagcataat acactgtttt tctcaacaag gagcagtatg tacacagtca | 2460 |
| taatgatgtg actgcttagc ccctaaatat ggtaactact ctgggacaat atgggaggaa | 2520 |
| aagtgaagat tgtgatggtg taagagctaa tcctcatctg tcatatccag aaatcactat | 2580 |
| ataatatata ataatgaaat gactaagtta tgtgaggaaa aaaacagaag acattgctaa | 2640 |
| aagagttaaa agtcattgct ctggagaatt aggaggatg gggcagggga ctgttaggat | 2700 |
| gcattataaa ctgaaaagcc ttttaaaat tttatgtatt aatatatgca ttcacttgaa | 2760 |
| aaactaaaaa aaaacaataa tttgaaaaaa cccatgaagg taactaacgg aaggaaaaac | 2820 |
| taagagaatg aaaagtattt gcctctggaa agaacaactg gcaggactgt tgttttcatt | 2880 |

-continued

| | |
|---|---|
| gtaagacttt tggagccatt taattgtact taaccatttt catctatttc tttaataaga | 2940 |
| acaattccat cttaataaag agttacactt gttaataagt gctggcctcc tgttgttctt | 3000 |
| tgtacacccc acacaaaatt tcaaagaaac tttgatggca atatatctcc atggtcagct | 3060 |
| taaaaataga gaaaggaaaa catagaatta gccaagagtc acacaaaaca aagatcagtt | 3120 |
| gtttgttagg aaacaatcaa aatcaagtct cacttttttcc agattggctt atggaacagc | 3180 |
| actgtaaggt gataacttgg ggcaaacatg taaataataa aacatatgtt ttaaatattc | 3240 |
| aggttagcac attttatgtt tctgtgagat taaaattgtg tgtgacatac ccgcttcctt | 3300 |
| aaaggcaatg tttctgaaaa tgttgtacct gctattcctg aatcagggat gggtcccaga | 3360 |
| atctgccttt taaacatctc agataatctg aagcctgctt aagtttgtaa ggcactgctt | 3420 |
| ttgcactcta aggaagaaaa aaacaagttt taattcccgt ctct | 3464 |

<210> SEQ ID NO 31
<211> LENGTH: 1584
<212> TYPE: DNA
<213> ORGANISM: Homo sapiens

<400> SEQUENCE: 31

| | |
|---|---|
| cggggcagct ctgaggaaca aggtggaagc tcagagcgct ggtctccacc ctggtgcccc | 60 |
| tgggctggtg ctggcagtgg gagccgtggc tgtggatgag agacatagac gagagagtga | 120 |
| gatggcctgg tttgccctct acctcctgag ccttctctgg gctacagctg gactagtac | 180 |
| ccagacccag agttcatgct ccgttccctc agcacaggag cccttggtca atggaataca | 240 |
| agtactcatg gagaactcgg tgacttcatc agcctaccca accccagca tcctgattgc | 300 |
| catgaatctg gccggagcct acaacttgaa ggcccagaag ctcctgactt accagctcat | 360 |
| gtccagcgac aacaacgatc taaccattgg gcacctcggc ctcaccatca tggcccctcac | 420 |
| ctcctcctgc cgagaccctg gggataaagt atccattcta caaagacaaa tggagaactg | 480 |
| ggcaccttcc agccccaacg ctgaagcatc agccttctat gggcccagtc tagcgatctt | 540 |
| ggcactgtgc cagaagaact ctgaggcgac cttgccgata gccgtccgct ttgccaagac | 600 |
| cctgctggcc aactcctctc ccttcaatgt agacacagga gcaatggcaa ccttggctct | 660 |
| gacctgtatg tacaacaaga tccctgtagg ttcagaggaa ggttacagat ccctgttggg | 720 |
| tcaggtacta aaggatattg tggagaaaat cagcatgaag atcaaagata tggcatcat | 780 |
| tggagacatc tacagtactg gcctcgccat gcaggctctc tctgtaacac ctgagccatc | 840 |
| taaaaaggaa tggaactgca agaagactac ggatatgata ctcaatgaga ttaagcaggg | 900 |
| gaaattccac aaccccatgt ccattgctca aatcctccct tccctgaaag caagacata | 960 |
| cctagatgtg ccccaggtca cttgtagtcc tgatcatgag gtacaaccaa ctctacccag | 1020 |
| caaccctggc cctggcccca cctctgcatc taacatcact gtcatataca ccataaataa | 1080 |
| ccagctgagg ggggttgagc tgctcttcaa cgagaccatc aatgttagtg tgaaaagtgg | 1140 |
| gtcagtgtta cttgttgtcc tagaggaagc acagcgcaaa atcctatgt tcaaatttga | 1200 |
| aaccacaatg acatcttggg gccttgtcgt ctcttctatc aacaatatcg cggaaaatgt | 1260 |
| taatcacaag acatactggc agtttcttag tggtgtaaca ccttttgaatg aaggggttgc | 1320 |
| tgactacata cccttcaacc acgagcacat cacagccaat ttcacacagt actaacgaag | 1380 |
| aggtgggttc agcttctatc aaacatctcc aaaggatggg tgaattttt tccacttcat | 1440 |
| tttaaatcta tgcaaaaaag cgaatgcctg tgatgctacc atattcctgg taaaaacatg | 1500 |

```
gagaaccact atgtagaata aaaatgcaaa gttcactgga gtctcaacat ctatgactca    1560
tgaaaataaa attttcatct tctc                                          1584

<210> SEQ ID NO 32
<211> LENGTH: 1537
<212> TYPE: DNA
<213> ORGANISM: Homo sapiens

<400> SEQUENCE: 32
gctctcatta ccttctgccc atcacttaat aaatagccag ccaattcatc aacattctgg     60
tacactgttg gagagatgag acagtcacac cagctgcccc tagtggggct cttactgttt    120 tctttattc caagccaact atgcgagatt tgtgaggtaa gtgaagaaaa ctacatccgc     180
ctaaaacctc tgttgaatac aatgatccag tcaaactata acaggggaac cagcgctgtc    240
aatgttgtgt tgtccctcaa acttgttgga atccagatcc aaaccctgat gcaaaagatg    300
atccaacaaa tcaaatacaa tgtgaaaagc agattgtcag atgtaagctc gggagagctt    360
gccttgatta tactggcttt gggagtatgt cgtaacgctg aggaaaactt aatatatgat    420
taccacctga ctgacaagct agaaaataaa ttccaagcag aaattgaaaa tatggaagca    480
cacaatggca ctcccctgac taactactac cagctcagcc tggacgtttt ggccttgtgt    540
ctgttcaatg ggaactactc aaccgccgaa gttgtcaacc acttcactcc tgaaaataaa    600 aactatatt ttggtagcca gttctcagta gatactggtg caatggctgt cctggctctg     660
acctgtgtga agaagagtct aataaatggg cagatcaaag cagatgaagg cagtttaaag    720
aacatcagta tttatacaaa gtcactggta gaaaagattc tgtctgagaa aaagaaaat     780 ggtctcattg gaaacacatt tagcacagga gaagccatgc aggccctctt tgtatcatca    840
gactattata atgaaaatga ctggaattgc caacaaactc tgaatacagt gctcacggaa    900
atttctcaag gagcattcag taatccaaac gctgcagccc aggtcttacc tgccctgatg    960
ggaaagacct tcttggatat aacaaagac tcttcttgcg tctctgcttc aggtaacttc    1020
aacatctccg ctgatgagcc tataactgtg cacctcctg actcacaatc atatatctcc    1080
gtcaattact ctgtgagaat caatgaaaca tatttcacca atgtcactgt gctaaatggt    1140
tctgtcttcc tcagtgtgat ggagaaagc cagaaaatga atgatactat atttggtttc    1200
acaatggagg agcgctcatg ggggccctat atcacctgta ttcagggcct atgtgccaac    1260
aataatgaca gaacctactg gaacttctg agtggaggcg aaccactgag ccaaggagct    1320
ggtagttacg ttgtccgcaa tggagaaaac ttggaggttc gctggagcaa atactaataa    1380
gcccaaactt tcctcagctg cataaaatcc atttgcagtg gagttccatg tttattgtcc    1440
ttatgccttc ttcttcattt atcccagtac gagcaggaga gttaataacc tcccttctc    1500 tctctacatg ttcaataaaa gttgttgaaa gattaac                            1537

<210> SEQ ID NO 33
<211> LENGTH: 1866
<212> TYPE: DNA
<213> ORGANISM: Homo sapiens

<400> SEQUENCE: 33
ccgattcttg ctcactgctc acccacctgc tgctgccatg aggcaccttg gggccttcct     60
cttccttctg ggggtcctgg gggccctcac tgagatgtgt gaaataccag agatggacag    120
ccatctggta gagaagttgg gccagcacct cttccttgg atggaccggc tttccctgga    180
gcacttgaac cccagcatct atgtgggcct acgcctctcc agtctgcagg ctgggaccaa    240
```

-continued

```
ggaagacctc tacctgcaca gcctcaagct tggttaccag cagtgcctcc tagggtctgc    300
cttcagcgag gatgacggtg actgccaggg caagccttcc atgggccagc tggccctcta    360
cctgctcgct ctcagagcca actgtgagtt tgtcaggggc cacaaggggg acaggctggt    420
ctcacagctc aaatggttcc tggaggatga aagagagcc attgggcatg atcacaaggg     480
ccacccccac actagctact accagtatgg cctgggcatt ctggccctgt gtctccacca    540
gaagcgggtc catgacagcg tggtggacaa acttctgtat gctgtggaac ctttccacca   600
gggccaccat tctgtggaca cagcagccat ggcaggcttg gcattcacct gtctgaagcg    660
ctcaaacttc aaccctggtc ggagacaacg gatcaccatg ccatcagaa cagtgcgaga    720 ggagatcttg aaggcccaga ccccgaggg ccactttggg aatgtctaca gcacccatt     780 ggcattacag ttcctcatga cttcccccat gcctggggca gaactgggaa cagcatgtct   840
caaggcgagg gttgctttgc tggccagtct gcaggatgga gccttccaga atgctctcat   900
gatttcccag ctgctgcccg ttctgaacca caagacctac attgatctga tcttcccaga    960
ctgtctggca ccacgagtca tgttggaacc agctgctgag accattcctc agacccaaga   1020
gatcatcagt gtcacgctgc aggtgcttag tctcttgccg ccgtacagac agtccatctc    1080
tgttctggcc gggtccaccg tggaagatgt cctgaagaag gcccatgagt taggaggatt    1140
cacatatgaa acacaggcct cctcgtcagg ccctactta acctccgtga tggggaaagc     1200
ggccggagaa agggagttct ggcagcttct ccgagacccc aacacccac tgttgcaagg     1260 tattgctgac tacagaccca aggatggaga aaccattgag ctgaggctgg ttagctggta    1320
gcccctgagc tccctcatcc cagcagcctc gcacactccc taggcttcta ccctccctcc    1380
tgatgtccct ggaacaggaa ctcgcctgac cctgctgcca cctcctgtgc actttgagca    1440 atgcccctg ggatcacccc agccacaagc ccttcgaggg ccctatacca tggcccacct    1500
tggagcagag agccaagcat cttccctggg aagtctttct ggccaagtct ggccagcctg    1560
gccctgcagg tctcccatga aggccacccc atggtctgat gggcatgaag catctcagac    1620
tccttggcaa aaaacggagt ccgcaggccg caggtgttgt gaagaccact cgttctgtgg   1680
ttggggtcct gcaagaaggc ctcctcagcc cgggggctat ggccctgacc ccagctctcc    1740
actctgctgt tagagtggca gctctgagct ggttgtggca cagtagctgg ggagacctca    1800
gcagggctgc tcagtgcctg cctctgacaa aattaaagca ttgatggcct gtggacctgc    1860
aaaaaa                                                              1866
```

<210> SEQ ID NO 34
<211> LENGTH: 2798
<212> TYPE: DNA
<213> ORGANISM: Homo sapiens

<400> SEQUENCE: 34

```
gccctctccc acagcggagt ccaaaacagg cctaccagtc agttcttatt tctattgggt     60
gtttccatgc tccaccatgt taagagctaa gaatcagctt ttttactttt cacctcatta    120
cctgaggcag gtaaaagaat catcaggctc caggctcata cagcaacgac ttctacacca    180
gcaacagccc cttcacccag aatgggctgc cctggctaaa aagcagctga aaggcaaaaa   240
cccagaagac ctaatatggc acaccccgga agggatctct ataaaaccct tgtattccaa    300
gagagatact atggacttac ctgaagaact tccaggagtg aagccattca cacgtggacc    360
atatcctacc atgtataccet ttaggccctg gaccatccgc cagtatgctg gttttagtac   420
```

-continued

```
tgtggaagaa agcaataagt tctataagga caacattaag gctggtcagc agggattatc    480
agttgccttt gatctggcga cacatcgtgg ctatgattca gacaaccctc gagttcgtgg    540
tgatgttgga atggctggag ttgctattga cactgtggaa gataccaaaa ttcttttga    600
tggaattcct ttagaaaaaa tgtcagtttc catgactatg aatggagcag ttattccagt    660
tcttgcaaat tttatagtaa ctggagaaga acaaggtgta cctaaagaga aacttactgg    720
taccatccaa aatgatatac taaaggaatt tatggttcga aatacataca tttttcctcc    780
agaaccatcc atgaaaatta ttgctgacat atttgaatat acagcaaagc acatgccaaa    840
atttaattca atttcaatta gtggatacca tatgcaggaa gcaggggctg atgccattct    900
ggagctggcc tatactttag cagatggatt ggagtactct agaactggac tccaggctgg    960
cctgacaatt gatgaatttg caccaaggtt gtctttcttc tggggaattg gaatgaattt   1020
ctatatggaa atagcaaaga tgagagctgg tagaagactc tgggctcact aatagagaa    1080
aatgtttcag cctaaaaact caaaatctct tcttctaaga gcacactgtc agacatctgg   1140
atggtcactt actgagcagg atccctacaa taatattgtc cgtactgcaa tagaagcaat   1200
ggcagcagta tttggaggga ctcagtcttt gcacacaaat tcttttgatg aagctttggg   1260
tttgccaact gtgaaaagtg ctcgaattgc caggaacaca caaatcatca ttcaagaaga   1320
atctgggatt cccaaagtgg ctgatccttg gggaggttct tacatgatgg aatgtctcac   1380
aaatgatgtt tatgatgctg cttaaagct cattaatgaa attgaagaaa tgggtggaat   1440
ggccaaagct gtagctgagg gaataccaa acttcgaatt gaagaatgtg ctgcccgaag   1500
acaagctaga atagattctg gttctgaagt aattgttgga gtaaataagt accagttgga   1560
aaaagaagac gctgtagaag ttctggcaat tgataatact tcagtgcgaa acaggcagat   1620
tgaaaaactt aagaagatca aatccagcag ggatcaagct ttggctgaac attgtcttgc   1680
tgcactaacc gaatgtgctg ctagcggaga tggaaatatc ctggctcttg cagtggatgc   1740
atctcgggca agatgtacag tgggagaaat cacagatgcc ctgaaaaagg tatttggtga   1800
acataaagcg aatgatcgaa tggtgagtgg agcatatcgc caggaatttg agaaagtaa    1860
agagataaca tctgctatca agagggttca taaattcatg gaacgtgaag gtcgcagacc   1920
tcgtcttctt gtagcaaaaa tgggacaaga tggccatgac agaggagcaa aagttattgc   1980
tacaggattt gctgatcttg gttttgatgt ggacataggc cctcttttcc agactcctcg   2040
tgaagtggcc cagcaggctg tggatgcgga tgtgcatgct gtgggcgtaa gcaccctcgc   2100
tgctggtcat aaaaccctag ttcctgaact catcaaagaa cttaactccc ttggacggcc   2160
agatattctt gtcatgtgtg gagggtgat accacctcag gattatgaat ttctgtttga   2220
agttggtgtt tccaatgtat ttggtcctgg gactcgaatt ccaaaggctg ccgttcaggt   2280
gcttgatgat attgagaagt gtttggaaaa gaagcagcaa tctgtataat atcctctttt   2340
tgttttagct tttgtctaaa atattatttt agttatgatc aaagaagaga gtaaagctat   2400
gtcttcaatt taatttcaat acctgatttg tactttcctt gaaagcttta ctttaaaata   2460
ccttacttat aggcctggtg tcatgctata agtatgtaca tacagtttca cttcaaaaat   2520
aaaaaaaaat ccctaaaaac tctctatact ctctataaca atactttatc aagaactctg   2580
gacaatggta ttatttttaa aaatcatggt gatgtattta ttagaatgtt tcttataaat   2640
ctctttcatt tttatattaa gaattaaact gtacctaaaa aaactctgac tattcccatt   2700
tctcagttta gcattacatt gtcttgagca ccagaaaata aaatccatat attaattaaa   2760
acctatcttg aaaaaaaaaa aaaaaaaaaa aaaaaaa                             2798
```

<210> SEQ ID NO 35
<211> LENGTH: 1637
<212> TYPE: DNA
<213> ORGANISM: Homo sapiens

<400> SEQUENCE: 35

| | | | | | |
|---|---|---|---|---|---|
| aagaactggc | ctgtacattt | tcaaggaatt | cttgagaggt | tcttggagag | attctgggag | 60 |
| ccaaacactc | cattgggatc | ctagctgttt | tagagaacaa | cttgtaatgg | agccttcatc | 120 |
| tcttgagctg | ccggctgaca | cagtgcagcg | cattgcggct | gaactcaaat | gccacccaac | 180 |
| ggatgagagg | gtggctctcc | acctagatga | ggaagataag | ctgaggcact | tcagggagtg | 240 |
| cttttatatt | cccaaaatac | aggatctgcc | tccagttgat | ttatcattag | tgaataaaga | 300 |
| tgaaaatgcc | atctatttct | tgggaaattc | tcttggcctt | caaccaaaaa | tggttaaaac | 360 |
| atatcttgaa | gaagaactag | ataagtgggc | caaaatagca | gcctatggtc | atgaagtggg | 420 |
| gaagcgtcct | tggattacag | agatgagag | tattgtaggc | cttatgaagg | acattgtagg | 480 |
| agccaatgag | aaagaaatag | ccctaatgaa | tgctttgact | gtaaatttac | atcttctaat | 540 |
| gttatcattt | tttaagccta | cgccaaaacg | atataaaatt | cttctagaag | ccaaagcctt | 600 |
| cccttctgat | cattatgcta | ttgagtcaca | actacaactt | cacggactta | acattgaaga | 660 |
| aagtatgcgg | atgataaagc | caagagaggg | ggaagaaacc | ttaagaatag | aggatatcct | 720 |
| tgaagtaatt | gagaaggaag | gagactcaat | tgcagtgatc | ctgttcagtg | gggtgcattt | 780 |
| ttacactgga | cagcacttta | atattcctgc | catcacaaaa | gctggacaag | cgaagggttg | 840 |
| ttatgttggc | tttgatctag | cacatgcagt | tggaaatgtt | gaactctact | tacatgactg | 900 |
| gggagttgat | tttgcctgct | ggtgttccta | caagtattta | aatgcaggag | caggaggaat | 960 |
| tgctggtgcc | ttcattcatg | aaaagcatgc | ccatacgatt | aaacctgcat | tagtgggatg | 1020 |
| gtttggccat | gaactcagca | ccagatttaa | gatggataac | aaactgcagt | taatccctgg | 1080 |
| ggtctgtgga | ttccgaattt | caaatcctcc | catttttgttg | gtctgttcct | tgcatgctag | 1140 |
| tttagagatc | tttaagcaag | cgacaatgaa | ggcattgcgg | aaaaaatctg | ttttgctaac | 1200 |
| tggctatctg | gaatacctga | tcaagcataa | ctatggcaaa | gataaagcag | caaccaagaa | 1260 |
| accagttgtg | aacataatta | ctccgtctca | tgtagaggag | cgggggtgcc | agctaacaat | 1320 |
| aacattttct | gttccaaaca | aagatgttttt | ccaagaacta | gaaaaagag | gagtggtttg | 1380 |
| tgacaagcgg | aatccaaatg | gcattcgagt | ggctccagtt | cctctctata | attctttcca | 1440 |
| tgatgtttat | aaatttacca | atctgctcac | ttctatactt | gactctgcag | aaacaaaaaa | 1500 |
| ttagcagtgt | tttctagaac | aacttaagca | aattatactg | aaagctgctg | tggttatttc | 1560 |
| agtattattc | gatttttaat | tattgaaagt | atgtcaccat | tgaccacatg | taactaacaa | 1620 |
| taaataatat | accttac | | | | | 1637 |

<210> SEQ ID NO 36
<211> LENGTH: 1908
<212> TYPE: DNA
<213> ORGANISM: Homo sapiens

<400> SEQUENCE: 36

| | | | | | |
|---|---|---|---|---|---|
| gaattcatga | aaacgtagct | cgtcctcaaa | aaaaacagaa | gaggagtaat | cattttaagg | 60 |
| gagaaatata | tacgaaagga | acaagatttt | gaagcaccca | agctgccacc | tacattaaaa | 120 |
| cacggtaggt | ggctaaacac | cagtcttcaa | tgcccttcca | cagcctcagt | ctgaaaaata | 180 |

```
ctgtgcaggt gacccaagtg aggggtcacc cttgggcttt tcctgtggca gtatctctgg    240
tttaaaaaca aacaaacgta cttattgcgt tgaaggacgg caacaggaag gactccatga    300
ttagtcacat ctataccatc ctaagaaact ttatccaccc aaactgtatt tcagacttta    360
taatctaaac tacaaaaagt gttcactggg gaactgcaca atatgactgc ttttaaccgt    420
agtgatttca aatattgagc catgctgttg cagtcttaaa aactggagac ctaagggcag    480
ctttcttcta gtcacccaat ccagcacttt tttaaaaaat cagtaaaact cttcgaccac    540
caaggaaaaa aaaaaggat ggaggttaaa agacgcaccc cttgcccaca agcccctca    600 tcagaatggg agtcaggaga cctgagttcc tgtctcaggc ctgccattaa aaacctgcat    660
aacctttgcc tatctcctca aacggaagta ctaaaacctc agcgcttcac ccaatttgta    720
gccccggctg ggctcttccc accttcccct tcttcagccc gccccttcct cctcagccc    780 tatcatcggg cggagggtcc ccgcctccgc ccgccttacc cacaagcccc gccccccag    840 ccccgatggc cctgcccagt cccagacaga acctactacg tgcggcggca gctggggcgg    900
gaaggcgggc gctgggggcg ctgcggccgc tgcagcgcag ggtccacctg gtcggctgca    960
cctgtggagg aggaggtgga tttcaggctt cccgtagact ggaagaatcg gctcaaaacc   1020
gcttgcctcg caggggctga gctggaggca gcgaggccgc ccgacgcagg cttccggcga   1080
gacatggcag ggcaaggatg gcagcccggc ggcagggccc ggcgaggagc gcgaacccgc   1140
ggccgcagtt cccaggcgtc tgcgggcgcg agcacgccgc gaccctgcgt gcgccggggc   1200
ggggggggcg ggcctcgcct gcacaaatag ggacgagggg gcggggcggc cacaatttcg   1260
cgccaaactt gaccgcgcgt tctgctgtaa cgagcgggct cggaggtcct cccgctgctg   1320
tcatggttgg ttcgctaaac tgcatcgtcg ctgtgtccca gaacatgggc atcggcaaga   1380
acggggacct gccctggcca ccgctcaggt atctgccggg ccggggcgat gggacccaaa   1440
cgggcgcagg ctgcccacgg tcggggtacc tgggcgggac gcgccggccg actcccggcg   1500
agaggatggg gccagacttg cggtctgcgc tggcaggaag ggtgggcccg actggattcc   1560
ccttttctgc tgcgcgggag gcccagttgc tgatttctgc ccggattctg ctgcccggtg   1620
aggtcttgcc ctgcggcgcc ctcgcccagg gcaaagtccc agccctggag aaaacacctc   1680 accccctaccc acagcgctcc gtttgtcagg tgccttagag ctcgagccca agggataatg   1740
tttcgagtaa cgctgtttct ctaacttgta ggaatgaatt cagatatttc cagagaatga   1800
ccacaacctc ttcagtagaa ggtaatgtgg gattaagtag ggtcttgctt gatgaagttt   1860
accagtgcaa atgttagtta aatggaaagt tttccgtgtt aatctggg               1908
```

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 37
cccacggtcg gggtggccga ctcccggcga                                      30

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 38

```
ctaaactgca tcgtcgctgt g                                              21

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence:primer

<400> SEQUENCE: 39 aaaagggaa tccagtcgg                                                  19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence:PCR product

<400> SEQUENCE: 40
acctgggcgg gacgcgcca                                                 19

<210> SEQ ID NO 41
<211> LENGTH: 1275
<212> TYPE: DNA
<213> ORGANISM: Homo sapiens

<400> SEQUENCE: 41
ctgcagcgcc agggtccacc tggtcggctg cacctgtgga ggaggaggtg gatttcaggc    60
ttcccgtaga ctggaagaat cggctcaaaa ccgcttgcct cgcaggggct gagctggagg   120
cagcgaggcc gcccgacgca ggcttccggc gagacatggc agggcaagga tggcagcccg   180
gcggcagggc ccggcgagga gcgcgaaccc gcggccgcag ttcccaggcg tctgcgggcg   240
cgagcacgcc gcgaccctgc gtgcgccggg cgggggggc ggggcctcgc ctgcacaaat    300
agggacgagg gggcggggcg gccacaattt cgcgccaaac ttgaccgcgc gttctgctgt   360
aacgagcggg ctcggaggtc ctcccgctgc tgtcatggtt ggttcgctaa actgcatcgt   420
cgctgtgtcc cagaacatgg gcatcggcaa gaacgggggac ctgccctggc caccgctcag   480
gtatctgccg ggccggggcg atgggaccca acgggcgca ggctgcccac ggtcggggta   540
cctgggcggg acgcgccagg ccgactcccg gcgagaggat ggggccagac ttgcggtctg   600
cgctggcagg aagggtgggc ccgactggat tccccttttc tgctgcgcgg gaggcccagt   660
tgctgatttc tgcccggatt ctgctgcccg gtgaggtctt tgccctgcgg cgccctcgcc   720
cagggcaaag tccagcccct ggagaaaaca cctcaccct acccacagcg ctccgttttgt   780 caggtgcctt agagctcgag cccaagggat aatgtttcga gtaacgctgt ttctctaact   840
tgtaggaatg aattcagata tttccagaga atgaccacaa cctcttcagt agaaggtaat   900
gtgggattaa gtagggtctt gcttgatgaa gtttaccagt gcaaatgtta gttaaatgga   960
aagttttccg tgttaatctg ggacctttc tcttattatg gatctgtatg atctgtatgc   1020
agttcccaag gttcatttac cattattaaa aaatttttgt cttagaaatt ttatgtatgt   1080
caacgcacga gcaaattatc aggcatgggg cagaattggc aactgggtgg aggcttcggt   1140
ggaggttagc actccgaaag gaaaacagag taggcctttg gaacagctgc tggaagagat   1200
aaggcctgaa caagggcagt ggagaagaga gggtaaaaat tttttaaggt tacatgaccc   1260
tggattttgg agatc                                                   1275
```

<210> SEQ ID NO 42
<211> LENGTH: 1256
<212> TYPE: DNA
<213> ORGANISM: Homo sapiens

<400> SEQUENCE: 42

```
ctgcagcgcc agggtccacc tggtcggctg cacctgtgga ggaggaggtg gatttcaggc      60
ttcccgtaga ctggaagaat cggctcaaaa ccgcttgcct cgcaggggct gagctggagg     120
cagcgaggcc gcccgacgca ggcttccggc gagacatggc agggcaagga tggcagcccg     180
gcggcagggc ccggcgagga gcgcgaaccc gcggccgcag ttcccaggcg tctgcgggcg     240
cgagcacgcc gcgaccctgc gtgcgccggg gcggggggc ggggcctcgc ctgcacaaat     300
agggacgagg gggcggggcg gccacaattt cgcgccaaac ttgaccgcgc gttctgctgt     360
aacgagcggg ctcggaggtc ctcccgctgc tgtcatggtt ggttcgctaa actgcatcgt     420
cgctgtgtcc cagaacatgg gcatcggcaa gaacggggac ctgccctggc caccgctcag     480
gtatctgccg ggccggggcg atgggaccca acgggcgca ggctgcccac ggtcggggtg     540
gccgactccc ggcgagagga tggggccaga cttgcggtct gcgctggcag gaagggtggg     600
cccgactgga ttccccttt ctgctgcgcg ggaggcccag ttgctgattt ctgcccggat     660
tctgctgccc ggtgaggtct ttgccctgcg gcgcccctcgc ccagggcaaa gtcccagccc     720
tggagaaaac acctcacccc tacccacagc gctccgtttg tcaggtgcct tagagctcga     780
gcccaaggga taatgtttcg agtaacgctg tttctctaac ttgtaggaat gaattcagat     840
atttccagag aatgaccaca acctcttcag tagaaggtaa tgtgggatta agtagggtct     900
tgcttgatga agtttaccag tgcaaatgtt agtaaatgg aaagttttcc gtgttaatct     960
gggaccttt ctcttattat ggatctgtat gatctgtatg cagttcccaa ggttcattta    1020
ccattattaa aaatttttg tcttagaaat tttatgtatg tcaacgcacg agcaaattat    1080
caggcatggg gcagaattgg caactgggtg gaggcttcgg tggaggttag cactccgaaa    1140
ggaaaacaga gtaggccttt ggaacagctg ctggaagaga taaggcctga acaagggcag    1200
tgagaagag agggtaaaaa ttttttaagg ttacatgacc ctggattttg gagatc        1256
```

<210> SEQ ID NO 43
<211> LENGTH: 55
<212> TYPE: DNA
<213> ORGANISM: Artificial Sequence
<220> FEATURE:
<223> OTHER INFORMATION: Description of Artificial Sequence:PCR product

<400> SEQUENCE: 43

```
gctgcccacg gtcggggtac ctgggcggga cgcgccaggc cgactcccgg cgaga           55
```

<210> SEQ ID NO 44
<211> LENGTH: 36
<212> TYPE: DNA
<213> ORGANISM: Artificial Sequence
<220> FEATURE:
<223> OTHER INFORMATION: Description of Artificial Sequence:PCR product

<400> SEQUENCE: 44

```
gctgcccacg gtcggggtgg ccgactcccg gcgaga                                 36
```

<210> SEQ ID NO 45
<211> LENGTH: 1273
<212> TYPE: DNA
<213> ORGANISM: Homo sapiens

<400> SEQUENCE: 45

```
ctgcagcgca gggtccacct ggtcggctgc acctgtggag gaggaggtgg atttcaggct        60
tcccgtagac tggaagaatc ggctcaaaac cgcttgcctc gcagggggctg agctggaggc       120 agcgaggccg cccgacgcag gcttccggcg agacatggca gggcaaggat ggcagcccgg       180
cggcagggcc cggcgaggag cgcgaacccg cggccgcagt tcccaggcgt ctgcgggcgc       240
gagcacgccg cgaccctgcg tgcgccgggg cggggggggcg gggcctcgcc tgcacaaata       300
gggacgaggg ggcggggcgg ccacaatttc gcgccaaact tgaccgcgcg ttctgctgta       360
acgagcgggc tcggaggtcc tcccgctgct gtcatggttg gttcgctaaa ctgcatcgtc       420
gctgtgtccc agaacatggg catcggcaag aacggggacc tgccctggcc accgctcagg       480
tatctgccgg gccggggcga tgggacccaa acgggcgcag gctgcccacg gtcggggtac       540
ctgggcggga cgcgccggcc gactcccggc gagaggatgg ggccagactt gcggtctgcg       600
ctggcaggaa gggtgggccc gactggattc ccctttctg ctgcgcggga ggcccagttg       660
ctgatttctg cccggattct gctgcccggt gaggtctttg ccctgcggcg ccctcgccca       720
gggcaaagtc ccagccctgg agaaaacacc tcaccctac ccacagcgct ccgtttgtca       780
ggtgccttag agctcgagcc caagggataa tgtttcgagt aacgctgttt ctctaacttg       840
taggaatgaa ttcagatatt tccagagaat gaccacaacc tcttcagtag aaggtaatgt       900
gggattaagt agggtcttgc ttgatgaagt ttaccagtgc aaatgttagt taaatggaaa       960
gttttccgtg ttaatctggg accttttctc ttattatgga tctgtatgat ctgtatgcag      1020
ttcccaaggt tcatttacca ttattaaaaa attttttgtct tagaaatttt atgtatgtca      1080
acgcacgagc aaattatcag gcatggggca gaattggcaa ctgggtggag gcttcggtgg      1140
aggttagcac tccgaaagga aaacagagta ggcctttgga acagctgctg gaagagataa      1200
ggcctgaaca agggcagtgg agaagagagg gtaaaaattt tttaaggtta catgaccctg      1260
gattttggag atc                                                         1273
```

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence:PCR product

<400> SEQUENCE: 46

```
acctgggcgg gacgcgcc                                                      18
```